(12) United States Patent
Lynch et al.

(10) Patent No.: US 7,820,703 B2
(45) Date of Patent: Oct. 26, 2010

(54) LYSOPHOSPHATIDIC ACID RECEPTOR SELECTIVE ANTAGONISTS

(75) Inventors: Kevin R. Lynch, Charlottesville, VA (US); Timothy L. Macdonald, Charlottesville, VA (US); Brian H. Heasley, Wake Forest, NC (US)

(73) Assignee: University of Virginia Patent Foundation, Charlottesville, VA (US)

( * ) Notice: Subject to any disclaimer, the term of this patent is extended or adjusted under 35 U.S.C. 154(b) by 357 days.

(21) Appl. No.: 11/579,658

(22) PCT Filed: May 6, 2005

(86) PCT No.: PCT/US2005/016011

§ 371 (c)(1),
(2), (4) Date: Nov. 6, 2006

(87) PCT Pub. No.: WO2005/115150

PCT Pub. Date: Dec. 8, 2005

(65) Prior Publication Data

US 2008/0318901 A1    Dec. 25, 2008

Related U.S. Application Data

(60) Provisional application No. 60/568,520, filed on May 6, 2004.

(51) Int. Cl.
*A61K 31/44* (2006.01)
*C07F 9/06* (2006.01)
(52) U.S. Cl. .................................. 514/367; 546/22
(58) Field of Classification Search .................. 546/22; 514/357
See application file for complete search history.

(56) References Cited

U.S. PATENT DOCUMENTS

| | | | |
|---|---|---|---|
| RE29,829 | E | 11/1978 | Bordenca et al. |
| 4,331,685 | A | 5/1982 | Tokuda et al. |
| 4,845,292 | A | 7/1989 | McGregor et al. |
| 4,906,767 | A | 3/1990 | Mathias et al. |
| 5,219,884 | A | 6/1993 | Fujita et al. |
| 5,307,308 | A | 4/1994 | Noguchi |
| 5,405,988 | A | 4/1995 | Klar et al. |
| 5,604,229 | A | 2/1997 | Fujita et al. |
| 5,773,475 | A | 6/1998 | Kohn et al. |
| 6,380,177 | B1 | 4/2002 | Erickson |
| 7,169,818 | B2 | 1/2007 | Lynch et al. |

FOREIGN PATENT DOCUMENTS

| | | |
|---|---|---|
| DE | 4225488 | 7/1992 |
| EP | 1 156 054 B1 | 4/2004 |
| WO | WO 96/18600 | 6/1996 |
| WO | WO 96/31124 | 10/1996 |
| WO | WO 98/45249 | 10/1998 |
| WO | WO/99 047101 | 9/1999 |
| WO | WO 01/57057 | 8/2001 |
| WO | WO 01/71022 | 9/2001 |
| WO | WO 02/06268 | 1/2002 |
| WO | WO/02 29001 A2 | 4/2002 |
| WO | WO 02/018395 | 7/2002 |

OTHER PUBLICATIONS

Heasley et al., Bioorganic & Medicinal Chemistry, 2004, 14(11), pp. 2735-2740.*
Bektas, Meryem et al. The G Protein-Coupled Receptor GPR4 Suppresses ERK Activation in a Ligand-Independent Manner. Biochemistry. 2003. vol. 42, 12181-12191.
Choi, D. et al. Synthesis and Anticonvulsant Activities of N-Benzyl-2-acetamidopropionamide Derivatives, J. Med. Chem., 1996.vol. 39, 1907-1916.
Ferry, Gilles et al. A Nanomolar Inhibitor of Autotaxin : Discovery, Synthesis and Applications as a Pharmacological Tool. J. Pharmacology And Experimental Therapeutics. 2008. vol. 327, No. 3, 809-819.
Gajewiak, Joanna et al. Alkoxymethylenephosphonate Analogues of (Lyso) phosphatidic Acid Stimulate Signaling Networks Coupled to the $LPA_2$ Receptor. Chem. Med. Chem. 2007. vol. 2, 1789-1798.
Heasley, Brian H. et al. Initial structure-activity relationships of lysophosphatidic acid receptor antagonists: discovery of a high-affinity $LPA_1/LPA_3$ receptor antagonist. Bioorganic & Medicinal Chemistry Letters. 2004. 2735-2740.
Heasley, Brian H. et al. A novel series of 2-pyridyl-containing compounds as lysophosphatidic acid receptor antagonists: development of a nonhydrolyzable $LPA_3$ receptor-selective antagonist. Bioorganic & Medicinal Chemistry Letters. 2004. 4069-4074.
Jiang, Guowei et al. α-Substituted Phosphonate Analogues of Lysophosphatidic Acid (LPA) Selectively Inhibit Production and Action of LPA. Chem. Med. Chem. 2007. vol. 2, 679-690.
Santos, Webster L., et al. The Molecular Pharmacology of Lysophosphatidate Signaling. Annals New York Academy of Sciences. 2000. vol. 905, 232-241.
Santos, Webster L. et al. Synthesis and biological evaluation of phosphonic and thiophosphoric acid derivatives of lysophosphatidic acid. Bioorganic & Medicinal Chemistry Letters. 2004. 3473-3476.
Sturtz, Georges et al. About an original pharmacomodulation approach of methotrexate: synthesis of gem-diphosphonic amethopterine and N-10 deaza analogs. Academie des Sciences. 1990. 739-742.
Sturtz, Georges et al. Analogues phosphonoglutamiques d'amethopterine (methotrexate). Eur. J. Med. Chem. 1984. vol. 19, No. 3, 267-273.
Sturtz,G., et al. A study of the deliver-targeting concept applied to antineoplastic drugs active on human osteosarcoma. I. Synthesis & biolocial activity in nude mice carrying human osteosarcoma xenografts of gem-bisphosphonic methotrexate analogues.Eur. J. Med. Chem. 1992., vol. 27, 825-833.

(Continued)

*Primary Examiner*—Rei-tsang Shiao
(74) *Attorney, Agent, or Firm*—Prout International IP, LLC

(57) ABSTRACT

The present invention is directed to compositions comprising lysophosphatidic acid analogs and methods of using such analogs as agonist or antagonists of LPA receptor activity. In addition the invention is directed to LPA receptor agonists that vary in the degree of selectivity at individual LPA receptors (i.e. LPA1, LPA2 and LPA3). More particularly the present invention is directed to LPA analogs wherein the glycerol is replaced with ethanolamine and a variety of substitutions have been linked at the second carbon atom.

17 Claims, 10 Drawing Sheets

OTHER PUBLICATIONS

Sugiura, Takayuki et al. Biochemical Characterization of the Interaction of Lipid Phosphoric Acids with Human Platelets: Comparison with Platelet Activating Factor. Archives of Biochemistry & Biophysics. 1994. vol. 311(2), 358-368.

Tsukamoto, Takashi et al. Mechanism-Based Inhibition of Human Folypolyglutamate Synthetase: Design, Synthesis, and Biochemical Characterization of a Phophapeptide Mimic of the Tetrahedral Intermediate. Archives of Biochemistry & Biophysics, 1998. vol. 355(1),109-118.

Xu, Yong et al. Alkyl lysophosphatidic acid and fluoromethylene phosphonate analogs as metabolically-stabilized agonists for LPA receptors. Bioorganic & Medicinal Chemistry Letters. 2004. 5323-5328.

Xu, Yong et al. Structure-Activity Relationships of Fluorinated Lysophosphatidic Acid Analogues. J. Medicinal Chemistry. 2005. vol. 48, 3319-3327.

Hopper et al., "Facile synthesis of lysophospholipids Containing unsaturated fatty acid chains," Tetrahedron Letters, vol. 37 ( No. 44), p. 7871-7874, 1996.

Heise, C. et al., Molecular Pharmacology, 60, 1173-1180, (2001).

Ortiz, A., et al., J. Med. Chem., 38, 2681-2691, (1995): Erratum 40, 4168, (1997).

Lynch, K., et al., Molecular Pharmacology, 52, 75-81, (1997).

\* cited by examiner

○ No Inhibitor　　■ wis 31 (500 μM)　　▼ wis 60 (500 μM)

○ No Inhibitor   ■ wls 31 (500 μM)   ▼ wls 60 (500 μM)

○ No Inhibitor  ■ wls 31 (500 µM)  ▼ wls 60 (500 µM)

LYSOPHOSPHATIDIC ACID RECEPTOR SELECTIVE ANTAGONISTS

CROSS REFERENCE TO RELATED APPLICATIONS

This application is a national stage filing of International Application No. PCT/US2005/016011, filed on May 6, 2005, which is entitled to priority pursuant to 35 U.S.C. §119(e) to U.S. provisional patent application No. 60/568,520, filed on May 6, 2004 the disclosures of which are incorporated by reference herein in their entirety.

US GOVERNMENT RIGHTS

This invention was made with United States Government support under Grant Nos. NIH R01 GM52722, and R01 CA88994, awarded by National Institutes of Health. The United States Government has certain rights in the invention.

BACKGROUND

Lysophosphatidic acid (LPA, 1-acyl, 2-hydroxyl-sn-glycerol-3-phosphate) is an intermediary metabolite in all cells but is released from some cells to act as a mediator that elicits a wide variety of responses from cells/tissues. These responses include calcium mobilization, cytoskeletal rearrangements, mitogenesis and anti-apoptotic (survival) activity. For example, LPA is released by activated platelets and accumulates in serum to low micromolar levels, where it is a prominent growth factor for many cell types. LPA has also been found in ascitic fluid from ovarian cancer patients where it promotes mitogenesis of ovarian tumor cells. Interestingly, the LPA found in serum vs. ascitic fluid differs in that LPA from ascitic fluid is reportedly enriched in 2-acyl LPA species. Study of this 2-acyl LPA isoform is made difficult however by its chemical instability, i.e., the rapid migration of the acyl chain to the thermodynamically favored 1 position in an aqueous environment. Transient rises in blood pressure in rats and guinea pigs has also been documented following intravenous LPA injection. The induction of platelet aggregation and fibroblast recruitment along with its mitogenic capabilities implicate this lipid as a wound healing hormone.

LPA signals cells in part via a set of G protein-coupled receptors named LPA1, LPA2, and LPA3 (formerly Edg-2, Edg-4 and Edg-7). These receptors share 50-55% identical amino acids and cluster with five other receptors (S1P1, S1P2, S1P3, S1P4, S1P5 (formerly Edg-1, Edg-5, Edg-3, Edg-6, Edg-8) for the structurally-related lipid sphingosine 1-phosphate (S1P). LPA1 is most associated with activation of Giα pathways and is expressed in oligodendrocytes and peripheral tissues while LPA2 and LPA3 are associated most prominently with Gq/11α pathways. LPA2 mRNA is found in testis and peripheral blood leukocytes while LPA3 mRNA has been localized to prostate, testes, pancreas, kidney, and heart.

The physiologic implications of occupation of individual LPA receptors are largely unknown due in part to a lack of receptor type selective ligands. Therefore there is a need for compounds that have strong affinity and high selectivity for LPA receptors. The present invention is directed to a series of 2-substituted ethanolamide derivatives that vary in degrees of size, hydrophobicity, and stereochemistry. The parent compound of the claimed series, N-acyl ethanolamide phosphate (NAEPA) has been shown to be nearly indistinguishable from LPA in evoking platelet aggregation and GTP[γ35 S] binding at LPA1 and LPA2 containing membranes but is distinctly less active than LPA at recombinant LPA3 or in depolarizing *Xenopus* oocytes.

Three 2-substituted NAEPA compounds have already been reported. A 2-carboxyl-containing compound (named 'NASPA' for N-palmitoyl serine phosphate) has been documented to antagonize both LPA-driven platelet aggregation (Sugiura et al., 1994 *Arch Biochem Biophys* 311: 358-368) and oocyte depolarization (Santos et al., 2000 *NYAS Meeting Report*; Annals New York Academy of Sciences p 232-241) and is a partial agonist at mammalian LPA receptors. A 2-methylene hydroxy-containing compound, which is an analog of 2-acyl LPA wherein the ester is replaced by an amide, has been reported as activating recombinant LPA receptors in a stereoselective fashion while mitogenic responses and platelet aggregation did not show this stereoselectivity. Finally, a third compound (named 'PNPA' for N-palmitoyl-norleucinol-1-phosphate) has n-butyl located at the 2 position. This compound aggregates human platelets without regard to stereoselectivity. The present invention is directed to a series of prodrug derivatives of compounds active at LPA receptors.

SUMMARY OF VARIOUS EMBODIMENTS OF THE INVENTION

The present invention is directed to a series of LPA analogs wherein the glycerol is replaced with ethanolamine N-acyl ethanolamide phosphate, N-acyl EPA) as a lead structure. This group of novel compounds, having a variety of substitutions at the second carbon atom of the lead compound, were synthesized and tested for activity at the LPA receptors. LPA analogs were prepared and found to have a range of activities including antagonism, with various degrees of selectivity at individual LPA receptors, as well as compounds with agonist activity at the LPA receptors. In one embodiment the present invention include compounds with the general structure:

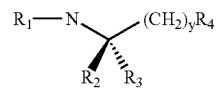

wherein $R_1$ is a large lipophilic group, $R_2$ and $R_3$ are independently selected from the group consisting of H, $C_1$-$C_6$ alkyl, and

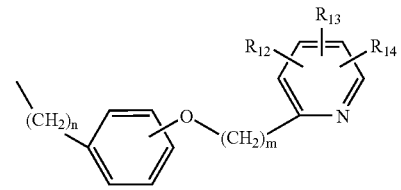

wherein n and m are independently 0-5; $R_{12}$, $R_{13}$ and $R_{14}$ are independently selected from H, $NH_2$, OH, halo, $C_1$-$C_6$ alkyl, $C_1$-$C_6$ haloalkyl and $C_1$-$C_6$ alkoxy, y is an integer from 1-4, and $R_4$ is selected from the group consisting of hydroxy, phosphate, phosphonate, α-substituted phosphonate, phosphate analogs and phosphonate analogs. Selective agonists and antagonists at LPA receptors will be useful therapeutically in a wide variety of human disorders.

Columns 1-13 represent the administration of VPC12086, VPC12101, VPC12109, VPC2115, VPC12098, VPC12105, VPC12084, VPC12255, VPC31144, VPC31143, VPC31180, VPC31139 and LPA, respectively. 100% calcium indicates the signal observed after permeabilization with digitonin. Bars are representative of three experiments.

Figure 1:
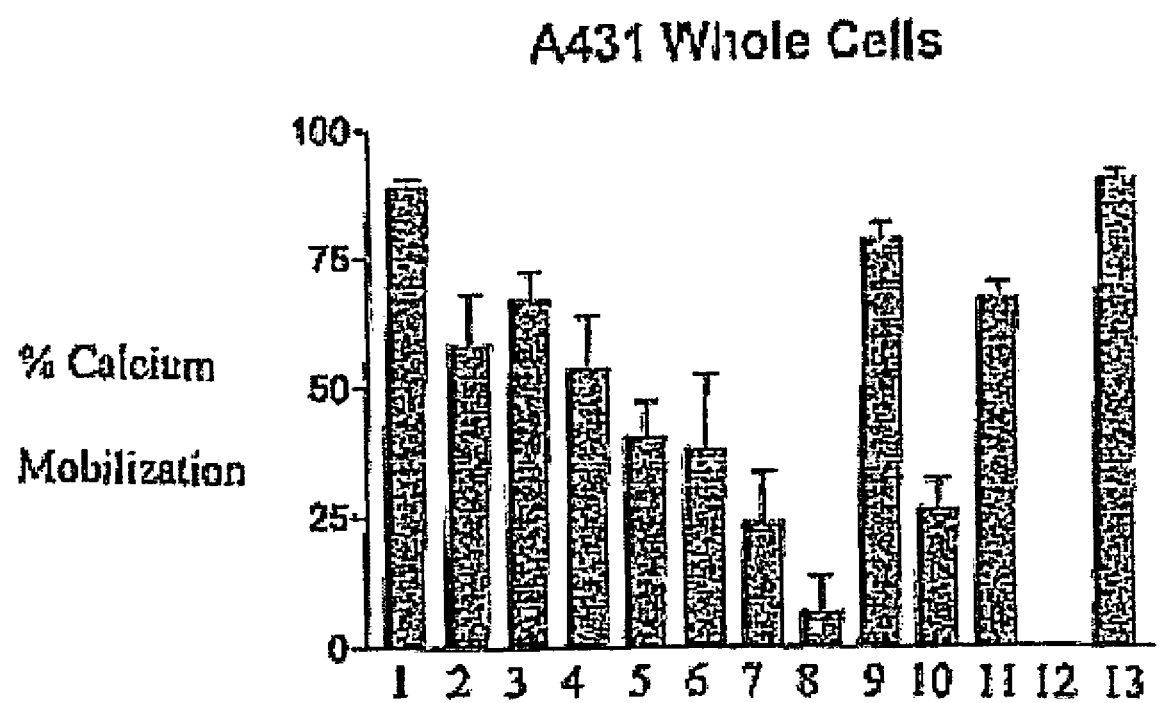
FIG. 1 is a graphic representation of the calcium mobilization in A431 cells treated with 10 μM of each compound.
Figure 2A:
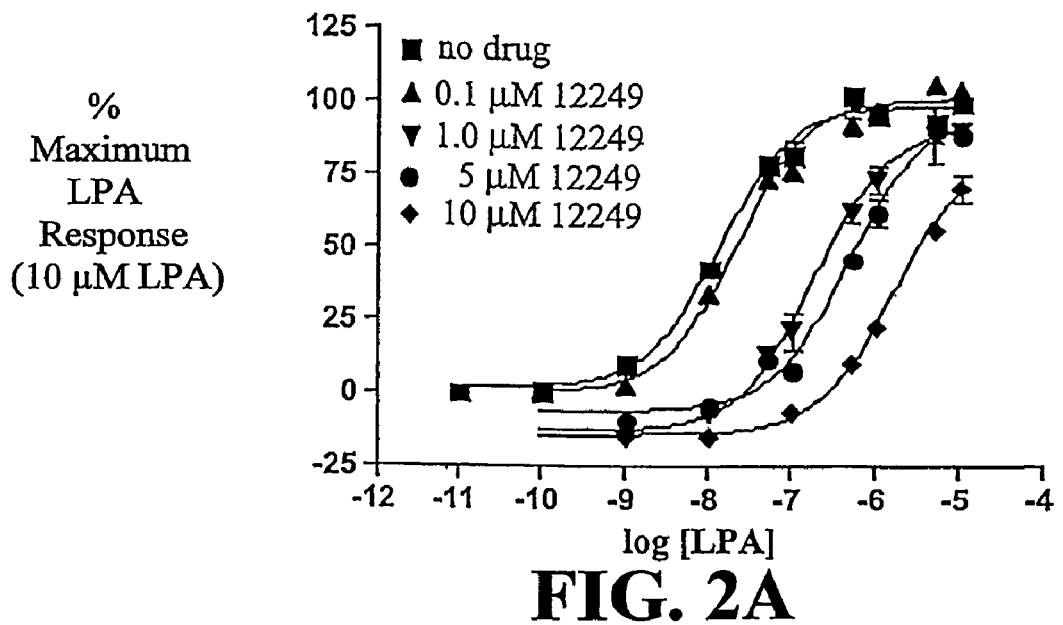
Figure 2B:
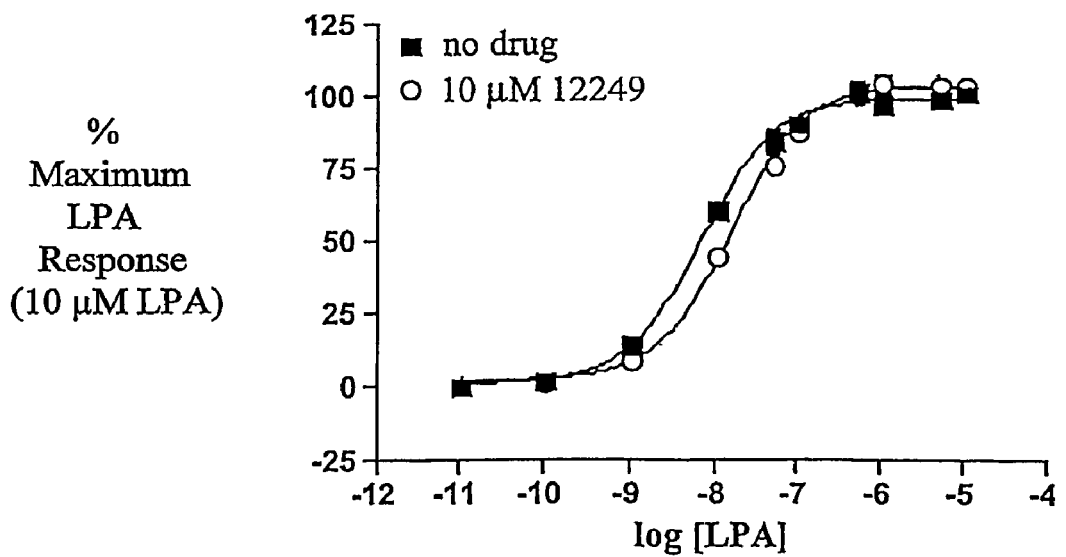
Figure 2C:
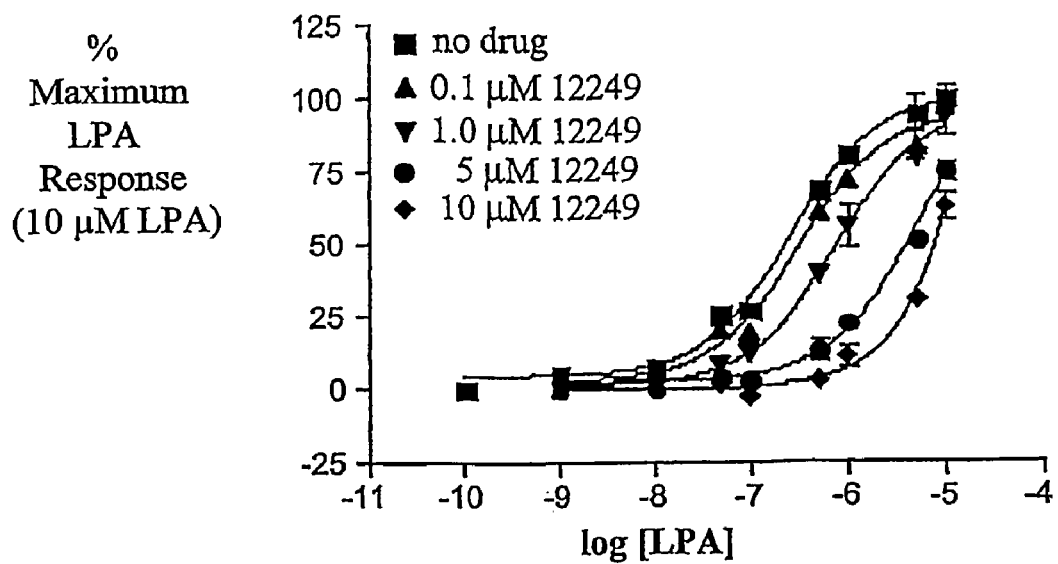
Figure 2D:
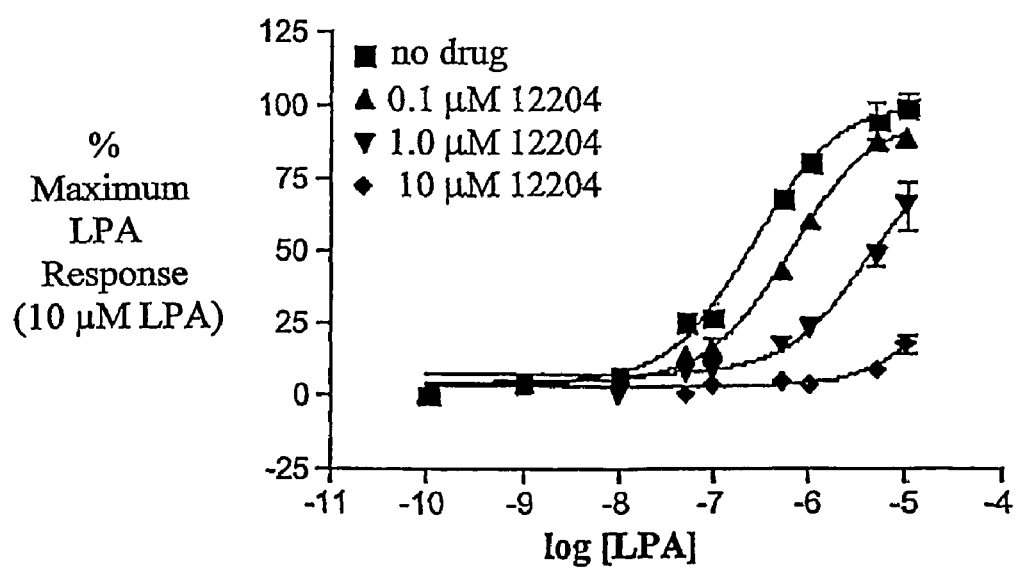

FIG. 2A-2D are graphic representations of the effect of VPC12249 and VPC12204 on GTP[$\gamma^{35}$S] binding. GTP [$\gamma^{35}$S] binding assays of LPA1 (FIG. 2A), LPA2 (FIG. 2B), and LPA3 (FIG. 2C) transfected HEK293T cell membranes showing LPA concentration response curves with increasing concentrations of VPC12249. FIG. 2D shows the effect of VPC12204 (enantiomer of VPC12249) on GTP[$\gamma^{35}$S] binding at LP3 transfected HEK293T cell membranes. Points are in triplicate and are representative of at least two experiments.

Figure 3A:
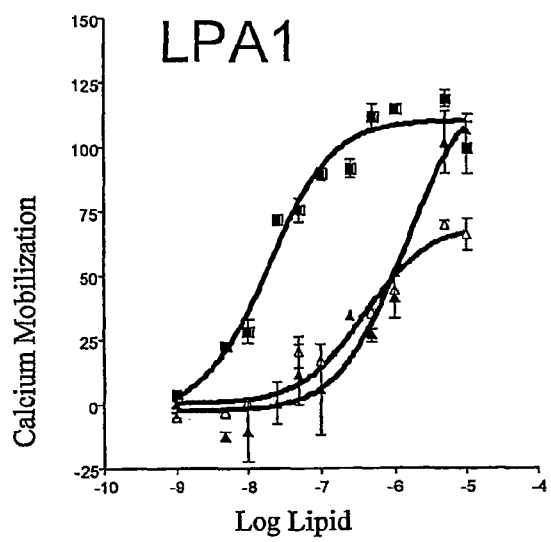
Figure 3B:
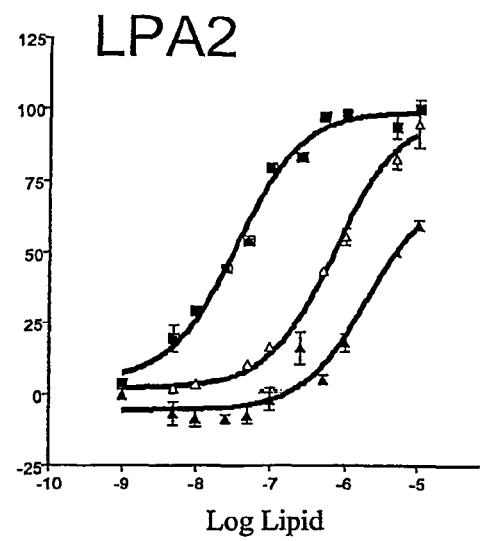
Figure 3C:
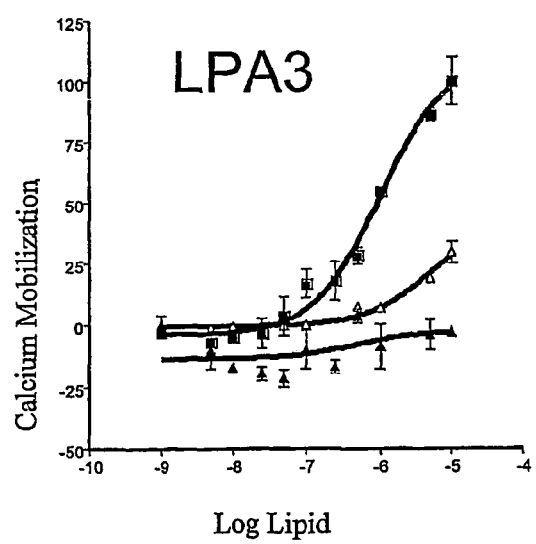

FIG. 3 illustrates dose-response curves for LPA, VPC12031 and VPC12060 stimulation of GTP$\gamma$[$^{35}$S] in Rh7777 of HEK293T membranes at LPA1, LPA2, and LPA3 receptors. FIG. 3A represents stimulation of GTP$\gamma$[$^{35}$S] binding to LPA1 in Rh7777 membranes; FIG. 3B represents stimulation of GTP$\gamma$[$^{35}$S] binding to LPA2 in HEK293T membranes; FIG. 3C represents stimulation of GTP$\gamma$[$^{35}$S] binding to LPA3 in HEK293T membranes.

Figure 4A:
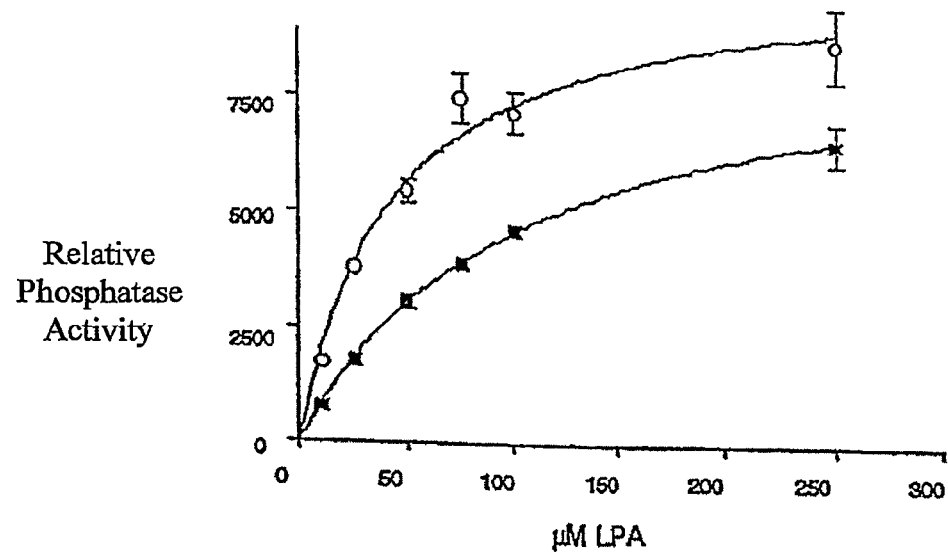
Figure 4B:
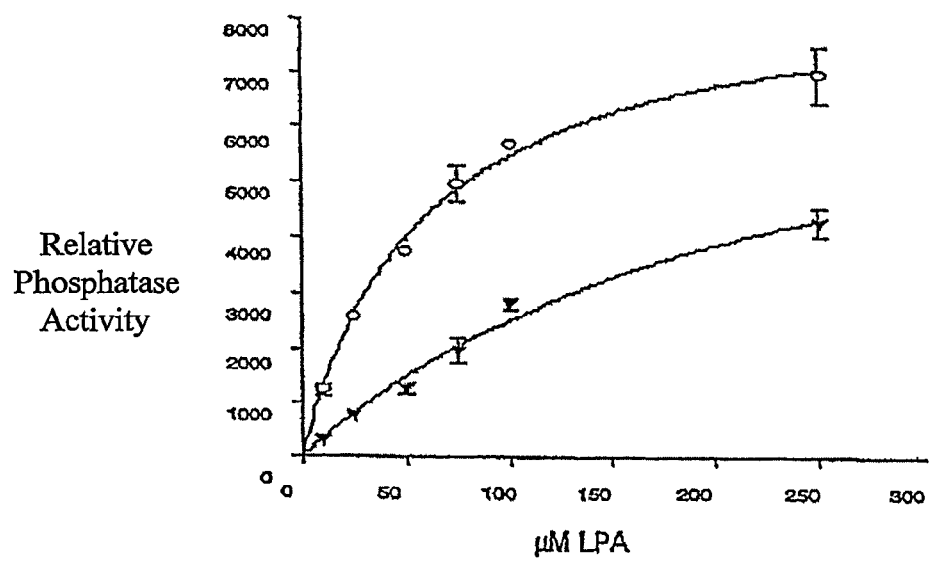

FIGS. 4A and 4B illustrate the inhibitory activity of NOHPP (VPC12031) and alpha keto NOHPP analog (VPC12060), respectively, at the LPP1 (PAP2a) phosphatase.

Figure 5A:
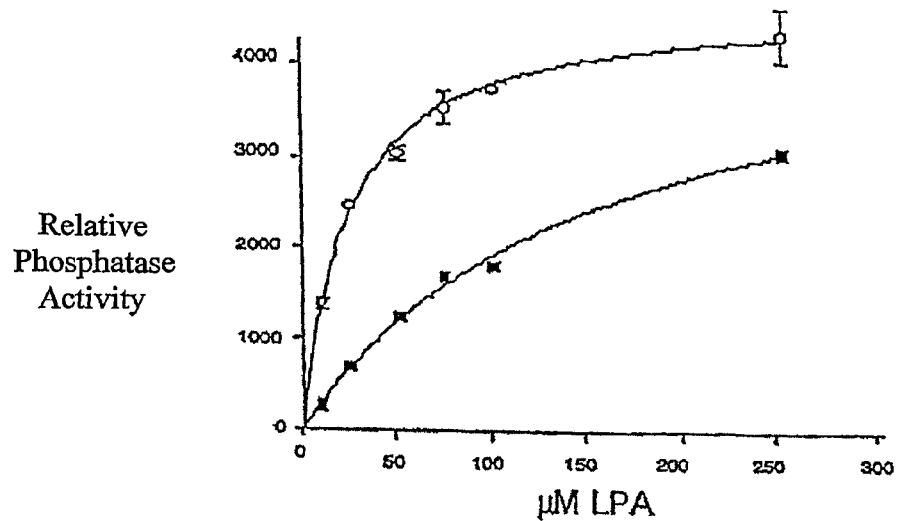
Figure 5B:
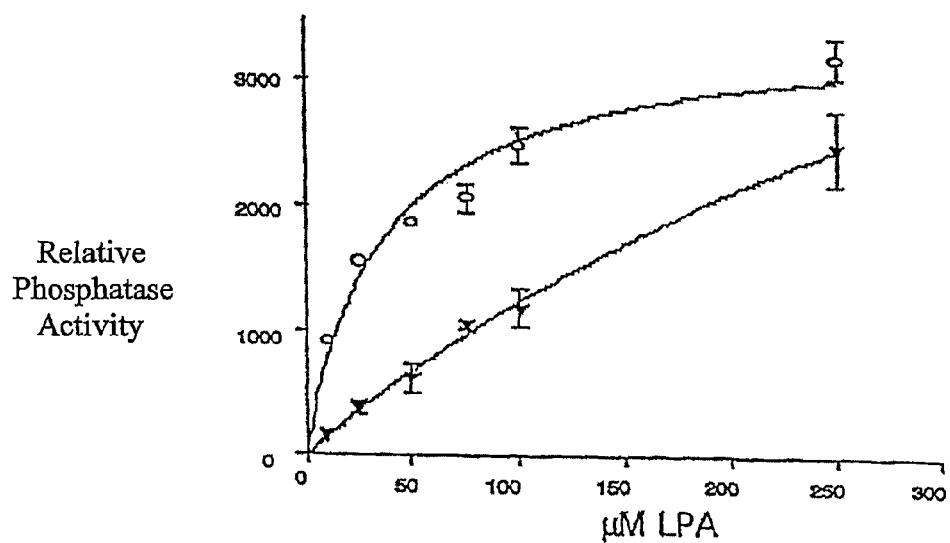

FIGS. 5A and 5B illustrate the inhibitory activity of NOHPP (VPC12031) and alpha keto NOHPP analog (VPC12060), respectively, at the LPP2 (PAP3a) phosphatase.

Figure 6A:
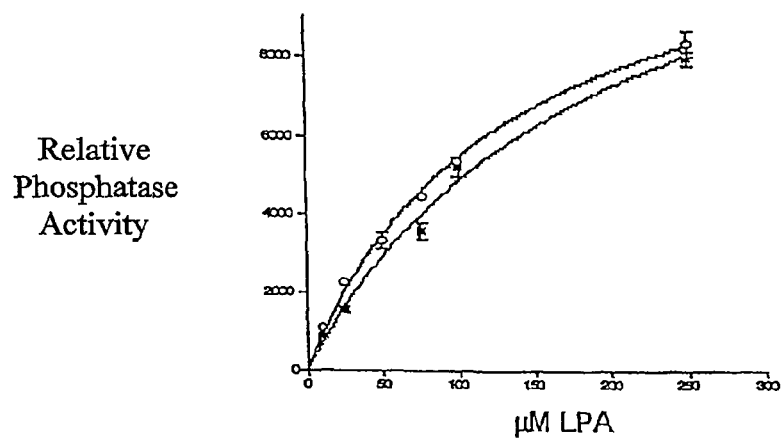
Figure 6B:
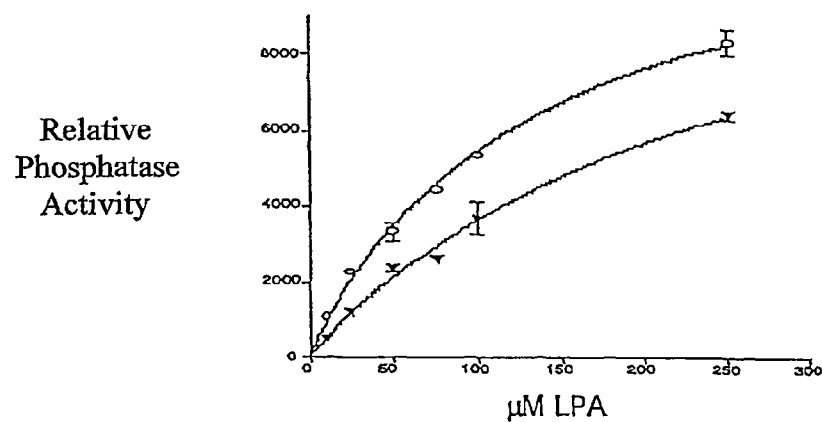

FIGS. 6A and 6B illustrate the inhibitory activity of NOHPP (VPC12031) and alpha keto NOHPP analog (VPC12060), respectively, at the LPP3 (PAP2b) phosphatase.

Figure 7:
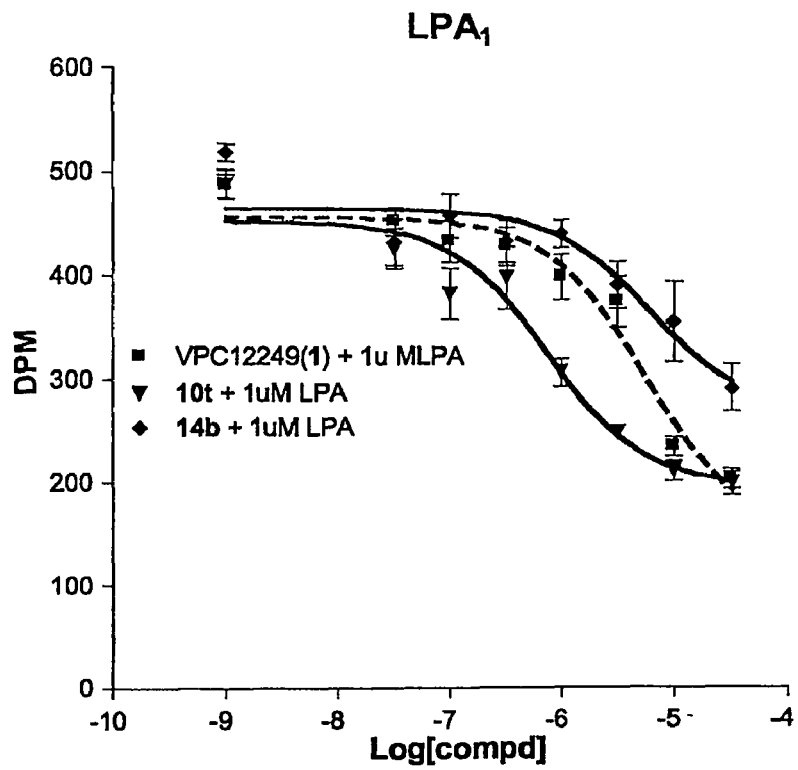

FIG. 7 illustrates dose-response curves for VPC12249, and derivative compounds 35t and 39b, stimulation of GTP$\gamma$[$^{35}$S] in Rh7777 of HEK293T membranes at LPA1 receptors.

Figure 8:
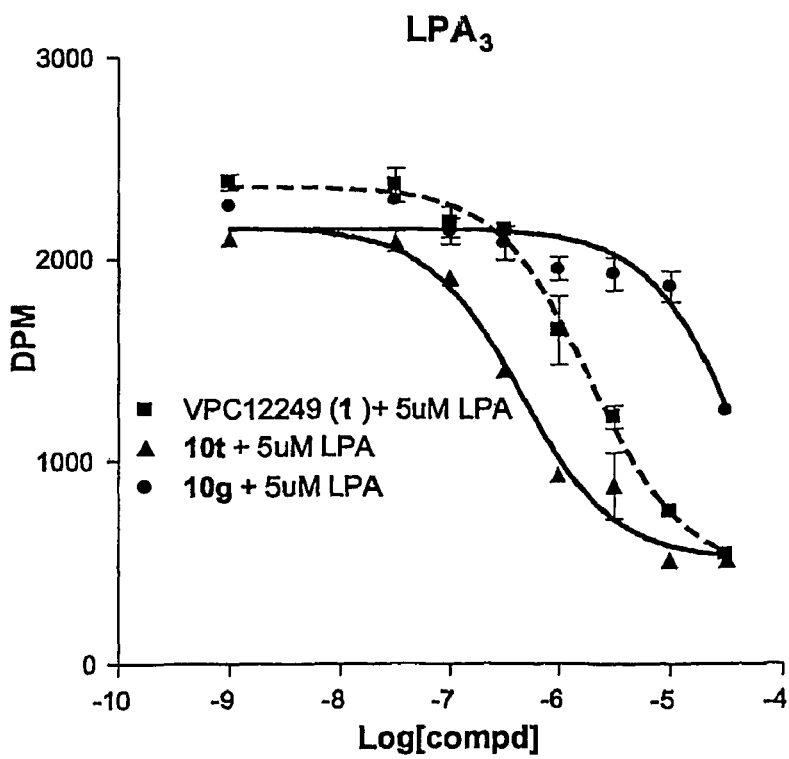

FIG. 8 illustrates dose-response curves for VPC12249, and derivative compounds 35t and 35g, stimulation of GTP$\gamma$[$^{35}$S] in Rh7777 of HEK293T membranes at LPA3 receptors.

Figure 9:
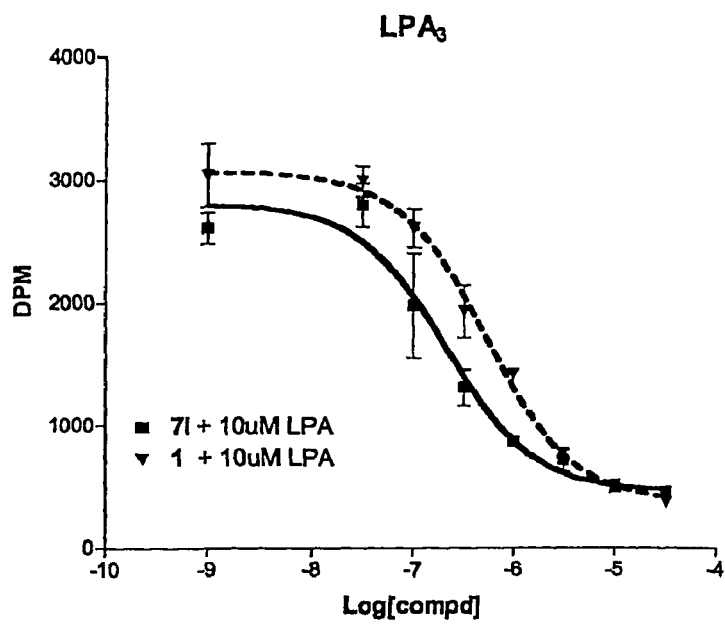

FIG. 9 illustrates dose-response curves for 26a, 63d and 63f, stimulation of GTP$\gamma$[$^{35}$S] in Rh7777 of HEK293T membranes at LPA1 receptors.

Figure 10:
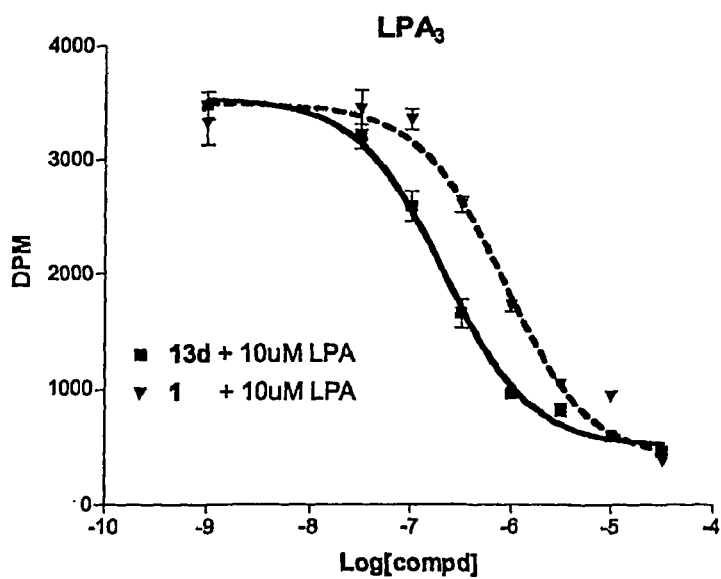

FIG. 10 illustrates dose-response curves for compounds 26a and 571, stimulation of GTP$\gamma$[$^{35}$S] in Rh7777 of HEK293T membranes at LPA3 receptors.

Figure 11:
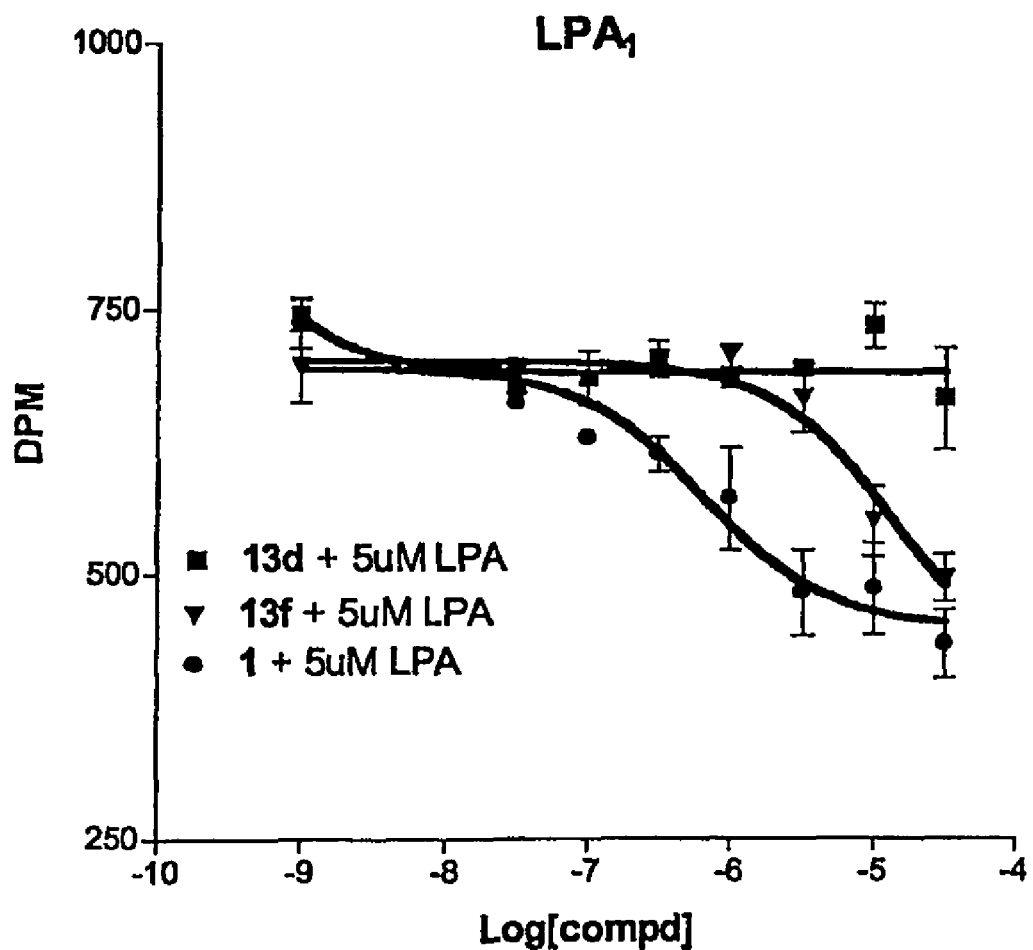

FIG. 11 illustrates dose-response curves for compounds 26a and 63d, stimulation of GTP$\gamma$[$^{35}$S] in Rh7777 of HEK293T membranes at LPA3 receptors.

DETAILED DESCRIPTION OF THE INVENTION

Definitions

In describing and claiming the invention, the following terminology will be used in accordance with the definitions set forth below.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes prophylaxis of the specific disorder or condition, or alleviation of the symptoms associated with a specific disorder or condition and/or preventing or eliminating said symptoms.

As used herein, an "effective amount" means an amount sufficient to produce a selected effect. For example, an effective amount of an S1P receptor antagonist is an amount that decreases the cell signaling activity of the S1P receptor.

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically $C_1$-$C_6$ alkyl groups include, but are not limited to, methyl, ethyl, n-propyl, iso-propyl, butyl, iso-butyl, sec-butyl, tert-butyl, pentyl, hexyl and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" refers to from zero to four substituents, wherein the substituents are each independently selected. Each of the independently selected substituents may be the same or different than other substituents.

As used herein the term "aryl" refers to a mono- or bicyclic carbocyclic ring system having one or two aromatic rings including, but not limited to, phenyl, benzyl, naphthyl, tetrahydronaphthyl, indanyl, indenyl, and the like. "Optionally substituted aryl" includes aryl compounds having from zero to four substituents, and "substituted aryl" includes aryl compounds having one to three substituents, wherein the substituents, including alkyl, halo or amino substituents. The term ($C_5$-$C_8$ alkyl)aryl refers to any aryl group which is attached to the parent moiety via the alkyl group.

The term "heterocyclic group" refers to a mono- or bicyclic carbocyclic ring system containing from one to three heteroatoms wherein the heteroatoms are selected from the group consisting of oxygen, sulfur, and nitrogen.

As used herein the term "heteroaryl" refers to a mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "lower alkyl" as used herein refers to branched or straight chain alkyl groups comprising one to eight carbon atoms, including methyl, ethyl, propyl, isopropyl, n-butyl, t-butyl, neopentyl and the like.

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

As used herein, an "effective amount" means an amount sufficient to produce a selected effect. For example, an effective amount of an LPA receptor antagonist is an amount that decreases the cell signaling activity of the LPA receptor.

As used herein, an "LPA modulating agent" refers a compound or composition that is capable of inducing a detectable change in LPA receptor activity in vivo or in vitro (e.g., at least 10% increase or decrease in LPA activity as measured by a given assay such as the bioassay described in Example 2).

As used herein, the term "$EC_{50}$ of an agent" refers to that concentration of an agent at which a given activity, including binding of sphingosine or other ligand of an S1P receptor and/or a functional activity of a S1P receptor (e.g., a signaling activity), is 50% maximal for that S1P receptor. Stated differently, the $EC_{50}$ is the concentration of agent that gives 50% activation, when 100% activation is set at the amount of activity of the S1P receptor which does not increase with the addition of more ligand/agonist and 0% is set at the amount of activity in the assay in the absence of added ligand/agonist.

As used herein, the term "phosphate analog" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., H, $NH_4$, Na, and the like if such counterions are present.

The LPA analogs of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

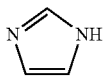

is understood to represent a mixture of the structures:

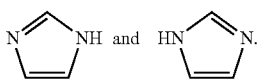

The term "pharmaceutically-acceptable salt" refers to salts which retain the biological effectiveness and properties of the S1P analogs of the present invention and which are not biologically or otherwise undesirable. In many cases, the S1P analogs of the present invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted allyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amities, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Embodiments

Lysophosphatidic acid (LPA) elicits a wide variety of responses from cells and tissues including calcium mobilization, changes in cell shape and motility, mitogenesis and anti-apoptosis. These effects are mediated by at least three LPA receptors (LPA1, LPA2 and LPA3) that have been cloned. Assignment of a physiological response to stimulation of a particular LPA receptor(s) is made difficult by lack of ligands that discriminate amongst receptor subtypes. The problem is exacerbated by the existence of at least three lyso-lipid phosphate phosphatases (LPPs) that act as ecto-phosphatases in degrading extra-cellular LPA as well as the potential for LPA to be acylated by LPA acyl transferases to yield another mediator, phosphatidic acid. Therefore, the discovery of new chemical entities that are (1) LPA receptor subtype selective agonists or antagonist and/or (2) LPA receptor agonists that are resistant to enzymatic degradation and/or (3) inhibitors of the LPPs is highly desirable.

One embodiment of the present invention is directed to improved derivatives of LPA analogs, wherein the compounds have been modified to enhance their oral availability and thus increase their efficacy as orally administered pharmaceuticals. The LPA analogs of the present invention modulate LPA receptor function through a variety of different mechanisms including their functioning as a receptor antagonist, receptor agonist (full or partial), or as inhibitors of LPA phosphotases or synthetic enzymes such as sphingosine kinase or autotoxin. One aspect of the present invention is directed to prodrug derivatives of LPA analogs, wherein the LPA analogs are prepared as phospho-ester derivatives that have enhanced oral availability relative to the parent compound. After the compounds are absorbed from the alimentary canal of the animal being administered the compound, the phospho-ester is cleaved to regenerate the active form of the compound.

A GTP[γ35 S] binding assay was developed to analyze directly the activation of individual LPA receptors, and thus allow the identification of LPA receptor agonists and antagonists as well as determine the relative efficacies and potencies at each receptor in a common system. The same results were obtained regardless of whether the recombinant receptor used exogenous G proteins (HEK293T cells) or endogenous G proteins (RH7777 cells) and further, the activities measured in the broken cell assay predicted the responses seen in whole cell assays. Thus the primary assay used in the present invention for compound potency and efficacy is a valid measure of activity at LPA/Edg receptors.

Starting with an LPA analog wherein the glycerol is replaced with ethanolamine (N-acyl ethanolamide phosphate, N-acyl EPA) as a lead structure a series of new chemical entities with a variety of substitutions at the second carbon atom were synthesized and tested for activity at the LPA receptors. In particular, both the relative potency and efficacy of the 2-substituted N-acyl EPA compounds were measured. The 2-substituted N-acyl EPA compounds of the present invention include compounds having the general structure: an LPA analog

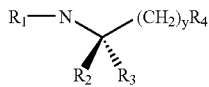
I wherein $R_1$ is selected from the group consisting of $C_8$-$C_{22}$ alkyl, $C_8$-$C_{22}$ alkenyl, $C_8$-$C_{22}$ alkanoyl, $C_8$-$C_{22}$ alkenoyl,

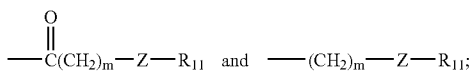

wherein m is 0-20;

Z is selected from the group consisting of $C_3$-$C_{10}$ cycloalkyl, $C_3$-$C_{15}$ bicycloalkyl, $C_5$-$C_{10}$ heterocyclic and aryl;

$R_{11}$ is selected from the group consisting of $C_1$-$C_{10}$ alkyl, $C_1$-$C_{20}$ alkoxyl, $C_1$-$C_{20}$ alkylthio, and $C_1$-$C_{20}$ alkylamino;

$R_2$ and $R_3$ are independently selected from the group consisting of H, $C_1$-$C_6$ alkyl, $C_2$-$C_4$ alkenyl, $C_2$-$C_4$ alkynyl, —($C_1$-$C_4$ alkyl)OH, —($C_1$-$C_4$ alkyl)NH$_2$, —COOR$_5$, —($C_1$-$C_4$ alkyl)COOR$_5$, —($C_1$-$C_{10}$ alkyl)aryl, $C_3$-$C_8$ cycloalkyl, $C_3$-$C_8$ heterocyclic, $C_7$-$C_{12}$ bicyclic, ($C_5$-$C_8$ alkyl)aryl, ($C_5$-$C_8$ alkenyl)aryl, ($C_5$-$C_8$ alkynyl)aryl, and

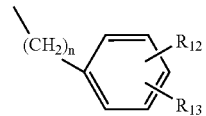

wherein n is 0-10;

$R_5$ is selected from the group consisting of H and $C_1$-$C_4$ alkyl;

$R_{12}$ is selected from the group consisting of halo, $C_1$-$C_{10}$ alkyl, ($C_0$-$C_{12}$ alkyl)aryl, ($C_2$-$C_{12}$ alkenyl)aryl, ($C_2$-$C_{12}$ alkynyl)aryl, —($C_1$-$C_4$ alkyl)OH, —($C_2$-$C_{12}$ alkenyl)OH, SR$_6$, SOR$_6$, NHR$_6$ and OR$_6$;

$R_{13}$ is selected from the group consisting of H, halo, $C_1$-$C_{10}$ alkyl, ($C_0$-$C_{12}$ alkyl)aryl, ($C_2$-$C_{12}$ alkenyl)aryl, ($C_2$-$C_{12}$ alkynyl)aryl, —($C_1$-$C_4$ alkyl)OH, —($C_2$-$C_{12}$ alkenyl)OH, SR$_6$, SOR$_6$, NHR$_6$ and OR$_6$;

wherein $R_6$ is selected from the group consisting of $C_1$-$C_{16}$ alkyl, $C_2$-$C_{16}$ alkenyl, $C_2$-$C_{16}$ alkynyl, —($C_1$-$C_4$ alkyl)R$_7$, —($C_2$-$C_4$ alkenyl)R$_7$, —($C_1$-$C_4$ carboxy)R$_7$ and —($C_2$-$C_4$ alkynyl)R$_7$; and $R_7$ is selected from the group consisting of optionally substituted $C_3$-$C_8$ cycloalkyl, optionally substituted $C_3$-$C_8$ heterocyclic, optionally substituted $C_7$-$C_{12}$ bicyclic and optionally substituted $C_5$-$C_8$ cycloalkenyl, optionally $C_5$-$C_8$ substituted aryl and optionally substituted $C_5$-$C_8$ heteroaryl, wherein the ring structures are substituted with one or more substituents selected from the group of $C_1$-$C_6$ alkyl, $C_2$-$C_6$ alkenyl, $C_1$-$C_6$ alkoxy, halo, $C_1$-$C_6$ haloalkyl, $C_1$-$C_6$ haloalkoxy, amino or hydroxy groups;

y is 0-4; and $R_4$ is selected from the group consisting of hydroxy and

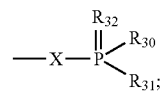

wherein $R_{32}$ is selected from the group consisting of O, NH and S;

X is selected from the group consisting of O, NH, S, CH$_2$, CHOH, CHF, CF$_2$, and

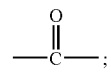

and $R_{30}$ and $R_{31}$ are independently selected from the group consisting of $C_1$-$C_2$ alkoxy, hydrogen, hydroxy,

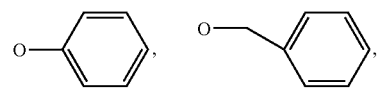

-continued

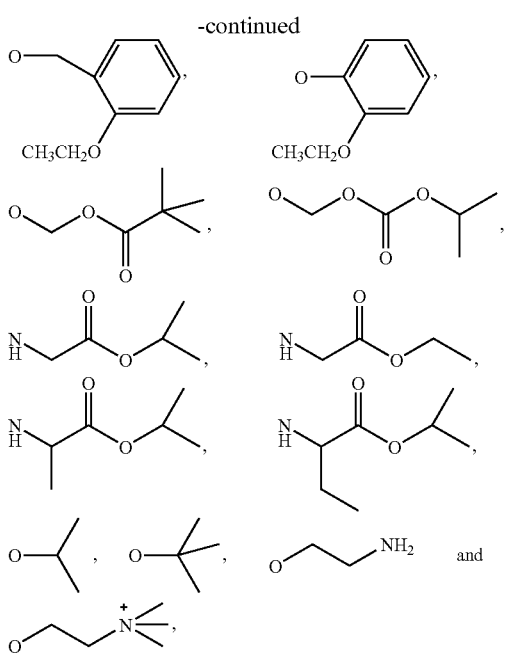

and pharmaceutically acceptable salts thereof.

In accordance with one embodiment an LPA analog of the general structure of Formula I is provided wherein $R_1$ is selected from the group consisting of $C_8$-$C_{22}$ alkyl, $C_8$-$C_{22}$ alkenyl, $C_8$-$C_{22}$ alkanoyl, $C_8$-$C_{22}$ alkenoyl,

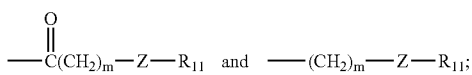

wherein m is 0-20;

Z is selected from the group consisting of $C_3$-$C_{10}$ cycloalkyl, $C_3$-$C_{15}$ bicycloalkyl, $C_5$-$C_{10}$ heterocyclic and optionally substituted $C_5$-$C_8$ aryl;

$R_{11}$ is selected from the group consisting of $C_1$-$C_{10}$ alkyl, $C_1$-$C_{20}$ alkoxyl, $C_1$-$C_{20}$ alkylthio, and $C_1$-$C_{20}$ alkylamino;

$R_2$ and $R_3$ are selected from the group consisting of H, $C_1$-$C_6$ alkyl,

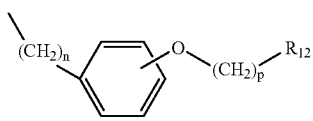

with the proviso that $R_2$ or $R_3$ is

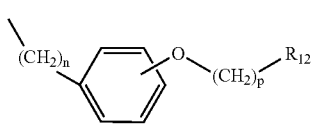

wherein $R_{12}$ is optionally substituted $C_5$-$C_8$ aryl or optionally substituted $C_5$-$C_8$ heteroaryl, wherein said substituents are selected from the group consisting of halo, $C_1$-$C_6$ alkyl, $C_1$-$C_6$ haloalkyl, $C_2$-$C_6$ alkenyl, $C_1$-$C_6$ alkoxy, $C_1$-$C_6$ haloalkoxy, —O($C_1$-$C_6$ alkyl)$C_1$-$C_6$ alkoxy and —O($C_1$-$C_6$ alkyl)$C_1$-$C_6$ haloalkoxy;

y is 1-4; n and p are independently 1-5; and $R_4$ is selected from the group consisting of hydroxy,

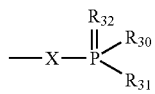

and other phosphate and phosphonate analogs;

wherein $R_{32}$ is selected from the group consisting of O, NH and S;

X is selected from the group consisting of O, NH, S, $CH_2$, CHOH, CHF, $CF_2$, and

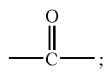

and $R_{30}$ and $R_{31}$ are independently selected from the group consisting of $C_1$-$C_2$ alkoxy, hydroxy,

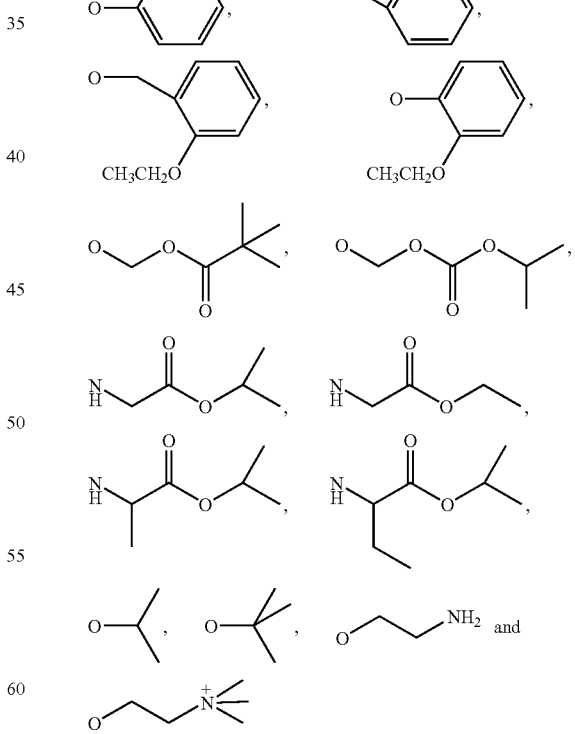

and pharmaceutically acceptable salts thereof.

In accordance with one embodiment an LPA analog of the present invention is provided represented by the formula:

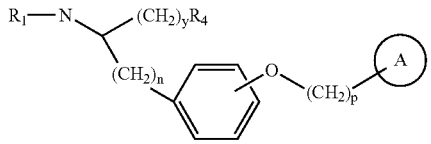

wherein $R_1$ is selected from the group consisting of $C_8$-$C_{22}$ alkyl, $C_8$-$C_{22}$ alkenyl, $C_8$-$C_{22}$ alkanoyl, $C_8$-$C_{22}$ alkenoyl,

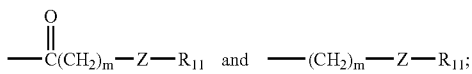

wherein m is 0-20;

Z is selected from the group consisting of $C_4$-$C_8$ cycloalkyl, $C_5$-$C_8$ heterocyclic and $C_5$-$C_8$ aryl;

$R_{11}$ is selected from the group consisting of $C_1$-$C_{10}$ alkyl, $C_1$-$C_{20}$ alkoxyl, $C_1$-$C_{20}$ alkylthio, and $C_1$-$C_{20}$ alkylamino;

y is 1-4; n and p are independently 1-5;

$R_4$ is selected from the group consisting of hydroxy, and

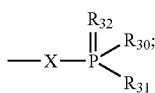

wherein $R_{32}$ is selected from the group consisting of O, NH and S;

X is selected from the group consisting of O, NH, S, $CH_2$, CHOH, CHF, $CF_2$, and

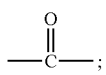

and $R_{30}$ and $R_{31}$ are independently selected from the group consisting of $C_1$-$C_2$ alkoxy, hydroxy,

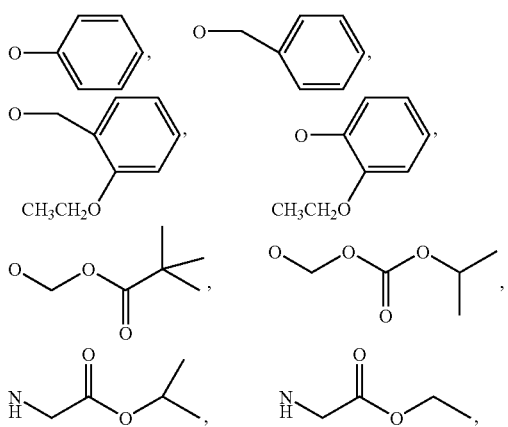

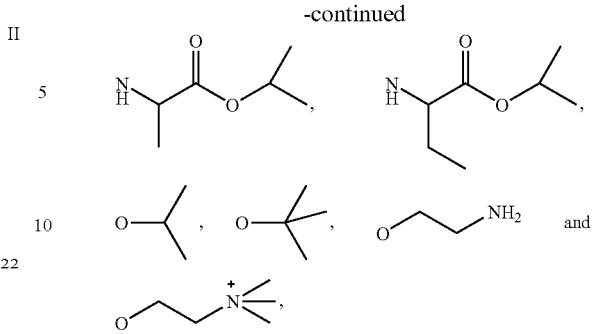

wherein

is a heterocyclic substituent selected from the group consisting of

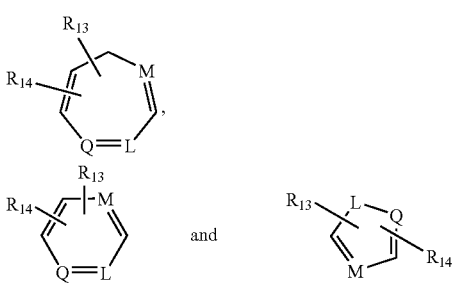

wherein L, M, and Q are independently selected from the group consisting of N, $NR_{15}$, O, S, $CHR_{15}$ and $CR_{15}R_{16}$;

$R_{13}$, $R_{14}$, $R_{15}$ and $R_{16}$ are independently selected from the group consisting of H, halo, $C_1$-$C_6$ alkyl, $C_1$-$C_6$ haloalkyl, $C_2$-$C_6$ alkenyl, $C_1$-$C_6$ alkoxy, $C_1$-$C_6$ haloalkoxy, —O($C_1$-$C_6$ alkyl)$C_1$-$C_6$ alkoxy and —O($C_1$-$C_6$ alkyl)$C_1$-$C_6$ haloalkoxy; and pharmaceutically acceptable salts thereof. In another embodiment, a compound of Formula II is provided wherein $R_1$ is selected from the group consisting of $C_8$-$C_{22}$ alkyl, $C_8$-$C_{22}$ alkenyl, $C_8$-$C_{22}$ alkanoyl, $C_8$-$C_{22}$ alkenoyl,

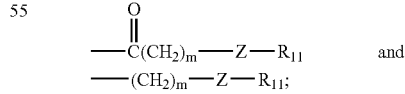

wherein m is 0-20;

Z is selected from the group consisting of $C_4$-$C_8$ cycloalkyl, $C_5$-$C_8$ heterocyclic and $C_5$-$C_8$ aryl;

$R_{11}$ is selected from the group consisting of $C_1$-$C_{10}$ alkyl, $C_1$-$C_{20}$ alkoxyl, $C_1$-$C_{20}$ alkylthio, and $C_1$-$C_{20}$ alkylamino;

y, n and p are each 1;

$R_4$ is selected from the group consisting of hydroxy, and

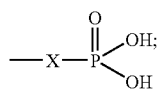

wherein X is selected from the group consisting of $CH_2$, CHOH, CHF, $CF_2$, and

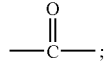

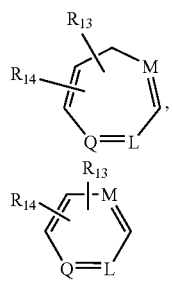

is a heterocyclic substituent selected from the group consisting of wherein L, M, and Q are independently selected from the group consisting of N, $NR_{15}$, O, S, $CHR_{15}$ and $CR_{15}R_{16}$;

$R_{13}$, $R_{14}$, $R_{15}$ and $R_{16}$ are independently selected from the group consisting of H, halo, $C_1$-$C_6$ alkyl, $C_1$-$C_6$ haloalkyl, $C_1$-$C_6$ alkoxy and $C_1$-$C_6$ haloalkoxy; and pharmaceutically acceptable salts thereof.

In another embodiment, a compound of the general structure

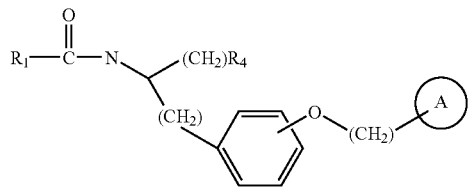

is provided wherein $R_1$ is selected from the group consisting of $C_8$-$C_{22}$ alkyl, $C_8$-$C_{22}$ alkenyl $R_4$ is selected from the group consisting of hydroxy, and

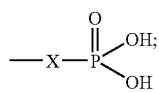

wherein X is selected from the group consisting of $CH_2$, CHOH, CHF, $CF_2$, and

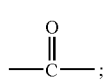

is a heterocyclic substituent selected from the group consisting of

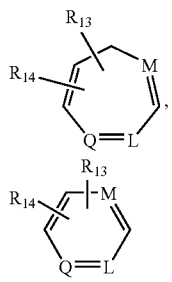
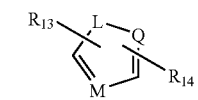

wherein L, M, and Q are independently selected from the group consisting of N, $NR_{15}$, O, S, $CHR_{15}$ and $CR_{15}R_{16}$;

$R_{13}$, $R_{14}$, $R_{15}$ and $R_{16}$ are independently selected from the group consisting of H, halo, $C_1$-$C_6$ alkyl, $C_1$-$C_6$ haloalkyl and $C_1$-$C_6$ alkoxy; and pharmaceutically acceptable salts thereof.

In another embodiment an LPA analog of formula II is provided wherein $R_1$ is selected from the group consisting of $C_8$-$C_{22}$ alkyl, $C_8$-$C_{22}$ alkenyl, $C_8$-$C_{22}$ alkanoyl, $C_8$-$C_{22}$ alkenoyl,

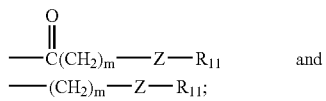

wherein m is 0-20;

Z is selected from the group consisting of $C_4$-$C_8$ cycloalkyl, $C_5$-$C_8$ heterocyclic and $C_5$-$C_8$ aryl;

$R_{11}$ is selected from the group consisting of $C_1$-$C_{10}$ alkyl, $C_1$-$C_{20}$ alkoxyl, $C_1$-$C_{20}$ alkylthio, and $C_1$-$C_{20}$ alkylamino;

y, n and p are each 1;

$R_4$ is selected from the group consisting of hydroxy, and

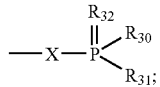

wherein $R_{32}$ is selected from the group consisting of O, NH and S;

X is selected from the group consisting of O, NH, S, $CH_2$, CHOH, CHF, $CF_2$, and

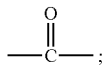

and $R_{30}$ and $R_{31}$ are independently selected from the group consisting of $C_1$-$C_2$ alkoxy, hydroxy,

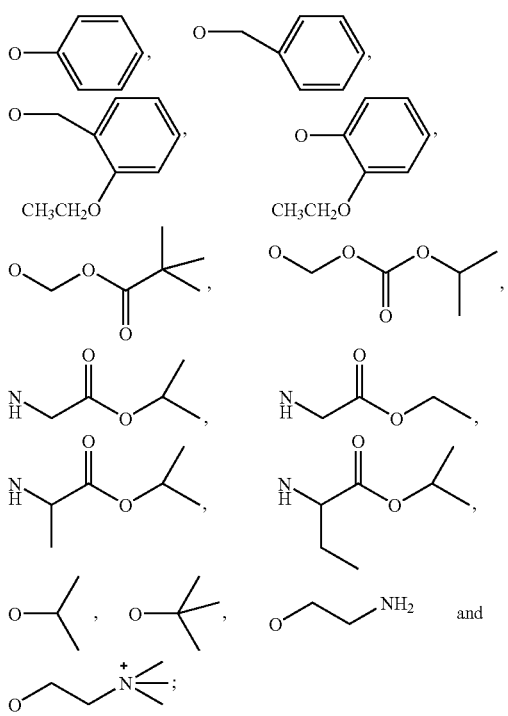

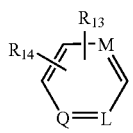

is a heterocyclic substituent represented by the formula

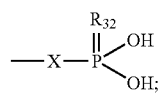

wherein L, M, and Q are independently selected from the group consisting of N, O, S and $CHR_{15}$;

$R_{13}$, $R_{14}$ and $R_{15}$ are independently selected from the group consisting of H, halo, $C_1$-$C_6$ alkyl, $C_1$-$C_6$ haloalkyl, $C_1$-$C_6$ alkoxy and $C_1$-$C_6$ haloalkoxy; and pharmaceutically acceptable salts thereof.

In a further embodiment of the present invention an LPA antagonist is provided wherein the antagonist is represented by the formula:

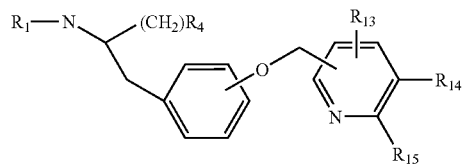

wherein $R_1$ is selected from the group consisting of $C_8$-$C_{22}$ alkyl, $C_8$-$C_{22}$ alkenyl, $C_9$-$C_{22}$ alkanoyl, $C_8$-$C_{22}$ alkenoyl, $R_4$ is selected from the group consisting of hydroxy, and

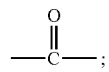

wherein $R_{32}$ is selected from the group consisting of O, NH and S;

X is selected from the group consisting of O, NH, S, $CH_2$, CHOH, CHF, $CF_2$, and

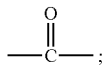

$R_{13}$, $R_{14}$ and $R_{15}$ are independently selected from the group consisting of H, halo, $C_1$-$C_6$ alkyl, $C_1$-$C_6$ haloalkyl, $C_1$-$C_6$ alkoxy and $C_1$-$C_6$ haloalkoxy; and pharmaceutically acceptable salts thereof.

Surprisingly, applicants have found that certain phosphonate LPA derivatives have enhanced affinity for the $LPA_3$ receptor relative to the other LPA subtypes. Accordingly, compositions comprising these LPA derivatives can be used to specifically block $LPA_3$ receptor activity. $LPA_3$ receptor specific antagonists include compounds of the structure:

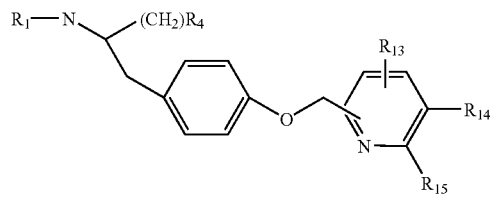

wherein $R_1$ is selected from the group consisting of $C_8$-$C_{22}$ alkyl, $C_8$-$C_{22}$ alkenyl, $C_8$-$C_{22}$ alkanoyl, $C_8$-$C_{22}$ alkenoyl, $R_4$ is

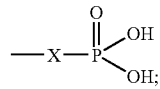

wherein X is selected from the group consisting of $CH_2$, CHOH, CHF, $CF_2$, and

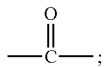;

$R_{13}$, $R_{14}$ and $R_{15}$ are independently selected from the group consisting of H, halo, $C_1$-$C_6$ alkyl, $C_1$-$C_6$ haloalkyl, $C_1$-$C_6$ alkoxy and $C_1$-$C_6$ haloalkoxy; and pharmaceutically acceptable salts thereof.

In accordance with one embodiment the LPA analog has the general structure

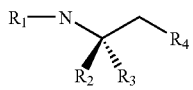

wherein $R_1$ is selected from the group consisting of $C_8$-$C_{22}$ alkyl, $C_8$-$C_{22}$ alkenyl,

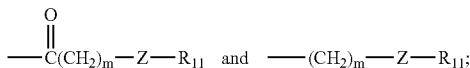

wherein m is 0-20;

Z is selected from the group consisting of $C_3$-$C_{10}$ cycloalkyl, $C_3$-$C_{15}$ bicycloalkyl, $C_5$-$C_{10}$ heterocyclic and phenyl;

$R_{11}$ is selected from the group consisting of $C_1$-$C_{10}$ alkyl, $C_1$-$C_{20}$ alkoxyl, $C_1$-$C_{20}$ alkylthio, and $C_1$-$C_{20}$ alkylamino;

$R_2$ and $R_3$ are independently selected from the group consisting of H, $C_1$-$C_6$ alkyl, $C_2$-$C_4$ alkenyl, $C_2$-$C_4$ alkynyl, —($C_1$-$C_4$ alkyl)OH, —($C_1$-$C_4$ alkyl)$NH_2$, —$COOR_5$, —($C_1$-$C_4$ alkyl)$COOR_5$, —($C_1$-$C_{10}$ alkyl)aryl, $C_3$-$C_8$ cycloalkyl, $C_3$-$C_8$ heterocyclic, $C_7$-$C_{12}$ bicyclic, ($C_5$-$C_8$ alkyl)aryl, ($C_5$-$C_8$ alkenyl)aryl, ($C_5$-$C_8$ alkynyl)aryl, and

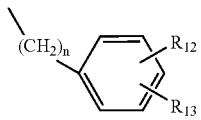

wherein n is 0-10;

$R_5$ is selected from the group consisting of H and $C_1$-$C_4$ alkyl;

$R_{12}$ is selected from the group consisting of halo, $C_1$-$C_{10}$ alkyl, ($C_0$-$C_{12}$ alkyl)aryl, ($C_2$-$C_{12}$ alkenyl)aryl, ($C_2$-$C_{12}$ alkynyl)aryl, —($C_1$-$C_4$ alkyl)OH, —($C_2$-$C_{12}$ alkenyl)OH, $SR_6$, $SOR_6$, $NHR_6$ and $OR_6$;

$R_{13}$ is selected from the group consisting of H, halo, $C_1$-$C_{10}$ alkyl, ($C_0$-$C_{12}$ alkyl)aryl, ($C_2$-$C_{12}$ alkenyl)aryl, ($C_2$-$C_{12}$ alkynyl)aryl, —($C_1$-$C_4$ alkyl)OH, —($C_2$-$C_{12}$ alkenyl)OH, $SR_6$, $SOR_6$, $NHR_6$ and $OR_6$;

wherein $R_6$ is selected from the group consisting of $C_1$-$C_{16}$ alkyl, $C_2$-$C_{16}$ alkenyl, $C_2$-$C_{16}$ alkynyl, —($C_1$-$C_4$ alkyl)$R_7$, —($C_2$-$C_4$ alkenyl)$R_7$, —($C_1$-$C_4$ carboxy)$R_7$ and —($C_2$-$C_4$ alkynyl)$R_7$; and $R_7$ is selected from the group consisting of optionally substituted $C_3$-$C_8$ cycloalkyl, optionally substituted $C_3$-$C_8$ heterocyclic, optionally substituted $C_7$-$C_{12}$ bicyclic optionally substituted $C_5$-$C_8$ aryl and optionally substituted $C_5$-$C_8$ heteroaryl, wherein the ring structures are substituted with one or more substituents selected from the group of $C_1$-$C_4$ alkyl, $C_1$-$C_4$ alkoxyl, halo, amino or hydroxy groups; and $R_4$ is selected from the group consisting of hydroxy,

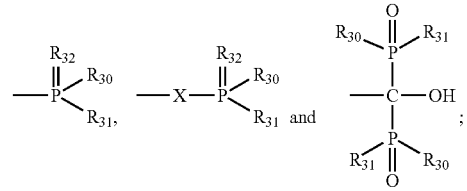

wherein $R_{32}$ is selected from the group consisting of O and S;

X is selected from the group consisting of O, NH, S, $CH_2$, CHOH, CHF, $CF_2$, and

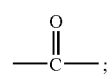;

and $R_{30}$ and $R_{31}$ are independently selected from the group consisting of $C_1$-$C_2$ alkoxy, $C_2$-$C_3$ alkenyloxy, $C_2$-$C_3$ alkynyloxy, aryloxy,

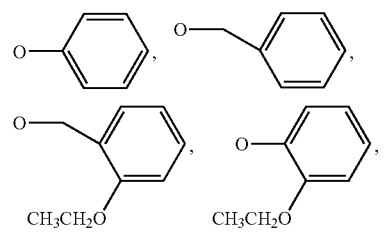

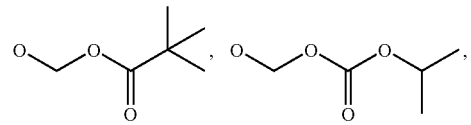

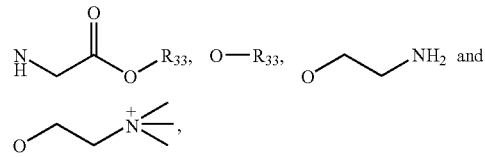

and pharmaceutically acceptable salts thereof. In one embodiment, $R_1$ is selected from the group consisting of

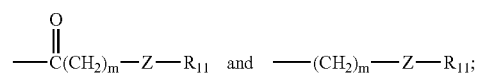

$R_3$ is H and $R_4$ is

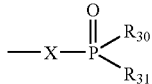

wherein X is selected from the group consisting of O, S, $CH_2$, CHOH and CHF; and $R_{30}$ and $R_{31}$ are independently selected from the group consisting of $C_1$-$C_2$ alkoxy,

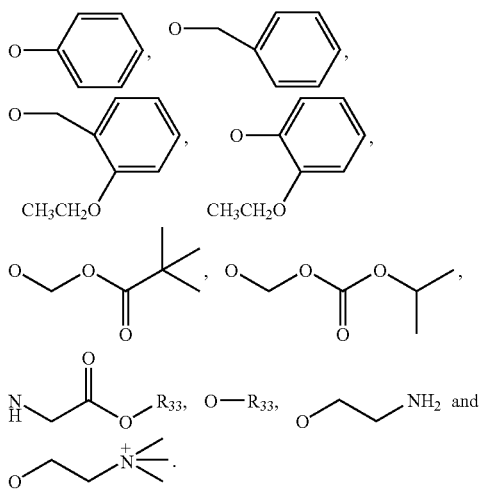

Alternatively, $R_1$ is selected from the group consisting of

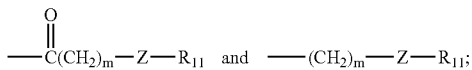

$R_2$ is H and $R_4$ is

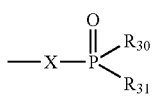

wherein X is selected from the group consisting of O, S, $CH_2$, CHOH and CHF; and $R_{30}$ and $R_{31}$ are independently selected from the group consisting of $C_1$-$C_2$ alkoxy,

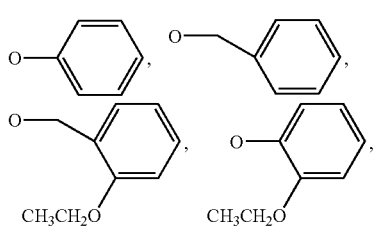

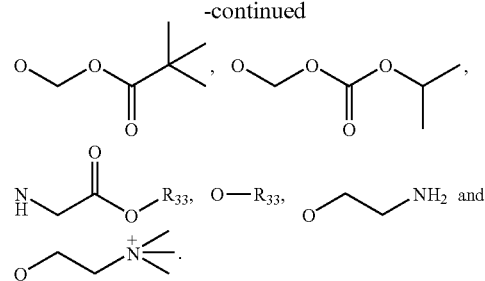

In one embodiment a compound of Formula I is provided wherein $R_1$ is selected from the group consisting of $C_8$-$C_{22}$ alkyl, $C_8$-$C_{22}$ alkenyl, $C_8$-$C_{22}$ alkanoyl, $C_9$-$C_{22}$ alkenoyl,

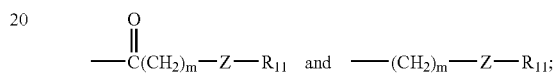

wherein m is 0-20;

Z is selected from the group consisting of $C_5$-$C_6$ aryl;

$R_{11}$ is selected from the group consisting of $C_1$-$C_{10}$ alkyl;

$R_2$ and $R_3$ are independently selected from the group consisting of H, $C_1$-$C_6$ alkyl, $C_2$-$C_4$ alkenyl, $C_2$-$C_4$ alkynyl, —($C_1$-$C_4$ alkyl)OH, —($C_1$-$C_4$ alkyl)$NH_2$, —$COOR_5$, —($C_1$-$C_4$ alkyl)$COOR_5$, $C_3$-$C_8$ cycloalkyl, $C_3$-$C_8$ heterocyclic, $C_7$-$C_{12}$ bicyclic, ($C_5$-$C_8$ alkenyl)aryl, ($C_5$-$C_8$ alkynyl)aryl and

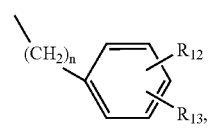

with the proviso that $R_2$ and $R_3$ are not both H;

wherein n is 0-10;

$R_5$ is selected from the group consisting of H and $C_1$-$C_4$ alkyl;

$R_{12}$ and $R_{13}$ are independently selected from the group consisting of H, halo, $C_1$-$C_{16}$ alkyl, $C_2$-$C_{16}$ alkenyl, $C_2$-$C_{16}$ alkynyl, —($C_1$-$C_4$ alkyl)$R_7$, —($C_2$-$C_4$ alkenyl)$R_7$, —($C_1$-$C_4$ carboxy)$R_7$ and —($C_2$-$C_4$ alkynyl)$R_7$;

$R_7$ is selected from the group consisting of optionally substituted $C_3$-$C_8$ cycloalkyl, optionally substituted $C_3$-$C_8$ heterocyclic, optionally substituted $C_7$-$C_{12}$ bicyclic optionally substituted $C_5$-$C_8$ aryl and optionally substituted $C_5$-$C_8$ heteroaryl, wherein the ring structures are substituted with one or more substituents selected from the group of $C_1$-$C_4$ alkyl, $C_1$-$C_4$ alkoxyl and $C_1$-$C_4$ haloalkyl;

y is 0 or 1; and $R_4$ is

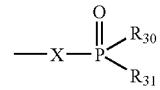

wherein X is selected from the group consisting of O, S, $CH_2$, CHOH and CHF; and $R_{30}$ and $R_{31}$ are independently selected from the group consisting of $C_1$-$C_2$ alkoxy,

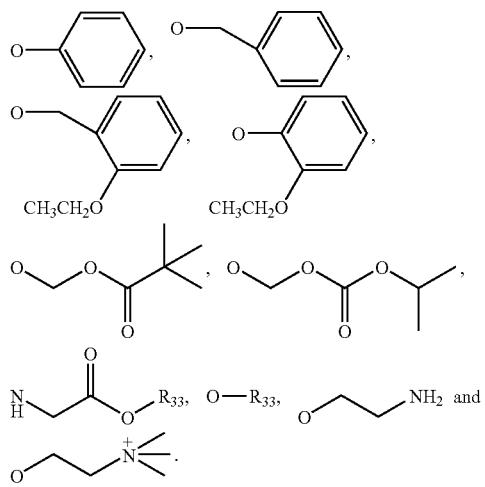

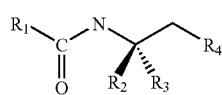

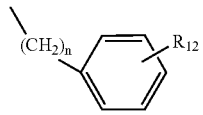

In another embodiment of the present invention the LPA analog is a compound represented by the structure:

III

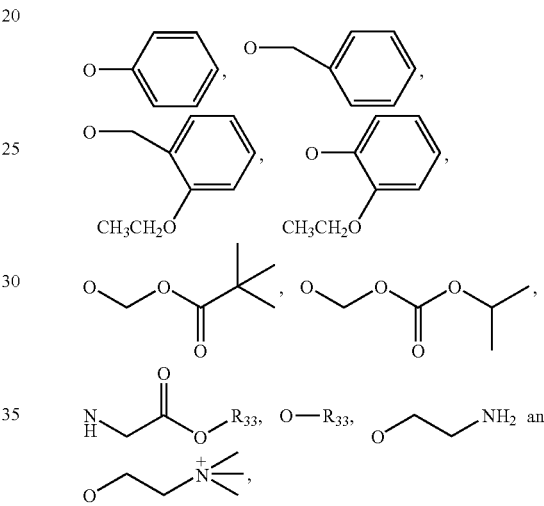

wherein $R_1$ is selected from the group consisting of $C_8$-$C_{22}$ alkyl and $C_8$-$C_{22}$ alkenyl, substituted $C_8$-$C_{22}$ alkyl and substituted $C_8$-$C_{22}$ alkenyl;

$R_2$ and $R_3$ are independently selected from the group consisting of H, $C_1$-$C_6$ alkyl, $C_2$-$C_4$ alkenyl, $C_2$-$C_4$ alkynyl, —($C_1$-$C_4$ alkyl)OH, —($C_1$-$C_4$ alkyl)$NH_2$, —$COOR_5$, —($C_1$-$C_4$ alkyl)$COOR_5$, —($C_1$-$C_{10}$ alkyl)aryl, $C_3$-$C_8$ cycloalkyl, $C_3$-$C_8$ heterocyclic, $C_7$-$C_{12}$ bicyclic, ($C_5$-$C_8$ alkyl)aryl, ($C_5$-$C_8$ alkenyl)aryl, ($C_5$-$C_8$ alkynyl)aryl, and

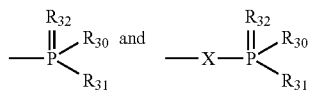

wherein n is 0-10;

$R_5$ is selected from the group consisting of H and $C_1$-$C_4$ alkyl;

$R_{12}$ is selected from the group consisting of halo, $C_1$-$C_{10}$ alkyl, ($C_0$-$C_{12}$ alkyl)aryl, ($C_2$-$C_{12}$ alkenyl)aryl, ($C_2$-$C_{12}$ alkynyl)aryl, —($C_1$-$C_4$ alkyl)OH, —($C_2$-$C_{12}$ alkenyl)OH, $SR_1$, $SOR_6$, $NHR_6$ and $OR_6$;

wherein $R_6$ is selected from the group consisting of $C_1$-$C_{16}$ alkyl, $C_2$-$C_{16}$ alkenyl, $C_2$-$C_{16}$ alkynyl, —($C_1$-$C_4$ alkyl)$R_7$, —($C_2$-$C_4$ alkenyl)$R_7$, —($C_1$-$C_4$ carboxy)$R_7$ and —($C_2$-$C_4$ alkynyl)$R_7$; and $R_7$ is selected from the group consisting of optionally substituted $C_3$-$C_8$ cycloalkyl, optionally substituted $C_3$-$C_8$ heterocyclic, optionally substituted $C_7$-$C_{12}$ bicyclic and optionally substituted $C_5$-$C_8$ cycloalkenyl and optionally substituted aryl, wherein the ring structures are substituted with one or more substituents selected from the group of $C_1$-$C_4$ alkyl, $C_1$-$C_4$ alkoxyl, halo, amino or hydroxy groups; and $R_4$ is selected from the group consisting of

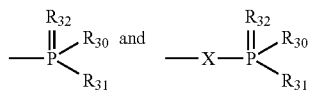

wherein $R_{32}$ is selected from the group consisting of O and S;

X is selected from the group consisting of O, S, $CH_2$, CHOH and CHF; and $R_{30}$ and $R_{31}$ are independently selected from the group consisting of $C_1$-$C_2$ alkoxy,

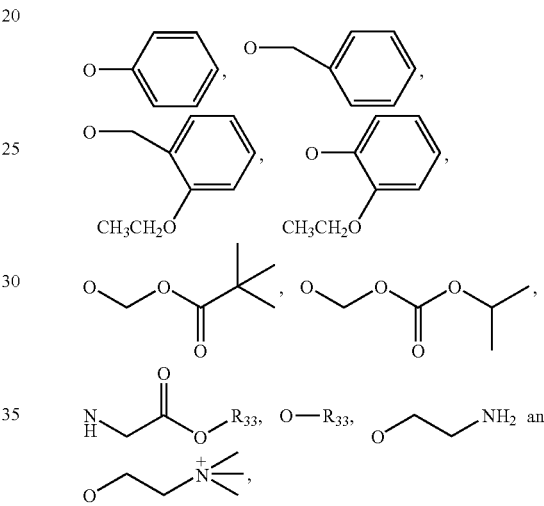

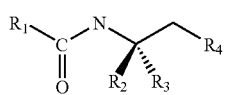

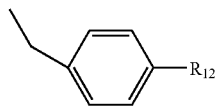

and pharmaceutically acceptable salts thereof.

In accordance with one embodiment, the LPA analogs of the present invention are represented by the structure:

III

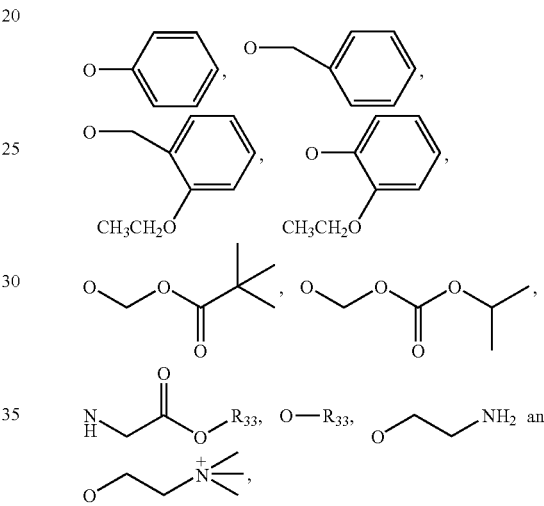

wherein $R_1$ is selected from the group consisting of $C_8$-$C_{22}$ alkyl, $C_8$-$C_{22}$ alkenyl;

$R_2$ and $R_3$ are independently selected from the group consisting of H, $C_1$-$C_6$ alkyl, $C_2$-$C_4$ alkenyl, $C_2$-$C_4$ alkynyl, —($C_1$-$C_4$ alkyl)OH, —($C_1$-$C_4$ alkyl)$NH_2$, —$COOR_5$, —($C_1$-$C_4$ alkyl)$COOR_5$, —($C_1$-$C_{10}$ alkyl)aryl, $C_3$-$C_8$ cycloalkyl, $C_3$-$C_8$ heterocyclic, $C_7$-$C_{12}$ bicyclic, ($C_5$-$C_8$ alkyl)aryl, ($C_5$-$C_8$ alkenyl)aryl, ($C_5$-$C_8$ alkynyl)aryl, and

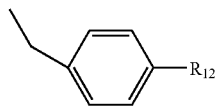

$R_4$ selected from the group consisting of

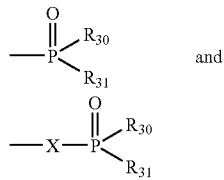
and wherein X is selected from the group consisting of O, S, $CH_2$, CHOH, $CF_2$, CHF and

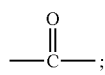

and
$R_{30}$ and $R_{31}$ are independently selected from the group consisting of $C_1$-$C_2$ alkoxy,

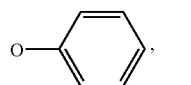, 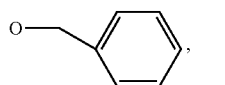,

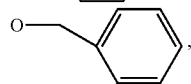, 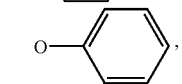,

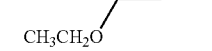 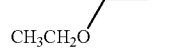

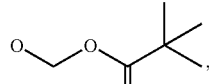,

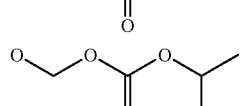,

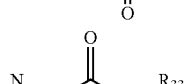 , and

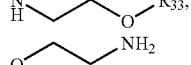;

$R_5$ is selected from the group consisting of H and $C_1$-$C_4$ alkyl;
$R_{12}$ is selected from the group consisting of halo, $C_1$-$C_6$ alkyl, $C_1$-$C_6$ alkyl($C_5$-$C_8$ cycloalkenyl), $C_1$-$C_6$ alkenyl($C_5$-$C_8$ cycloalkenyl), ($C_0$-$C_{12}$ alkyl)aryl, ($C_2$-$C_{12}$ alkenyl)aryl, ($C_2$-$C_{12}$ alkynyl)aryl, —($C_1$-$C_4$ alkyl)OH, —($C_1$-$C_4$ alkenyl)OH, and $OR_6$;
$R_6$ is selected from the group consisting of $C_1$-$C_{16}$ alkyl, $C_2$-$C_{16}$ alkenyl, $C_2$-$C_{16}$ alkynyl, —($C_1$-$C_4$ carboxy)$R_7$—($C_1$-$C_4$ alkyl)$R_7$, —($C_2$-$C_4$ alkenyl)$R_7$ and —($C_2$-$C_4$ alkynyl)$R_7$; and
$R_7$ is selected from the group consisting of optionally substituted $C_3$-$C_8$ cycloalkyl, optionally substituted $C_3$-$C_8$ heterocyclic, optionally substituted $C_7$-$C_{12}$ bicyclic and optionally substituted $C_5$-$C_8$ aryl, wherein the ring structures are substituted with one or more substituents selected from the group of $C_1$-$C_4$ alkyl, $C_1$-$C_4$ alkoxyl, halo, amino or hydroxy groups and pharmaceutically acceptable salts thereof. In one embodiment, $R_1$ is $C_{13}$-$C_{17}$ alkyl or $C_{17}$-$C_{21}$ alkenyl, and $R_3$ is H. In one embodiment $R_1$ is a 15:0, 17:0, 17:1, 19:4 or 21:6 hydrocarbon, $R_3$ is H and $R_4$ is $OPO_3^{-2}$ or methylene phosphonate. The activities of various members of this series have been tested at the three LPA receptor subtypes and found to have LPA receptor agonist and antagonist activities.

In accordance with one embodiment of the present invention an LPA antagonist of general Formula III is provided wherein $R_1$ is selected from the group consisting of $C_8$-$C_{22}$ alkyl, $C_8$-$C_{22}$ alkenyl;
$R_2$ is

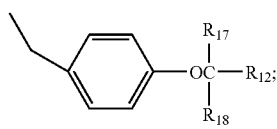

$R_3$ is H or $C_1$-$C_6$ alkyl;
$R_4$ is

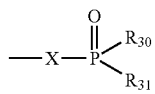

or other phosphonate analog;
wherein X is selected from the group consisting of O, S, CHOH, $CR_{17}R_{18}$, and

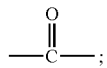;

wherein $R_{17}$ and $R_{18}$ are independently H or halo; and,
$R_{30}$ and $R_{31}$ are independently selected from the group consisting of $C_1$-$C_2$ alkoxy,

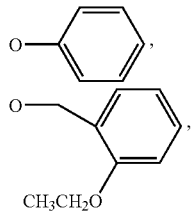

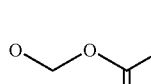,

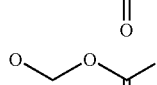,

,

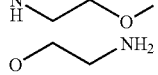 

and

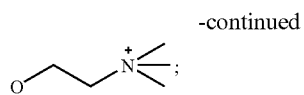

$R_{12}$ is a heterocyclic substituent selected from the group consisting of

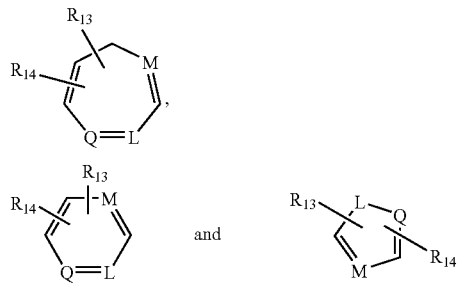

wherein L, M, and Q are independently selected from the group consisting of N, $NR_{15}$, O, S, $CHR_{15}$ and $CR_{15}R_{16}$;

$R_{13}$, $R_{14}$, $R_{15}$ and $R_{16}$ are independently selected from the group consisting of H, halo, $C_1$-$C_6$ alkyl, $C_1$-$C_6$ haloalkyl and $C_1$-$C_6$ alkoxy; and pharmaceutically acceptable salts thereof.

In accordance with one embodiment of the present invention an LPA antagonist of general Formula III is provided wherein $R_1$ is selected from the group consisting of $C_8$-$C_{22}$ alkyl, $C_8$-$C_{22}$ alkenyl;

$R_2$ is H or $C_1$-$C_6$ alkyl;

$R_3$ is

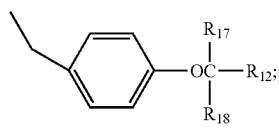

$R_4$ is

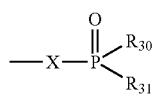

or other phosphonate analog;

wherein X is selected from the group consisting of O, S, CHOH, $CR_{17}R_{18}$, and

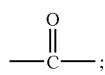

wherein $R_{17}$ and $R_{18}$ are independently H or halo; and $R_{30}$ and $R_{31}$ are independently selected from the group consisting of $C_1$-$C_2$ alkoxy,

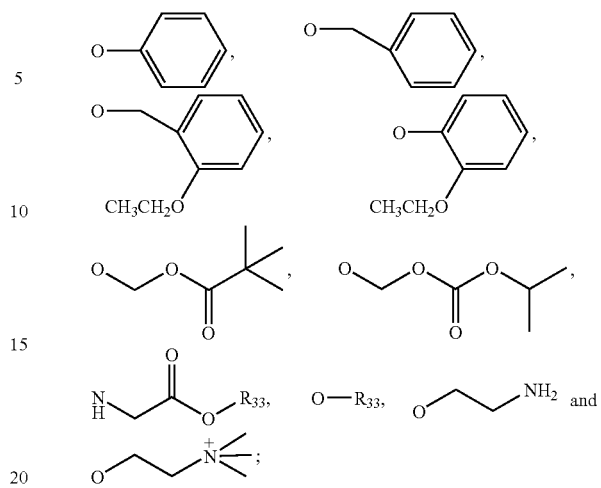

$R_{12}$ is a heterocyclic substituent selected from the group consisting of

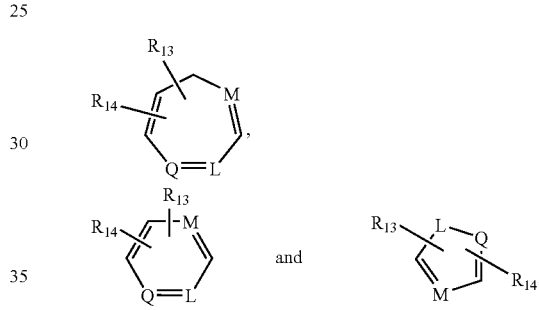

wherein L, M, and Q are independently selected from the group consisting of H, $NR_{15}$, O, S, $CHR_{15}$ and $CR_{15}R_{16}$;

$R_{13}$, $R_{14}$, $R_{15}$ and $R_{16}$ are independently selected from the group consisting of H, halo, $C_1$-$C_6$ alkyl, $C_1$-$C_6$ haloalkyl and $C_1$-$C_6$ alkoxy; and pharmaceutically acceptable salts thereof, In another embodiment of the present invention an LPA antagonist of general Formula III is provided wherein $R_1$ is selected from the group consisting of $C_8$-$C_{22}$ alkyl, $C_8$-$C_{22}$ alkenyl;

$R_2$ and $R_3$ are independently selected from the group consisting of H and

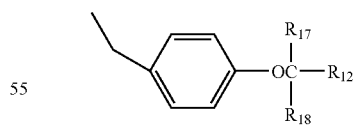

with the proviso that either $R_2$ or $R_3$ is

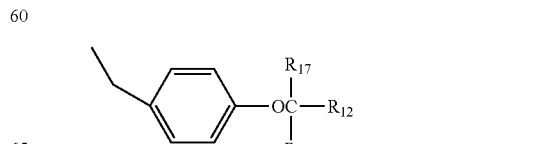

$R_4$ selected from the group consisting of

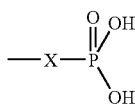

wherein X is selected from the group consisting of O, S, CHOH, $CR_{17}R_{18}$ and

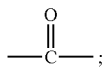

wherein $R_{17}$ and $R_{18}$ are independently H or F; and
$R_{12}$ is a heterocyclic substituent represented by the formula

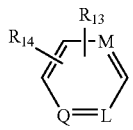

wherein L, M, and Q are independently selected from the group consisting of N, O, S and $CHR_{15}$, with the proviso that at least one of M, Q and L is not $CHR_{15}$;

$R_{13}$, $R_{14}$ and $R_{15}$ are independently selected from the group consisting of H, F, $C_1$-$C_6$ alkyl, $C_1$-$C_6$ haloalkyl and $C_1$-$C_6$ alkoxy; and pharmaceutically acceptable salts thereof. In one embodiment, $R_1$ is $C_{13}$-$C_{17}$ alkyl or $C_{17}$-$C_{21}$ alkenyl, $R_{17}$ and $R_{18}$ are both H. In another embodiment $R_1$ is $C_{13}$-$C_{17}$ alkyl or $C_{17}$-$C_{21}$ alkenyl, $R_3$ is H and $R_2$ is

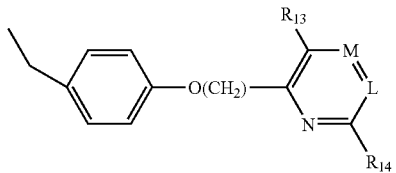

wherein L and M are independently selected from the group consisting of N, O, S and $CHR_{15}$;

$R_{13}$, $R_{14}$ and $R_{15}$ are independently selected from the group consisting of H, $C_1$-$C_6$ alkyl, $C_1$-$C_6$ haloalkyl and $C_1$-$C_6$ alkoxy. In one embodiment $R_1$ is a 15:0, 17:0, 17:1, 19:4 or 21:6 hydrocarbon, $R_3$ is H and X is $CH_2$, CHOH, CHF, $CF_2$ or

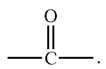

The activities of various members of this series have been tested at the three LPA receptor subtypes and found to have LPA receptor antagonist activities.

One embodiment of the present invention is directed to the compounds of Formula III wherein $R_1$ is a 15:0, 17:0, 17:1, 19:4 or 21:6 hydrocarbon, $R_3$ is H, $R_4$ is $OPO_3^{-2}$ (or a phosphor-ester derivative thereof) and $R_2$ is selected from the group consisting of 2-substitutions: methylene amino; para chloro benzyl; methylene benzyl; phenyl; methyl amino benzyl; aryl; and di-methyl. LPA analogs wherein $R_4$ is hydroxyl have not demonstrated activity as LPA receptor agonists or antagonists. However, it is anticipated that such compounds will be phosphorylated in vivo upon administration. Therefore compounds that have activity when $R_4$ is $OPO_3^{-2}$ may be formulated as prodrugs by substituting a hydroxy for $OPO_3^{-2}$ at $R_4$. Similarly, the $OPO_3^{-2}$ group at $R_4$ can be substituted with a phospho-ester group to form a prodrug that is more readily taken up by a patient's alimentary canal. In addition, the corresponding enantiomers for all the LPA analogs of the present invention are also encompassed by the present invention wherein $R_1$ is a 15:0, 17:0, 17:1, 19:4 or 21:6 hydrocarbon, $R_4$ is selected from the group consisting of

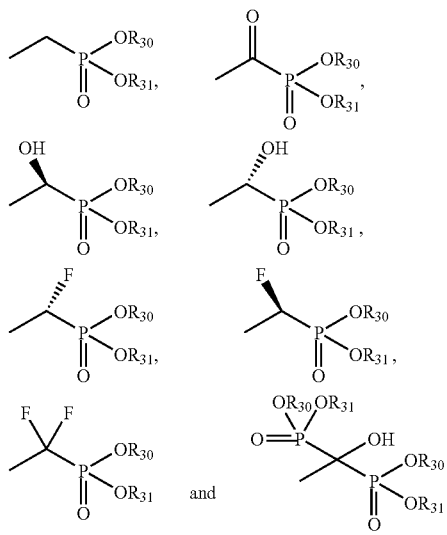

wherein $R_{30}$ and $R_{31}$ are independently selected from the group consisting of $C_1$-$C_2$ alkoxy,

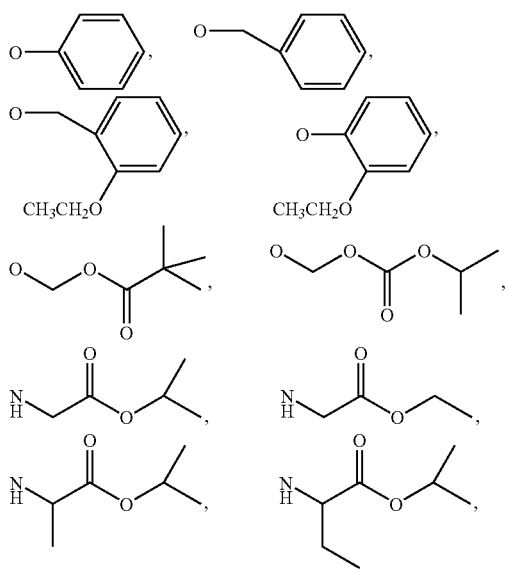

-continued

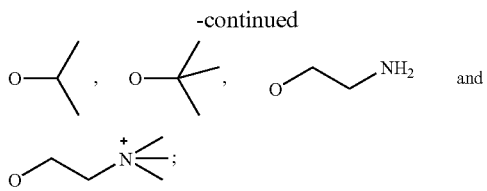
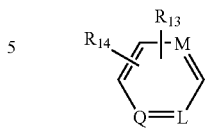

and $R_2$ and $R_3$ are independently selected from the group consisting of H, and

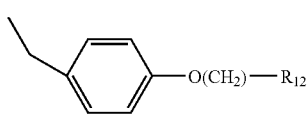

$R_{12}$ is a heterocyclic substituent represented by the formula wherein L, M, and Q are selected from the group consisting of N, O, S and $CHR_{15}$, with the proviso that at least one of M, Q and L is not $CHR_{15}$ and that one of $R_2$ and $R_3$ is H and the other is not H.

$R_{13}$, $R_{14}$ and $R_{15}$ are independently selected from the group consisting of H, F, $C_1$-$C_6$ alkyl, $C_1$-$C_6$ haloalkyl and $C_1$-$C_6$ alkoxy; and pharmaceutically acceptable salts thereof. Additional compounds encompassed by the present invention include:

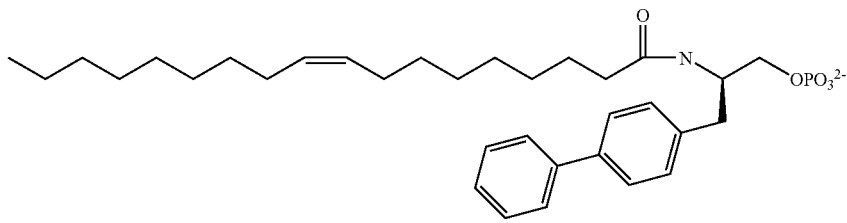

VPC13061

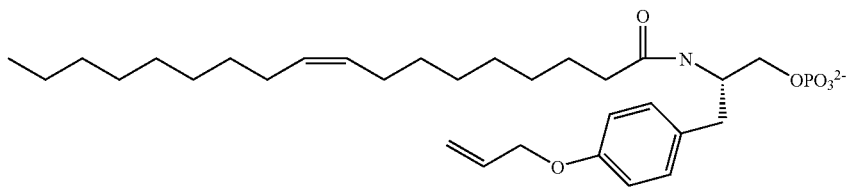

VPC31183

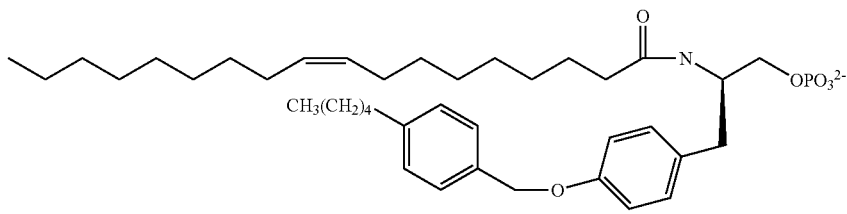

VPC31162

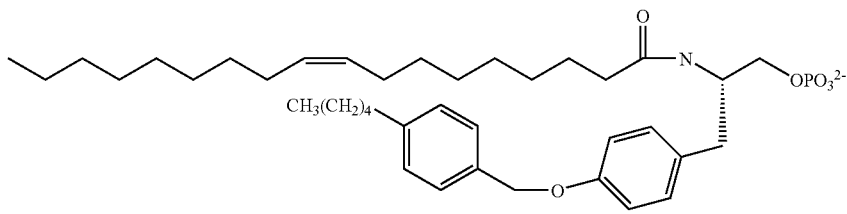

VPC31191

-continued
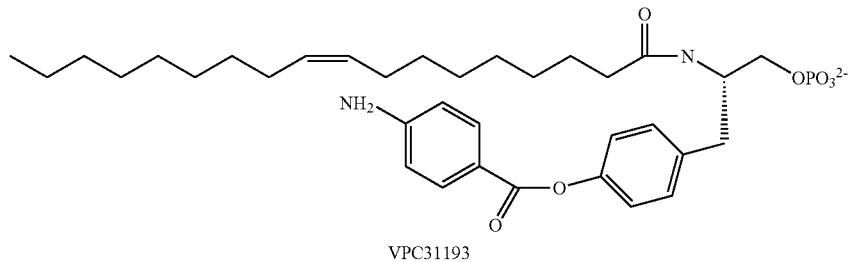
VPC31193
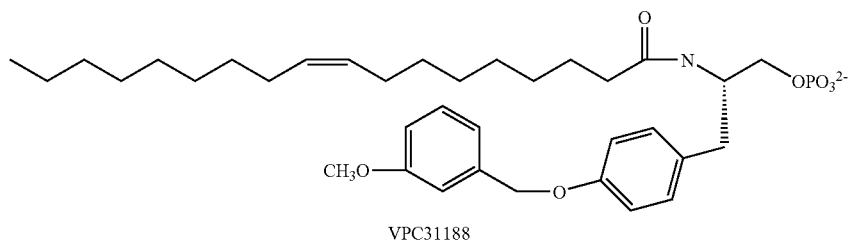
VPC31188
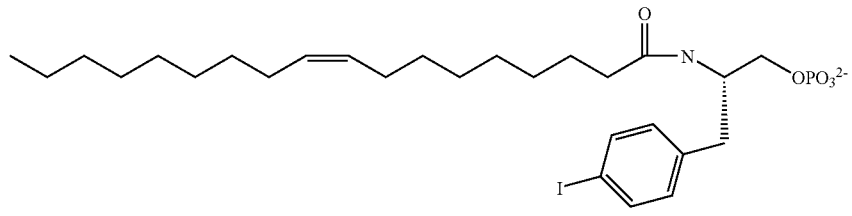
VPC13075
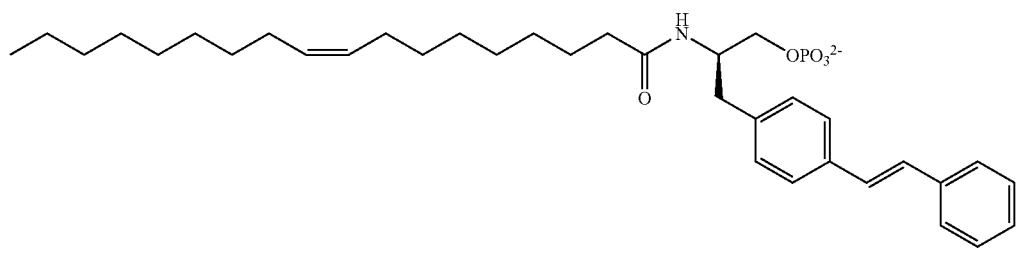
VPC13063
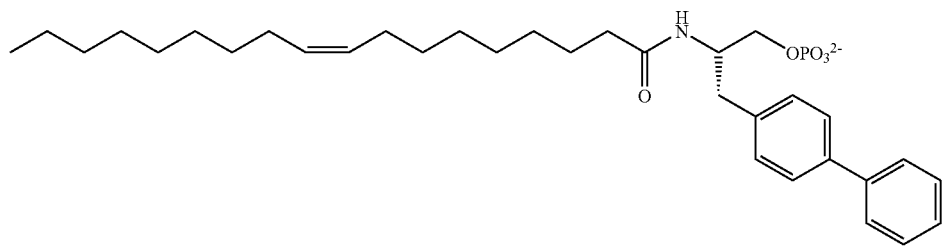
VPC13082
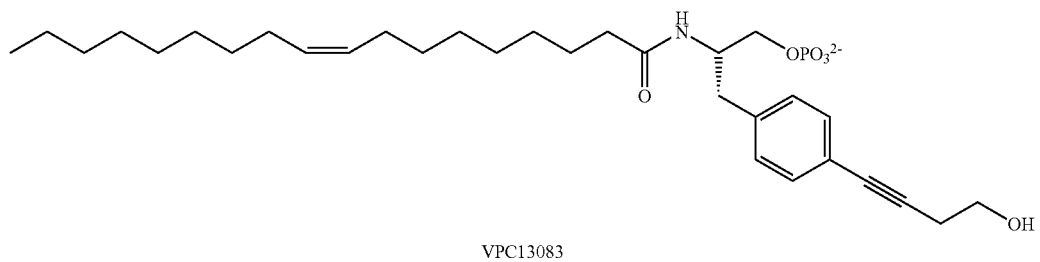
VPC13083

-continued
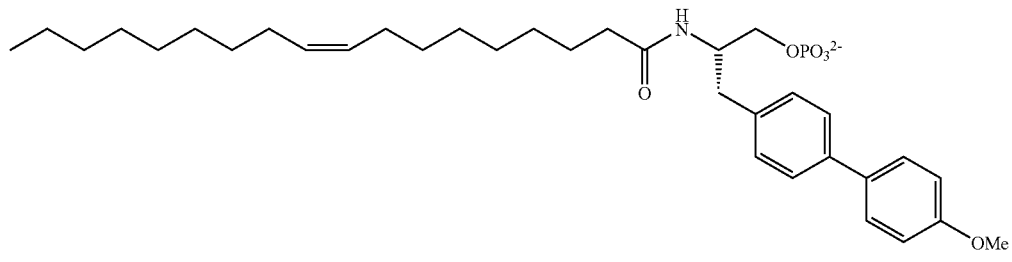
VPC13081
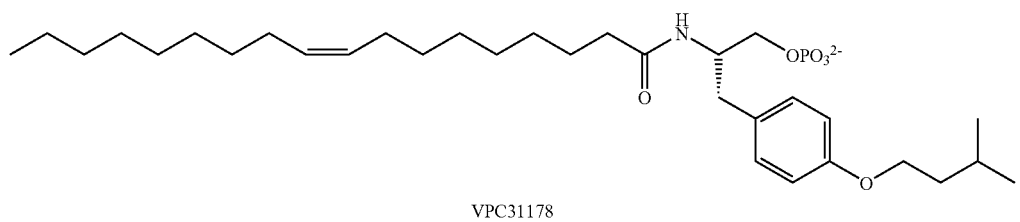
VPC31178
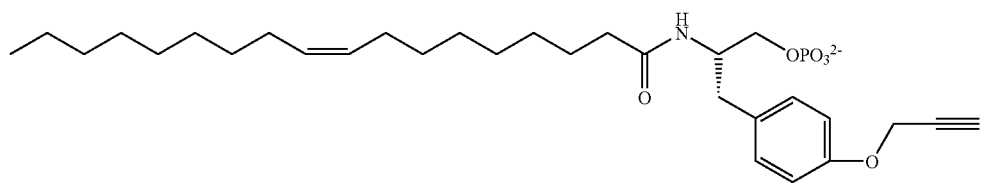
VPC31175
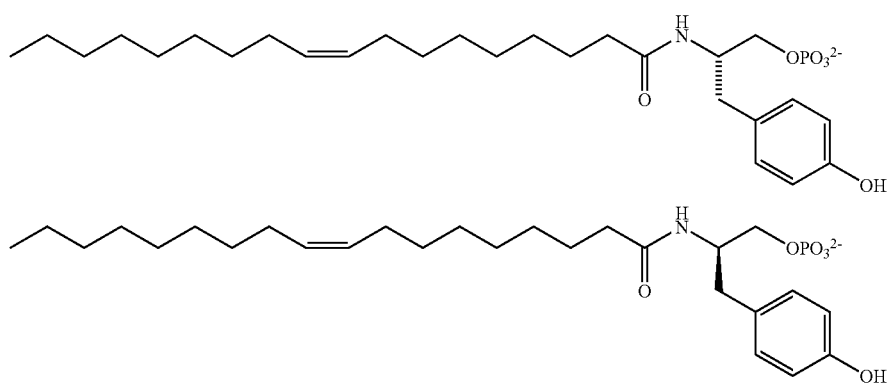
VPC12207
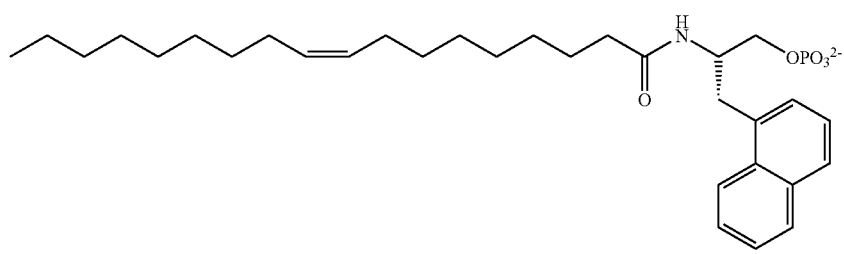
VPC12228
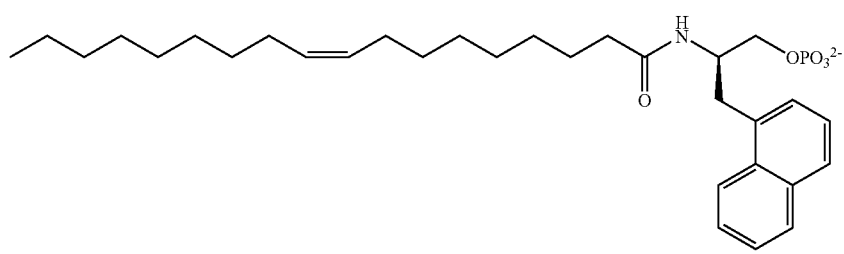
VPC12235

-continued
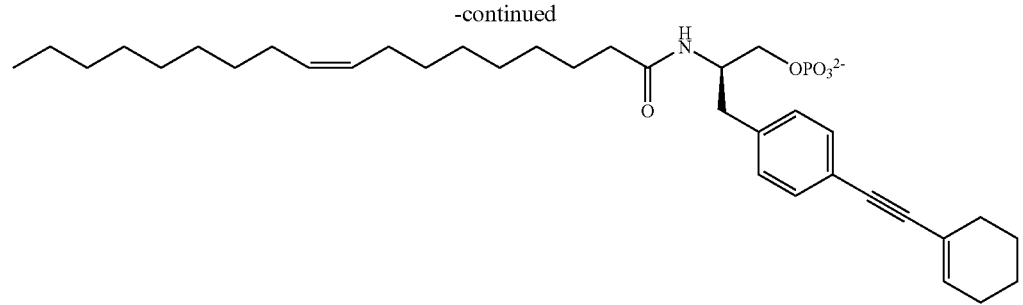
VPC13069
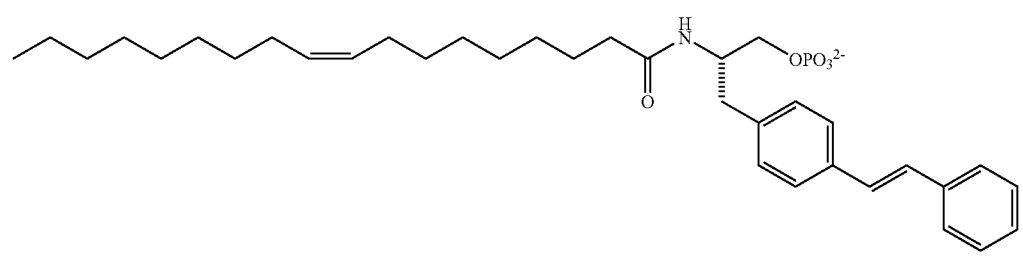
VPC13086
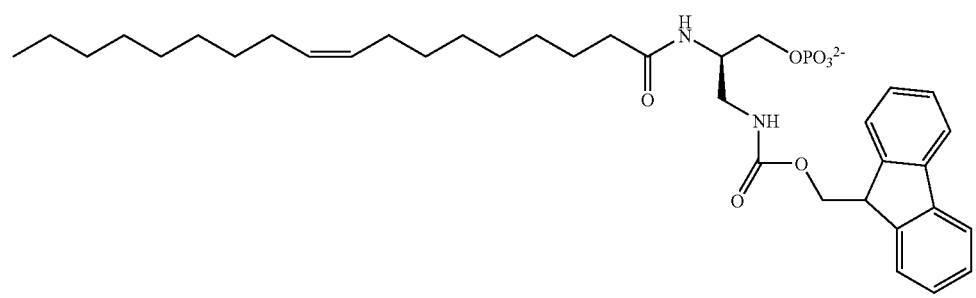
VPC12199
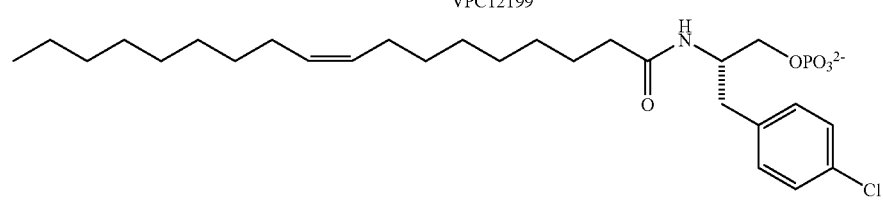
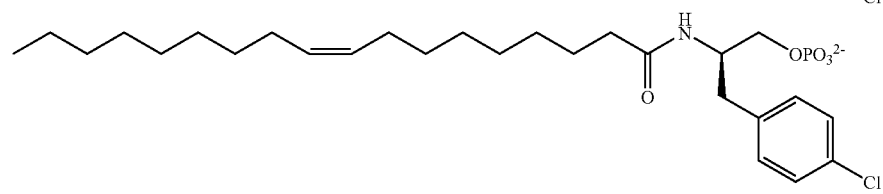
VPC12171
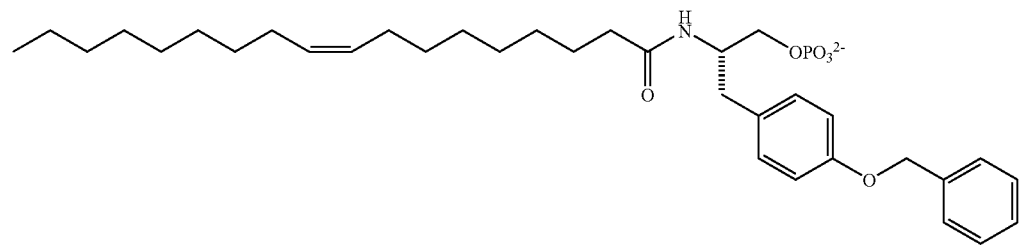
VPC12249

-continued
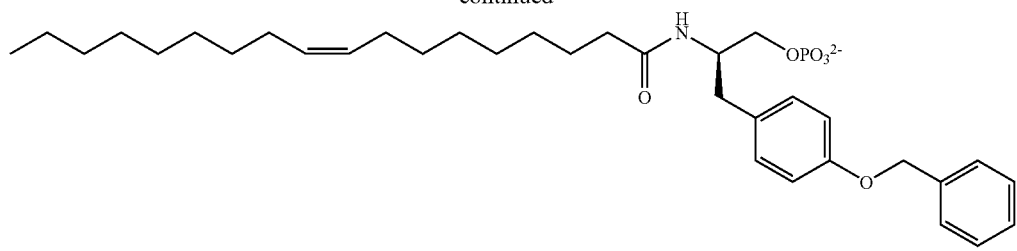
VPC12249
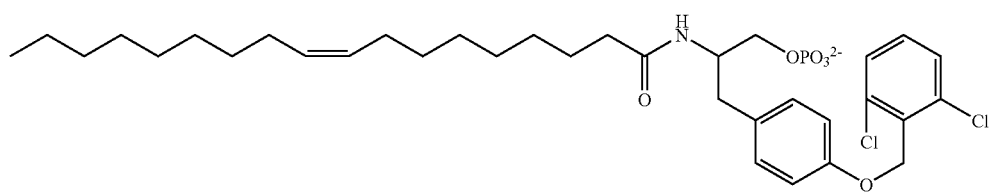
VPC12284
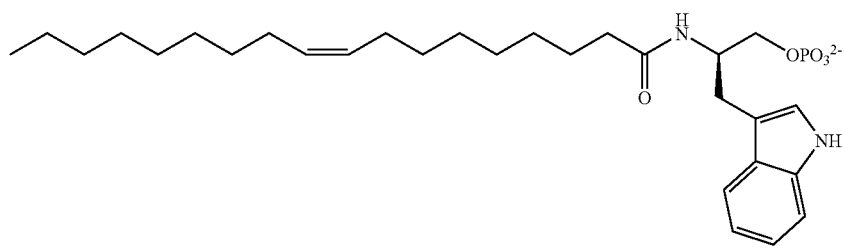
VPC12293
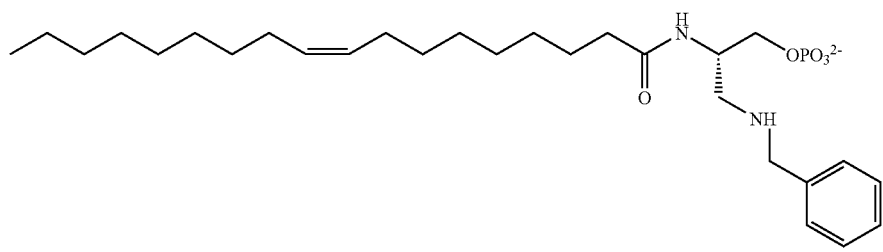
VPC12153
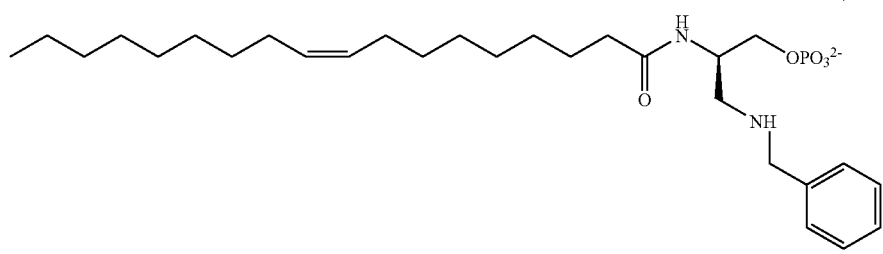
VPC12153
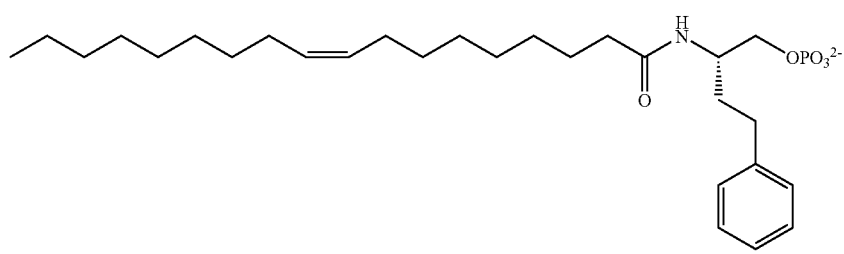
VPC12224

-continued
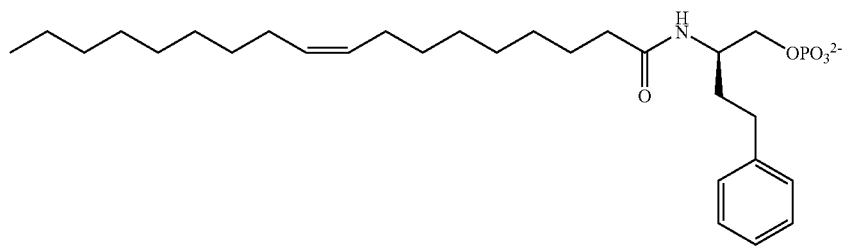
VPC12155
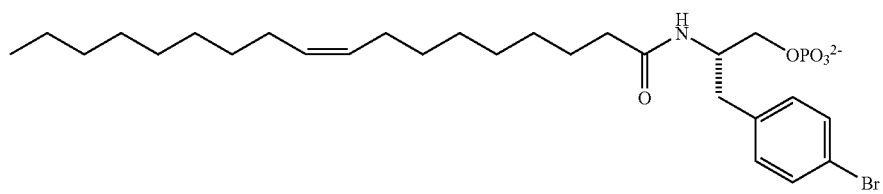
VPC12272
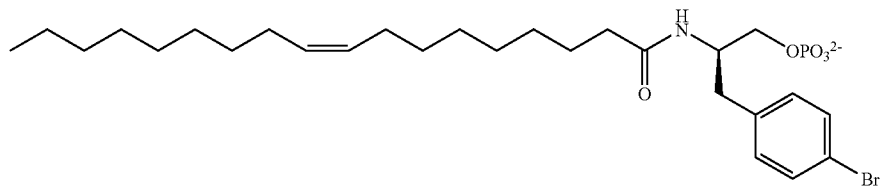
VPC12280
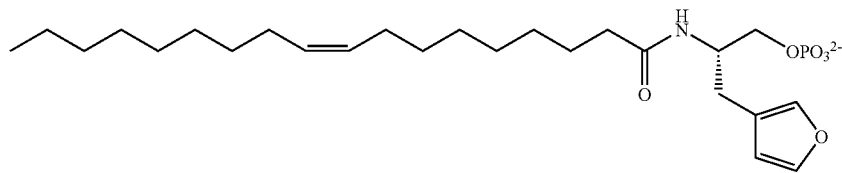
VPC12229
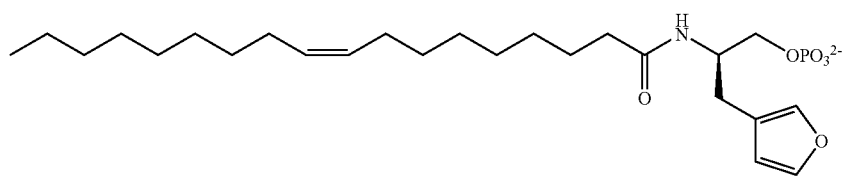
VPC12250
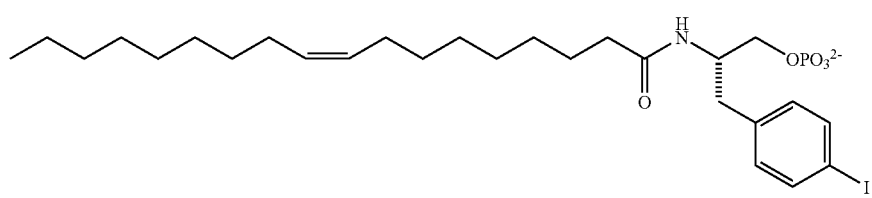
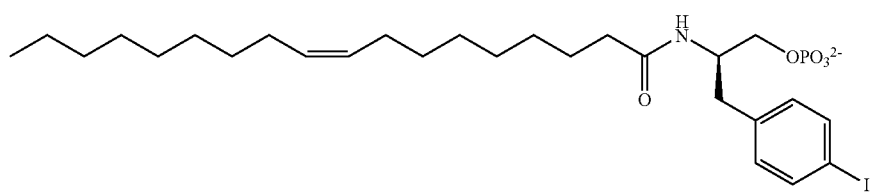
VPC13075

-continued
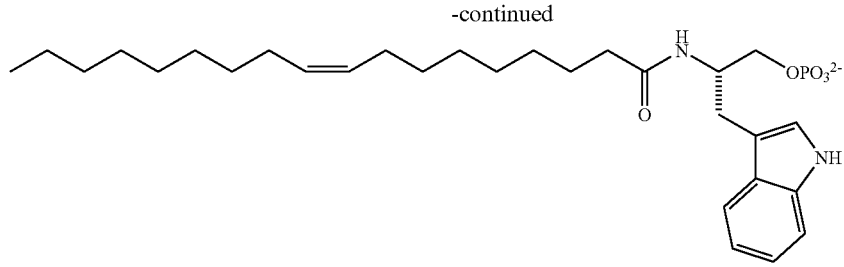
VPC12227
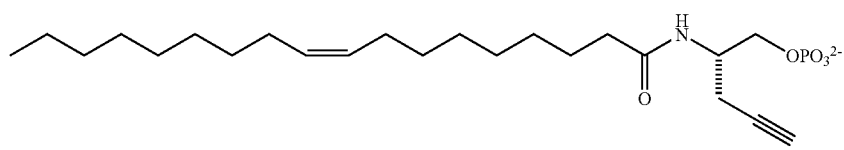
VPC12262
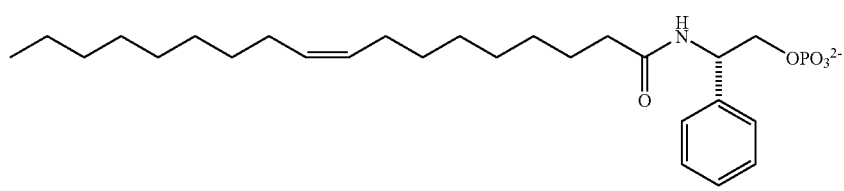
VPC12185
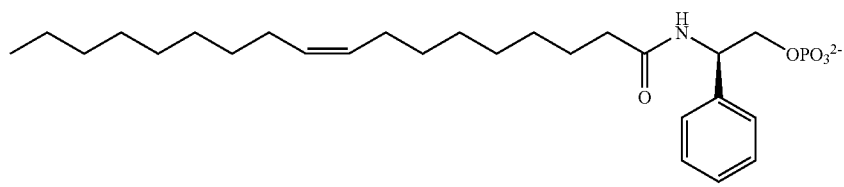
VPC12182
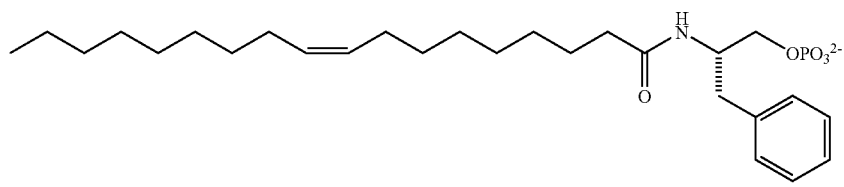
VPC12255
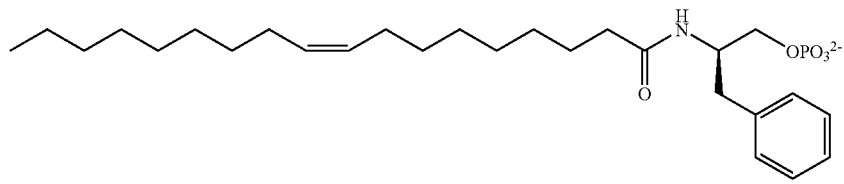
VPC12084
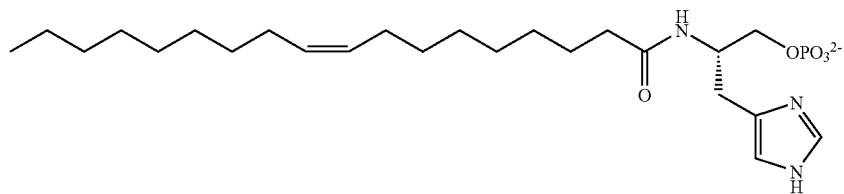
VPC30054

-continued
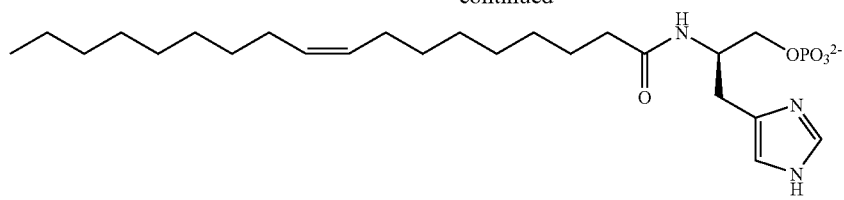
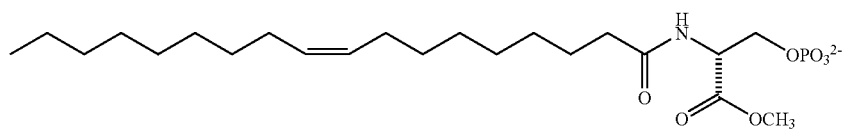
VPC31180
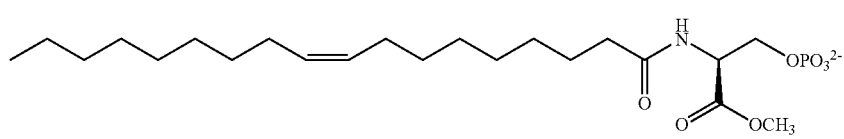
VPC31139
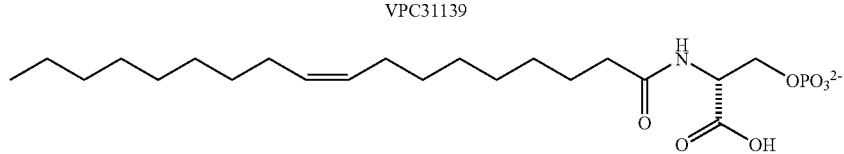
NASPA
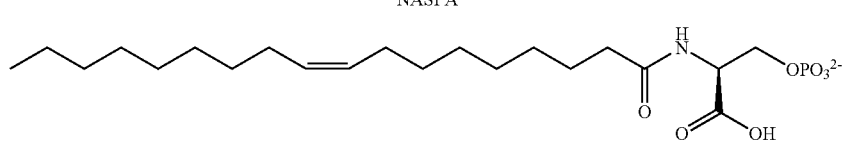
NASPA
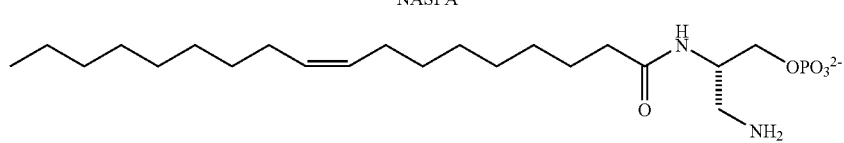
VPC12048
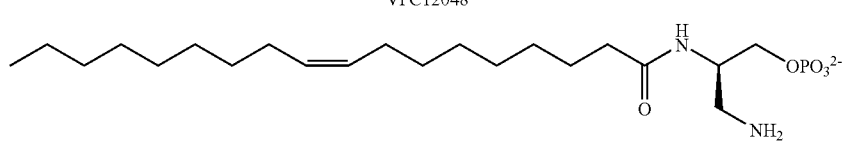
VPC12178
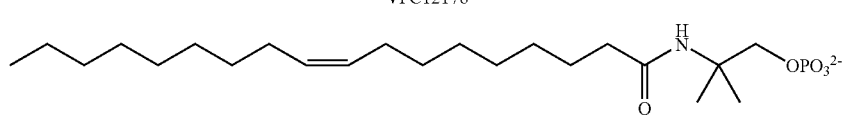
VPC12179
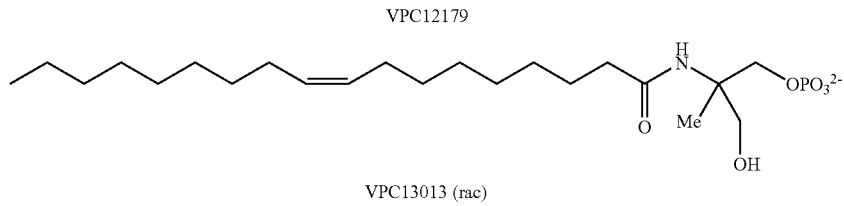
VPC13013 (rac)
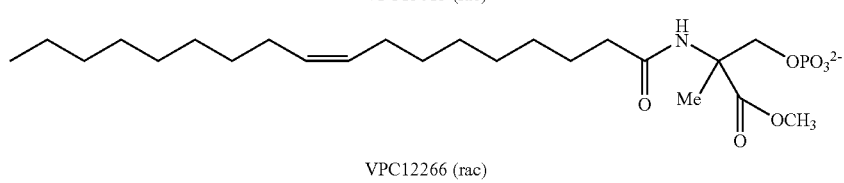
VPC12266 (rac)

-continued
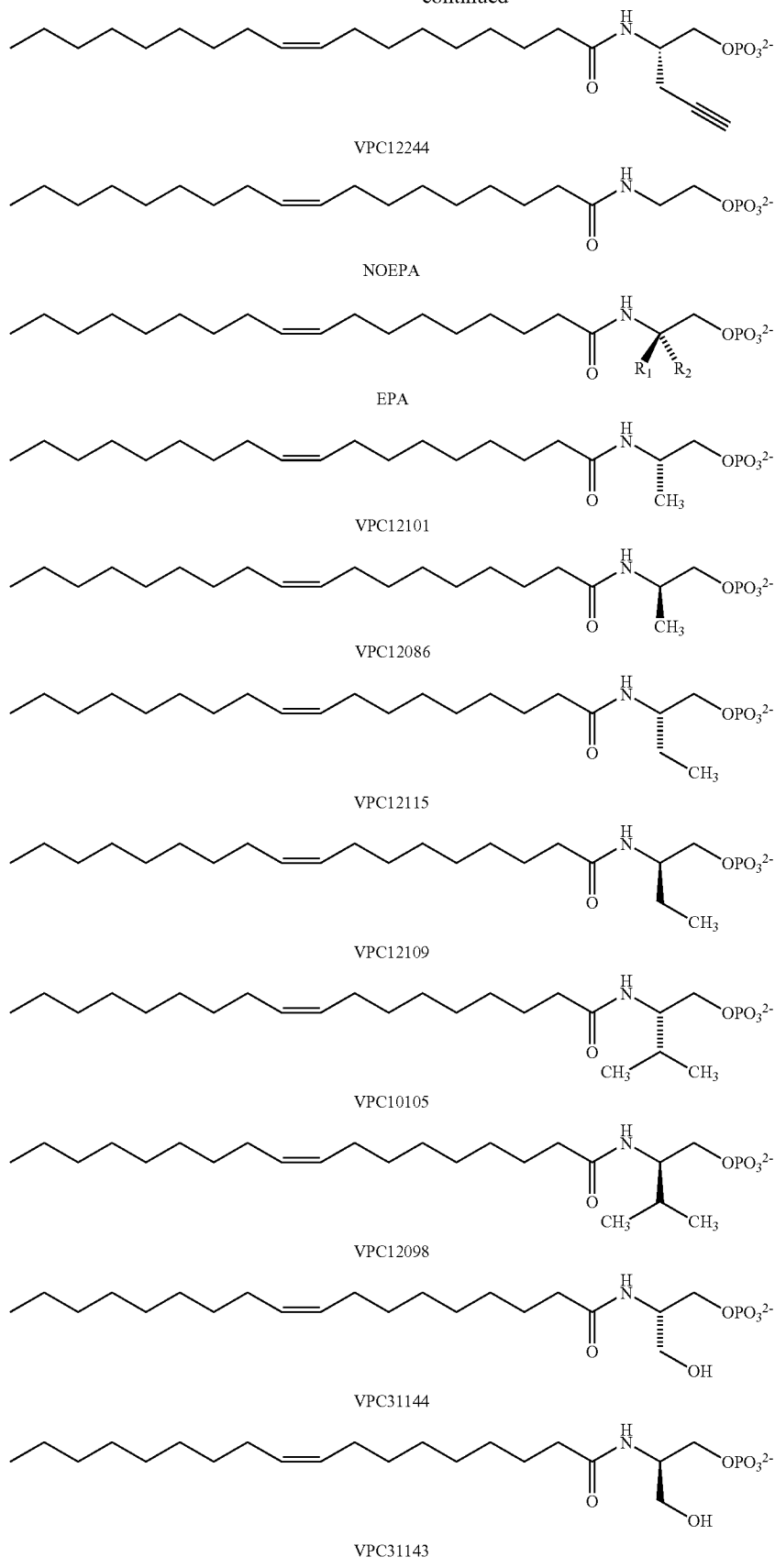

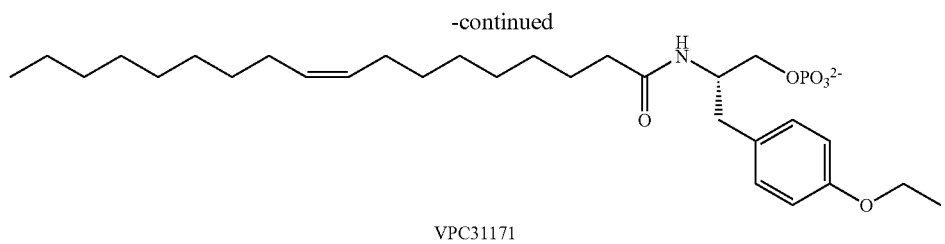

VPC31171

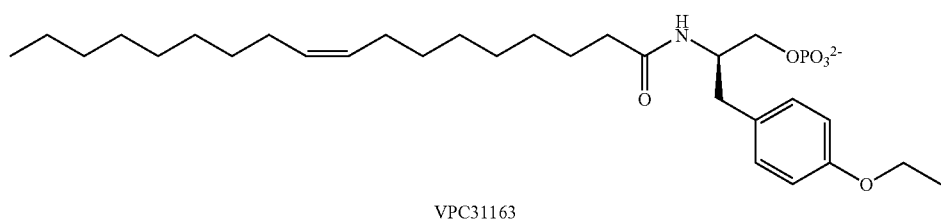

VPC31163

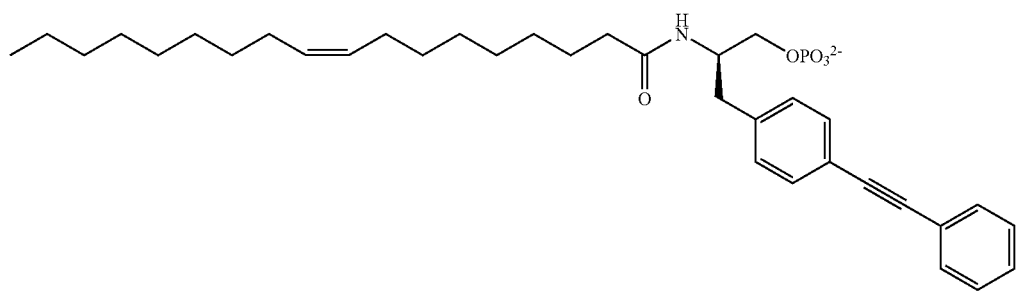

VPC13066 as well as phospho-ester derivatives of such compounds.

LPA is metabolized by a variety of conceivable routes including phosphatases, esterases and LPA acyl transferases or transported into cells. The LPA signal at receptors might be prolonged if the routes of degradation could be evaded or inhibited by LPA structural analogs. The LPA analogs of the present invention can be used, in accordance with one embodiment, to inhibit/evade endogenous LPA metabolic pathways including phosphotases, esterases, transporters and LPA acyl transferases. For example those LPA analogs of Formula I that lack and ester bond would be resistant to degradation by endogenous esterases. One embodiment of the present invention is directed to compounds that function as a LPA receptor agonists and antagonists that are resistant to hydrolysis by lyso-lipid phosphate phosphatases (LPPs) and are sub-type selective inhibitors of LPPs. Previously described LPA mimetics contain a phosphate group, and thus are likely susceptible to hydrolysis by LPPs. Furthermore, previously described LPA mimetics have not been shown to be selective for a particular LPA receptor.

Alpha hydroxy phosphonates are well known phosphate mimetics. For example, the compounds used clinically to treat osteoporosis (pamidronate, alendronate) are alpha hydroxy bisphosphonates that are analogs of pyrophosphate. LPA analogs were synthesized wherein the phosphate moiety is replaced by an alpha hydroxy phosphonate. Rather than being directly analogous to LPA, the LPP resistant compounds of the present invention are analogous to N-oleoyl ethanolamide phosphate—a compound that has been reported to be a potent, efficacious LPA mimetic. The structure of this compound, N-oleoyl-1-hydroxy propylamide phosphonic acid (NOHPP), is as follows:

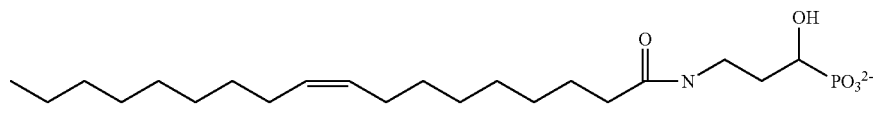

The IUPAC name of NOHPP is (9Z)-N-(rac-3-hydroxy-3-phosphonopropyl)octadec-9-enamide. The present invention also encompasses phospho-ester prodrug forms of this compound having the structure

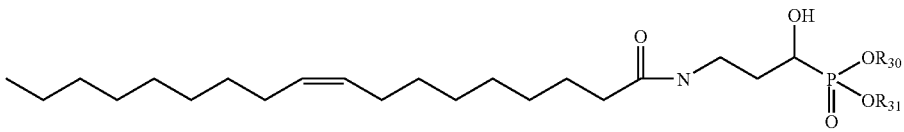

wherein $R_{30}$ and $R_{31}$ are independently selected from the group consisting of $C_1$-$C_2$ alkoxy,

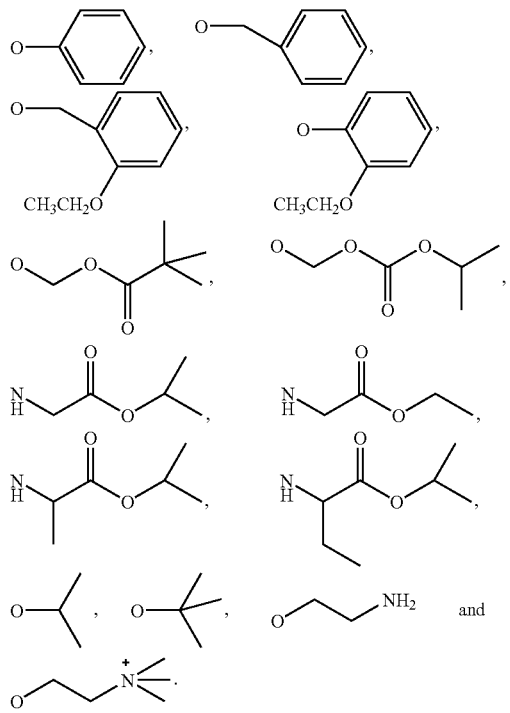

NOHPP inhibits LPP activity to varying degrees, and is a receptor subtype selective LPA mimetic. Specifically, NOHPP is fully efficacious (compared to LPA) at the LPA1 and LPA2 receptors, but has little activity at the LPA3 receptor. NOHPP is about one log order less potent than 1-oleoyl LPA at both the LPA1 and LPA2 but greater than two log orders less potent at LPA3. Since the LPA receptor LPA3 has been reported to be less responsive to LPA with saturated acyl groups (Bandoh et al. (1999) J. Biol. Chem. vol. 274, pp. 27776-27785), NOHPP with a palmitoyl group (16:0) might have even greater selectivity for LPA1 and LPA2 vs. LPA3. NOHPP inhibits LPP activities with rank order potency LPP3>LPP1>>LPP2. Furthermore, the LPA analogs of the present invention may function as LPP inhibitors even though they have poor agonist LPA activity. In accordance with one embodiment the LPP resistant compounds are used as selective inhibitors of LPP activity.

In addition, further derivatives of NOHPP are encompassed within the present invention wherein the amide linkage is replaced with a urea linkage, or an ethane or butane backbone is substituted for the propane backbone in NOHPP.

In accordance with one embodiment of the present invention a new series of compounds has been prepared that are analogous to N-oleoyl ethanolamide phosphate and are LPP resistant. These LPP resistant compounds have the general structure:

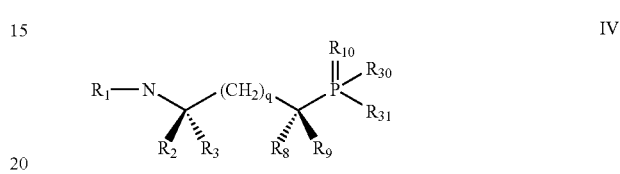

wherein $R_1$ is selected from the group consisting of $C_8$-$C_{22}$ alkyl, $C_8$-$C_{22}$ alkenyl, $C_8$-$C_{22}$ alkanoyl, $C_8$-$C_{22}$ alkenoyl, $$-\overset{O}{\underset{\|}{C}}(CH_2)_m-Z-R_{11} \text{ and } -(CH_2)_m-Z-R_{11};$$

wherein m is 0-20;

Z is selected from the group consisting of $C_3$-$C_{10}$ cycloalkyl, $C_3$-$C_{15}$ bicycloalkyl, $C_5$-$C_{10}$ heterocyclic and phenyl;

$R_{11}$ is selected from the group consisting of $C_1$-$C_{10}$ alkyl, $C_1$-$C_{20}$ alkoxyl, $C_1$-$C_{20}$ alkylthio, and $C_1$-$C_{20}$ alkylamino;

$R_2$ and $R_3$ are independently selected from the group consisting of H, hydroxy, $C_1$-$C_6$ alkyl, $C_2$-$C_4$ alkenyl, $C_2$-$C_4$ alkynyl, —($C_1$-$C_4$ alkyl)OH, —($C_1$-$C_4$ alkyl)NH$_2$, —COOR$_5$, —($C_1$-$C_4$ alkyl)COOR$_5$, —($C_1$-$C_4$ alkyl)aryl, $C_3$-$C_8$ cycloalkyl, $C_3$-$C_8$ heterocyclic, $C_7$-$C_{12}$ bicyclic, ($C_5$-$C_{10}$ alkyl)aryl, ($C_5$-$C_8$ alkenyl)aryl, ($C_5$-$C_8$ alkynyl)aryl, and n connected to phenyl with R12 and R13 substituents wherein n is 0-10;

$R_5$ is selected from the group consisting of H and $C_1$-$C_4$ alkyl;

$R_{12}$ is selected from the group consisting of halo, $C_1$-$C_{10}$ alkyl, ($C_0$-$C_{12}$ alkyl)aryl, ($C_2$-$C_{12}$ alkenyl)aryl, ($C_2$-$C_{12}$ alkynyl)aryl, —($C_1$-$C_4$ alkyl)OH, —($C_2$-$C_{12}$ alkenyl)OH, SR$_6$, SOR$_6$, NHR$_6$ and OR$_6$;

$R_{13}$ is selected from the group consisting of H, halo, $C_1$-$C_{10}$ alkyl, ($C_0$-$C_{12}$ alkyl)aryl, ($C_2$-$C_{12}$ alkenyl)aryl, ($C_2$-$C_{12}$ alkynyl)aryl, —($C_1$-$C_4$ alkyl)OH, —($C_2$-$C_{12}$ alkenyl)OH, SR$_6$, SOR$_6$, NHR$_6$ and OR$_6$;

wherein $R_6$ is selected from the group consisting of $C_1$-$C_{16}$ alkyl, $C_2$-$C_{16}$ alkenyl, $C_2$-$C_{16}$ alkynyl, —($C_1$-$C_4$ alkyl)R$_7$, —($C_2$-$C_4$ alkenyl)R$_7$, —($C_1$-$C_4$ carboxy)R$_7$ and —($C_2$-$C_4$ alynyl)R$_7$; and $R_7$ is selected from the group consisting of optionally substituted $C_3$-$C_8$ cycloalkyl, optionally substituted $C_3$-$C_8$ heterocyclic, optionally substituted $C_7$-$C_{12}$ bicyclic and optionally substituted $C_5$-$C_8$ cycloalkenyl and optionally substituted aryl, wherein the ring structures are substituted with one or more substituents selected from the group of $C_1$-$C_4$ alkyl, $C_1$-$C_4$ alkoxyl, halo, amino or hydroxy groups;

q is 0-4

$R_8$ and $R_9$ are independently selected from H, hydroxyl, amino, COOH, halo, —$PO_3$; or $R_8$ and $R_9$ taken together form a keto group or a methylene group; and $R_{10}$ is selected from the group consisting of O, S and NH and $R_{30}$ and $R_{31}$ are independently selected from the group consisting of $C_1$-$C_2$ alkoxy,

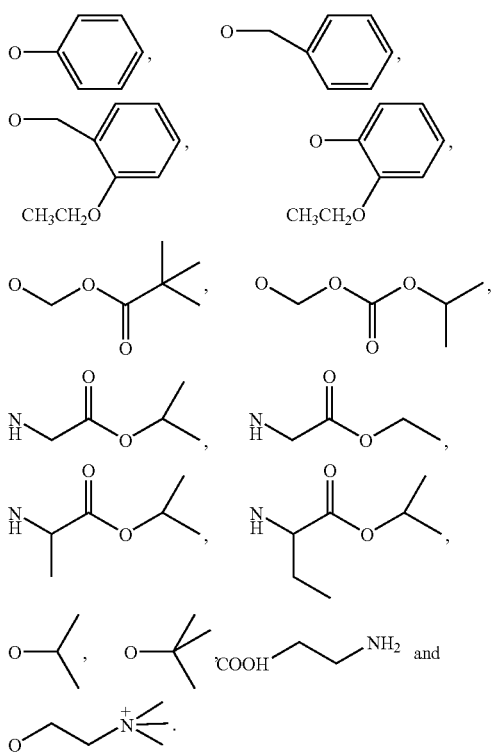

In one embodiment, $R_1$ is $C_8$-$C_{22}$ alkanoyl or $C_8$-$C_{22}$ alkenoyl, $R_2$ and $R_3$ are selected from the group hydroxy, $C_1$-$C_6$ alkyl, $C_2$-$C_4$ alkenyl, $C_2$-$C_4$ alkynyl, —($C_1$-$C_4$ alkyl)OH, —($C_1$-$C_4$ alkyl)NH$_2$, —COOR$_5$ or

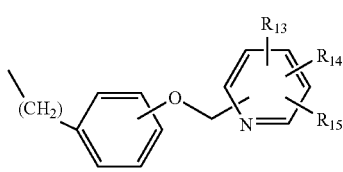

with the proviso that $R_2$ or $R_3$ is H;

$R_{13}$, $R_{14}$ and $R_{15}$ are independently selected from the group consisting of H, $C_1$-$C_6$ alkyl, $C_1$-$C_6$ haloalkyl and $C_1$-$C_6$ alkoxy; and q is 1.

In one embodiment of the present invention the LPP resistant LPA analogs have the general structure:

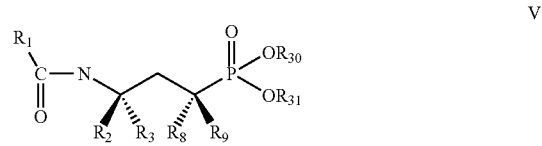

V wherein $R_1$ is selected from the group consisting of $C_8$-$C_{22}$ alkyl, $C_8$-$C_{22}$ alkenyl, substituted $C_8$-$C_{22}$ alkyl and substituted $C_8$-$C_{22}$ alkenyl;

$R_2$ and $R_3$ are independently selected from the group consisting of H, hydroxy, $C_1$-$C_6$ alkyl, $C_2$-$C_4$ alkenyl, $C_2$-$C_4$ alkynyl, —($C_1$-$C_4$ alkyl)OH, —($C_1$-$C_4$ alkyl)NH$_2$, —COOR$_5$, —($C_1$-$C_4$ alkyl)COOR$_5$, —($C_1$-$C_{10}$ alkyl)aryl and

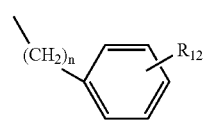

wherein n is 1-10;

$R_5$ is selected from the group consisting of H and $C_1$-$C_4$ alkyl;

$R_{12}$ is selected from the group consisting of halo, $C_1$-$C_{10}$ alkyl, ($C_0$-$C_{12}$ alkyl)aryl, ($C_2$-$C_{12}$ alkenyl)aryl, ($C_2$-$C_{12}$ alkynyl)aryl, —($C_1$-$C_4$ alkyl)OH, —($C_2$-$C_{12}$ alkenyl)OH, SR$_6$, SOR$_6$, NHR$_6$ and OR$_6$;

wherein $R_6$ is selected from the group consisting of $C_1$-$C_{16}$ alkyl, $C_2$-$C_{16}$ alkenyl, $C_2$-$C_{16}$ alkynyl, —($C_1$-$C_4$ alkyl)R$_7$, —($C_2$-$C_4$ alkenyl)R$_7$, —($C_1$-$C_4$ carboxy)R$_7$ and —($C_2$-$C_4$ alkynyl)R$_7$; and $R_7$ is selected from the group consisting of optionally substituted $C_3$-$C_8$ cycloalkyl, optionally substituted $C_3$-$C_8$ heterocyclic, optionally substituted $C_7$-$C_{12}$ bicyclic and optionally substituted $C_5$-$C_8$ cycloalkenyl, optionally substituted $C_5$-$C_8$ aryl and optionally substituted $C_5$-$C_8$ heteroaryl, wherein the ring structures are substituted with one or more substituents selected from the group of $C_1$-$C_4$ alkyl, $C_1$-$C_4$ alkoxyl, halo, amino or hydroxy groups; and $R_8$ and $R_9$ are independently selected from H, hydroxyl, amino, COOH, halo, —$PO_3$; or $R_8$ and $R_9$ taken together form a keto group or a methylene group, and $R_{30}$ and $R_{31}$ are independently selected from the group consisting of $C_1$-$C_2$ alkoxy,

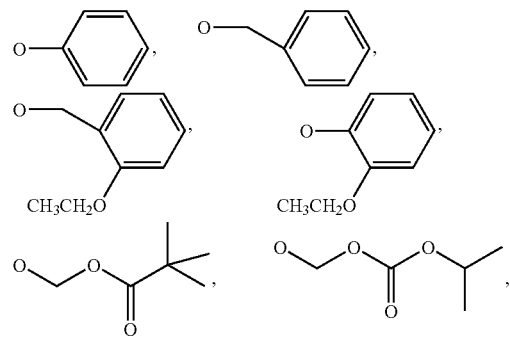

-continued

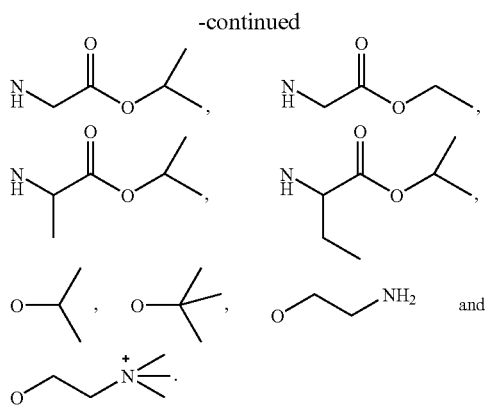

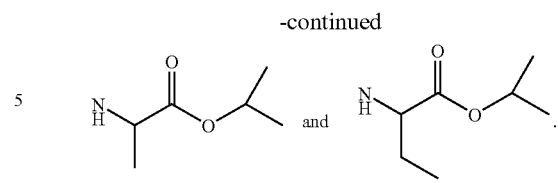

In one embodiment, $R_1$ is $C_{13}$-$C_{17}$ alkyl or $C_{17}$-$C_{21}$ alkenyl, and in one embodiment $R_1$ is a 15:0, 17:0, 17:1, 19:4 or 21:6 hydrocarbon and $R_{30}$ and $R_{31}$ are independently selected from the group consisting of

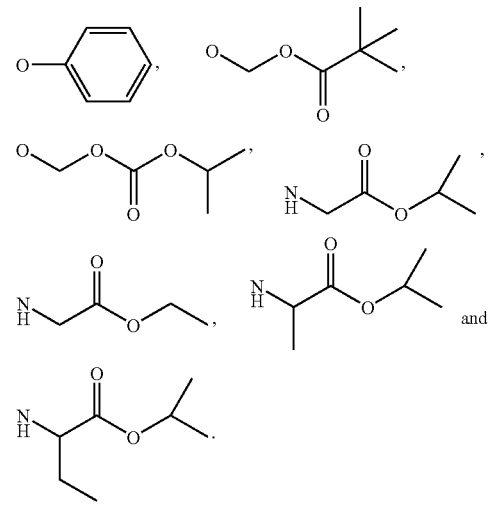

In one embodiment of the present invention the LPP resistant LPA analogs have the general structure of Formula V, wherein $R_1$ is selected from the group consisting of $C_8$-$C_{22}$ alkyl, $C_8$-$C_{22}$ alkenyl;

$R_2$ and $R_3$ are independently selected from the group consisting of H, hydroxy, $C_1$-$C_6$ alkyl, $C_2$-$C_4$ alkenyl, $C_2$-$C_4$ alkynyl, —($C_1$-$C_4$ alkyl)OH, —($C_1$-$C_4$ alkyl)NH$_2$, —COOR$_5$, —($C_1$-$C_4$ alkyl)COOR$_5$, —($C_1$-$C_4$ alkyl) aryl and

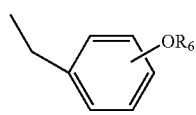

wherein $R_5$ is H or $C_1$-$C_4$ alkyl;

$R_6$ is selected from the group consisting of $C_3$-$C_{16}$ alkyl, $C_3$-$C_{16}$ alkenyl, —($C_1$-$C_4$ alkyl)$R_7$;

$R_7$ is selected from the group consisting of $C_3$-$C_8$ cycloalkyl, $C_3$-$C_8$ heterocyclic, $C_7$-$C_{12}$ bicyclic and $C_5$-$C_8$ aryl; and $R_8$ and $R_9$ are independently selected from the group consisting of H, hydroxyl, amino, COOH, halo, —PO$_3$; or $R_8$ and $R_9$ taken together form a keto group or a methylene group and $R_{30}$ and $R_{31}$ are independently selected from the group consisting of $C_1$-$C_2$ alkoxy,

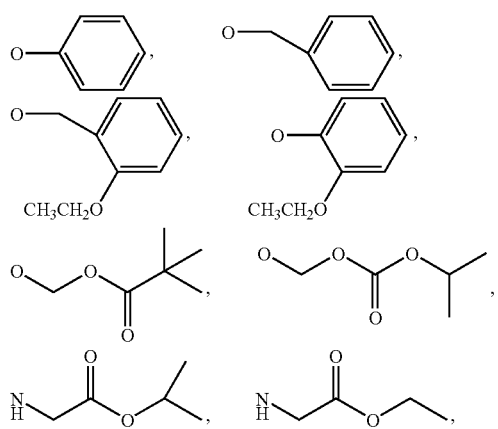

In one embodiment, the LPP resistant LPA analog has the general structure

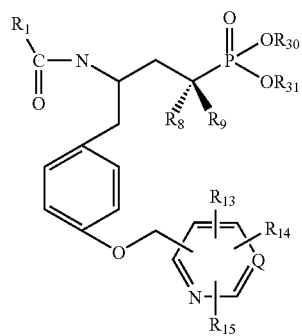

wherein $R_1$ is $C_{13}$-$C_{17}$ alkyl or $C_{17}$-$C_{21}$ alkenyl, $R_8$ and $R_9$ are independently selected from the group consisting of H, hydroxy, fluoro, or $R_8$ and $R_9$ together form a keto group; Q is selected from the group consisting of N, O, S and CHR$_{16}$;

$R_{13}$, $R_{14}$, $R_{15}$ and $R_{16}$ are independently selected from the group consisting of H, F, $C_1$-$C_6$ alkyl, $C_1$-$C_6$ haloalkyl and $C_1$-$C_6$ alkoxy;

and $R_{30}$ and $R_{31}$ are independently selected from the group consisting of $C_1$-$C_2$ alkoxy,

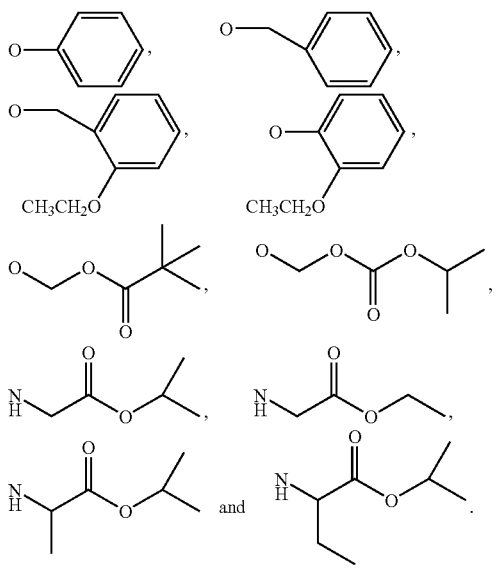

In another embodiment the compound has the general structure

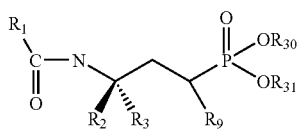

wherein $R_1$ is $C_{14}$-$C_{18}$ alkyl or $C_{18}$-$C_{22}$ alkenyl;

$R_2$ and $R_3$ are independently selected from the group consisting of H, and

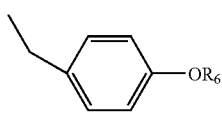

wherein $R_6$ is selected from the group consisting of $C_3$-$C_{16}$ alkyl, $C_3$-$C_{16}$ alkenyl, —($C_1$-$C_4$ alkenyl)$R_7$ and —($C_1$-$C_4$ alkyl)$R_7$;

$R_7$ is a heterocyclic substituent represented by the formula

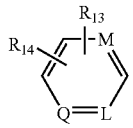

wherein L, M, and Q are selected from the group consisting of N, O, S and $CHR_{15}$, with the proviso that at least one of M, Q and L is not $CHR_{15}$;

$R_{13}$, $R_{14}$ and $R_{15}$ are independently selected from the group consisting of H, F, $C_1$-$C_6$ alkyl, $C_1$-$C_6$ haloalkyl and $C_1$-$C_6$ alkoxy;

$R_9$ is selected from the group consisting of H, hydroxyl, halo, keto and —$PO_3$ and $R_{30}$ and $R_{31}$ are independently selected from the group consisting of $C_1$-$C_2$ alkoxy,

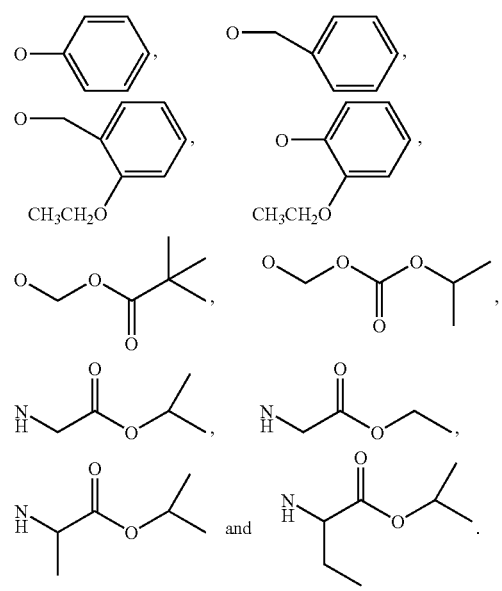

In accordance with one embodiment compounds of the present invention have the general structure:

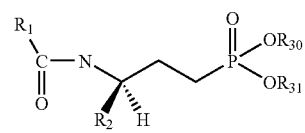

wherein $R_1$ is $C_8$-$C_{22}$ alkyl or $C_8$-$C_{22}$ alkenyl;

$R_2$ is selected from the group consisting of $C_1$-$C_6$ alkyl, —($C_1$-$C_4$ alkyl)OH, —($C_1$-$C_4$ alkyl)$NH_2$, $COOR_5$, —($C_1$-$C_4$ alkyl)$COOR_5$, and —($C_1$-$C_4$ alkyl)aryl;

$R_5$ is selected from the group consisting of H and $C_1$-$C_4$ alkyl. In one embodiment $R_1$ is $C_{13}$-$C_{17}$ alkyl or $C_{17}$-$C_{21}$ alkenyl, and $R_2$ is $C_1$-$C_4$ alkyl, methylene hydroxyl, carbomethyl, methylene amino or benzyl; and $R_{30}$ and $R_{31}$ are independently selected from the group consisting of $C_1$-$C_2$ alkoxy,

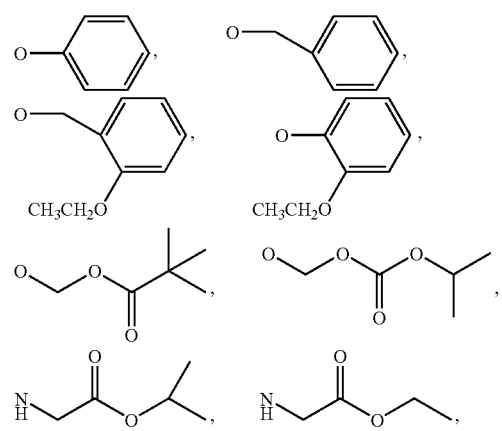

-continued

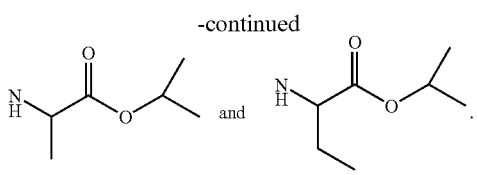

In one embodiment compounds that are based on the structure of NOHPP and fall within the scope of the present invention include the following compounds:

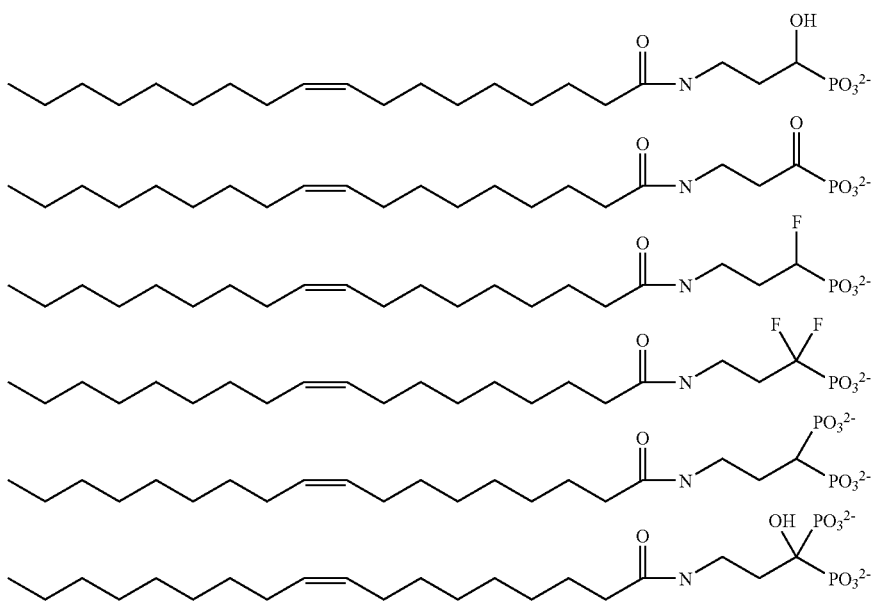

as well as phospho-ester derivatives of such compounds.

One aspect of the present invention is directed to the NOHPP analog, wls-b8L and phospho-ester derivatives and pharmaceutically acceptable salts thereof. The IUPAC name for wls-b8L is: (9Z)-N-(3-phosphonopropyl)octadec-9-enamide, and the trivial name is oleoylaminopropylphosphonate. The structure of wls-b8L is shown below:

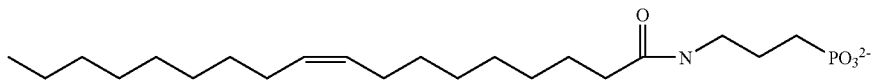

wls-b8L is expected to be resistant to hydrolysis by phosphohydrolases by virtue of its containing a phosphonate, rather than a phosphate, group. Furthermore this chemical entity (wls-b8L) has two additional desirable properties. Firstly, wls-b8L is distinctly more selective regarding its agonist activity at a single LPA receptor (LPA1) than VPC12031 (the alpha hydroxy analog of NOHPP) and VPC12060 (the alpha keto analog of NOHPP) and, secondly, at concentrations up to 10 micromolar, wls-b8L does not elicit aggregation of human platelets.

The novel LPA receptor agonists disclosed in the present invention are anticipated to have utility in a variety of clinical settings including but not limited to the acceleration of wound healing (including corneal wounds), the promotion of myelination (oligodendrocyte cell function) and for immunomodulation. In particular, LPA has been reported (Balazs et al. *Am J Physiol Regul Integr Comp Physiol*, 2001 280(2): R466-472) as having activity in accelerating wound closing and increasing neoepithelial thickness. Accordingly; one embodiment of the present invention comprises administering a pharmaceutical composition comprising one or more of the LPA receptor agonists of the present invention to a mammalian species (including humans) to treat a wound, improve neuronal function or enhance an immune response of that species. LPA has been demonstrated to induce a modest dose-dependent increase in proliferating cells, and a marked increase in the immigration of histiocyte-macrophage cells. Accordingly, in one embodiment compositions comprising an LPA receptor agonist is used to treat wounds, including burns, cuts, lacerations, surgical incisions, bed sores, and slow-healing ulcers such as those seen in diabetics. In one embodiment a composition comprising an LPA agonist is administered to a patient to enhance wound repair. Typically the composition is administered locally as a topical formulation, however other standard routes of administration are also acceptable.

The investigation of various 2-substitutions revealed several trends (see Example 2, Table 1) in a series of compounds having the general structure of Formula I, wherein $R_1$ is a 17:1 hydrocarbon and $R_4$ is $OPO_3^{-2}$. First, each LPA receptor showed a marked (one log order or more) preference for one enantiomer. Second, most substitutions were well tolerated in that they resulted in agonist ligands. Third, the LPA3 receptor, unlike LPA1 and LPA2, differentiates between unsaturated and saturated acyl groups and that LPA3 appears to have a lower affinity for LPA and LPA analogs.

Although most active compounds were partial agonists with reduced potency (relative to LPA), the R-methyl compound (VPC12086) is notable in that it is more potent and efficacious than LPA at $LPA_1$. A pattern observed with all three LPA receptors was that the R configuration was more potent with all substituents, an exception is VPC31139, which is more active in the S configuration. These data indicate that each receptor has a single spatial region within the ligand binding site.

In accordance with one embodiment an LPA receptor agonist is provided having the general structure

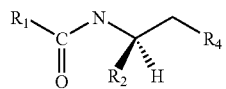

wherein $R_1$ is selected from the group consisting of $C_8$-$C_{22}$ alkyl, $C_8$-$C_{22}$ alkenyl, substituted $C_8$-$C_{22}$ alkyl and substituted $C_8$-$C_{22}$ alkenyl;

$R_2$ is selected from the group consisting of $C_1$-$C_4$ alkyl, $C_2$-$C_4$ alkenyl, $C_2$-$C_4$ alkynyl, —($C_1$-$C_4$ alkyl)OH, —($C_1$-$C_4$ alkyl)$NH_2$, —($C_1$-$C_4$ alkyl)$COOR_5$, —($C_0$-$C_{10}$ alkyl)aryl and

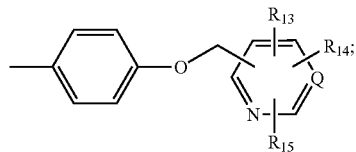

wherein Q is selected from the group consisting of N, O, S and $CHR_{15}$;

$R_{13}$, $R_{14}$ and $R_{15}$ are independently selected from the group consisting of H, $C_1$-$C_6$ alkyl, $C_1$-$C_6$ haloalkyl and $C_1$-$C_6$ alkoxy;

$R_4$ is represented by the formula

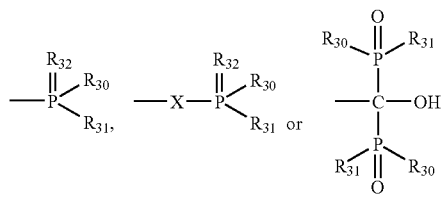

wherein $R_{32}$ is O or S;

X is selected from the group consisting of O, NH, S, $CH_2$, CHOH, $CO_2H$, CHF, $CF_2$, and

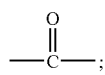

and $R_{30}$ and $R_{31}$ are independently selected from the group consisting of $C_1$-$C_2$ alkoxy,

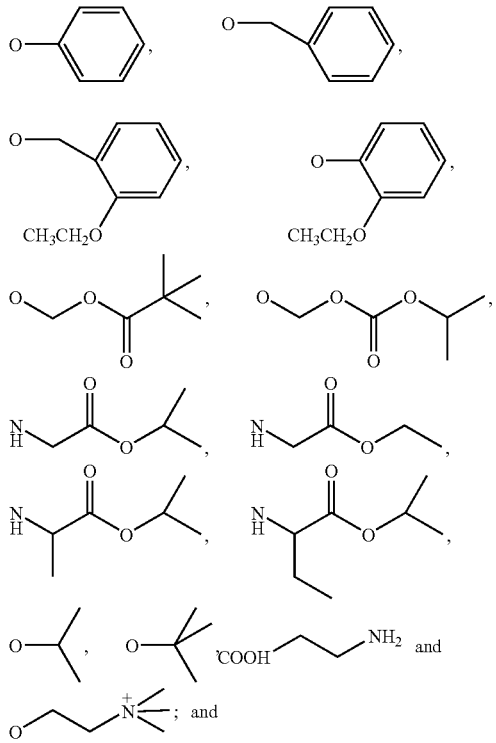

$R_5$ is selected from the group consisting of H and $C_1$-$C_4$ alkyl.

In one embodiment the compound has the general structure:

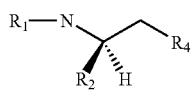

wherein $R_1$ is a saturated or unsaturated, substituted or non-substituted, straight or branched chain alkyl of about 8 to 22 carbon atoms where the #1 carbon may be in the form of a carbonyl group (C=O), i.e. the alkyl chain is joined by an amide linkage. In certain embodiments, $R_1$ is oleic acid (18:1) or palmitic acid (16:0) combined in an amide linkage; $R_2$ is methyl, ethyl, propyl, isopropyl, butyl, methylene hydroxy, methylene amino, methylene alkyne, phenyl, benzyl, methylene furan, methylene-2-naphthalene; and $R_4$ is hydroxyl (OH), phosphate ($PO_4$), or methylene phosphonate ($CH_2PO_3$). When $R_4$ is methylene phosphonate, the carbon alpha to the phosphorus can be optionally substituted with an hydroxyl, keto, fluoro or phosphonate moieties or di-substituted with fluoro or hydroxy and phosphonate substituents, and in further embodiments where $R_4$ is a phospho-ester of the general structure

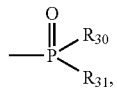

wherein $R_{30}$ and $R_{31}$ are independently selected from the group consisting of $C_1$-$C_2$ alkoxy,

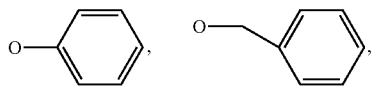

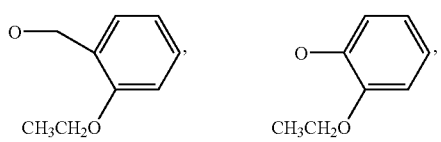

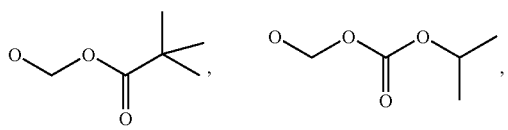

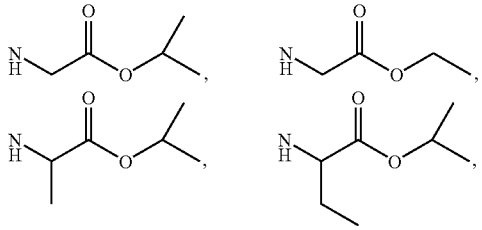

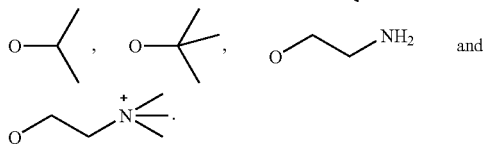

In accordance with one embodiment the LPA receptor agonist is provided having the general structure:

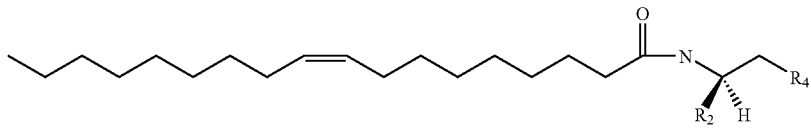

wherein $R_2$ is methyl, ethyl, propyl, isopropyl, butyl, methylene hydroxy, methylene amino, methylene alkyne, phenyl, benzyl, methylene furan, methylene-2-naphthalene or ; and $R_4$ is a phospho-ester of the general structure

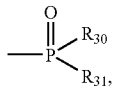

wherein $R_{30}$ and $R_{31}$ are independently selected from the group consisting of $C_1$-$C_2$ alkoxy,

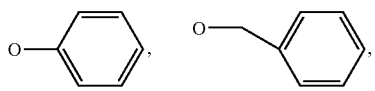

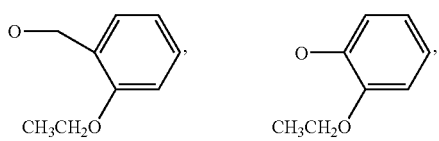

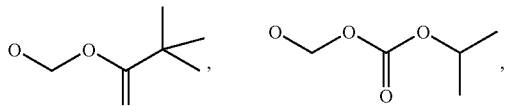

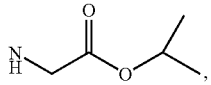 -continued

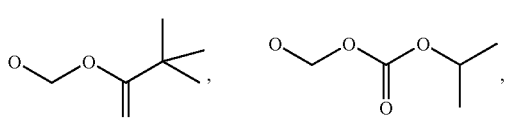

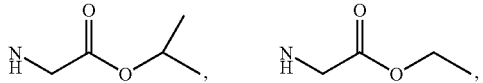

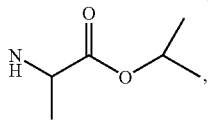

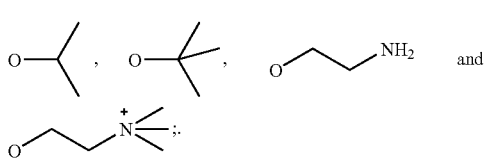

In accordance with one embodiment the LPA receptor agonist is provided having the general structure:

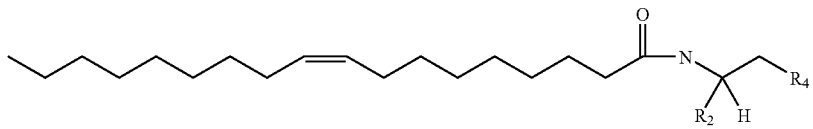

wherein $R_2$ is

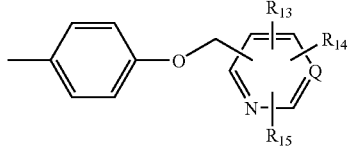

Q is selected from the group consisting of N, O, S and $CHR_{16}$;

$R_{13}$, $R_{14}$, $R_{15}$ and $R_{16}$ are independently selected from the group consisting of H, $C_1$-$C_6$ alkyl, $C_1$-$C_6$ haloalkyl and $C_1$-$C_6$ alkoxy;

$R_4$ selected from the group consisting of

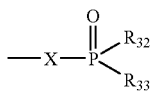

wherein X is selected from the group consisting of O, S, CHOH, $CR_{17}R_{18}$ and

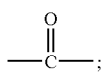

wherein $R_{17}$ and $R_{18}$ are independently H or F; and $R_{32}$ and $R_{33}$ are independently selected from the group consisting of hydroxy, $C_1$-$C_2$ alkoxy,

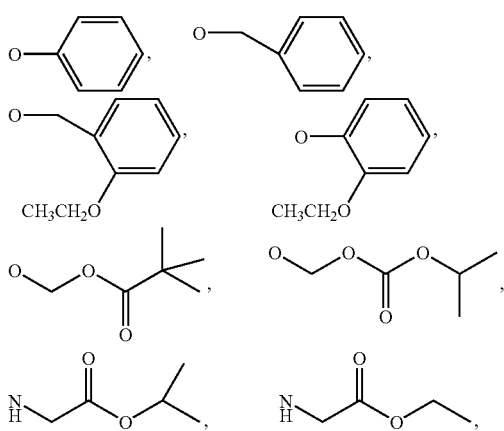

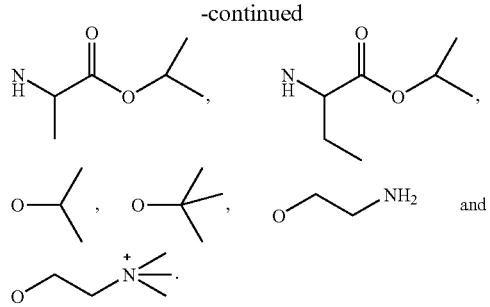

In accordance with one embodiment of the present invention LPA receptor subtype-selective compounds having agonist and/or antagonist properties can be administered to a subject to treat or prevent a disorder of abnormal cell growth and differentiation. These disorders include, but are not limited to, Alzheimer's disease, aberrant corpus luteum formation, osteoarthritis, osteoporosis, anovulation, Parkinson's disease, multiple sclerosis and rheumatoid arthritis.

As noted above LPA3 has a lower affinity for LPA and LPA analogs. It is believed that LPA3 may play a role in feedback inhibition of activity at LPA1 and LPA2. Therefore it is anticipated that an LPA3 subtype-selective agonist can be used to decrease LPA1 and LPA2 mediated activities. Thus in accordance with one embodiment an LPA3 subtype-selective agonist can be administered to a subject to treat or prevent a disorder of abnormal cell growth and differentiation, including cancer. To be considered a subtype selective agonist/antagonist, the compound should be 10× more potent, and more preferably 100× more potent, at the preferred LPA receptor. For example, it appears that mono-unsaturated substituents at $R_1$ of the LPA receptor analogs of Formula I are significantly more potent (equipotent to LPA) than the saturated compound at LPA3. LPA1 and LPA2 do not exhibit this selectivity for unsaturated vs. saturated side chains.

Similarly LPA receptor antagonist can also be used to inhibit LPA mediated activities and thus treat disorders of abnormal cell growth and differentiation as well as inflammatory diseases. These disorders include, but are not limited to, Alzheimer's disease, aberrant corpus luteum formation, osteoarthritis, osteoporosis, anovulation, Parkinson's disease, multiple sclerosis, rheumatoid arthritis and treatment of cancer. Such antagonists can then be formulated as pharmaceutical compositions using standard pharmaceutically acceptable carriers, fillers, solubilizing agents and stabilizers known to those skilled in the art. Pharmaceutical compositions comprising the LPA receptor subtype-selective agonist and/or antagonist are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment LPA receptor antagonists are provided, wherein the antagonists have the general structure

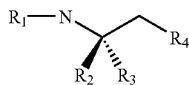

wherein $R_1$ is selected from the group consisting of $C_8$-$C_{22}$ alkyl, $C_8$-$C_{22}$ alkenyl, $C_8$-$C_{22}$ alkanoyl, $C_8$-$C_{22}$ alkenoyl,

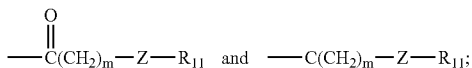

wherein m is 0-20;

Z is selected from the group consisting of $C_3$-$C_{10}$ cycloalkyl, $C_3$-$C_{15}$ bicycloalkyl, $C_5$-$C_{10}$ heterocyclic and phenyl;

$R_{11}$ is selected from the group consisting of $C_1$-$C_{10}$ alkyl, $C_1$-$C_{20}$ alkoxyl, $C_1$-$C_{20}$ alkylthio, and $C_1$-$C_{20}$ alkylamino;

$R_2$ and $R_3$ are independently selected from the group consisting of H, and

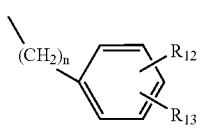

wherein n is 0-10;

$R_{12}$ is selected from the group consisting of $C_1$-$C_{10}$ alkyl, ($C_0$-$C_{12}$ alkyl)aryl, ($C_2$-$C_{12}$ alkenyl)aryl, ($C_2$-$C_{12}$ alkynyl)aryl, —($C_1$-$C_4$ alkyl)OH, —($C_2$-$C_{12}$ alkenyl)OH, $SR_6$, $SOR_6$, $NHR_6$ and $OR_6$;

$R_{13}$ is selected from the group consisting of H, $C_1$-$C_{10}$ alkyl, ($C_0$-$C_{12}$ alkyl)aryl, ($C_2$-$C_{12}$ alkenyl)aryl, ($C_2$-$C_{12}$ alkynyl)aryl, —($C_1$-$C_4$ alkyl)OH, —($C_2$-$C_{12}$ alkenyl)OH, phenyl-4-methoxy, $SR_6$, $SOR_6$, $NHR_6$ and $OR_6$;

wherein $R_6$ is selected from the group consisting of $C_1$-$C_{16}$ alkyl, $C_2$-$C_{16}$ alkenyl, $C_2$-$C_{16}$ alkynyl, —($C_1$-$C_4$ alkyl)$R_7$, —($C_2$-$C_4$ alkenyl)$R_7$, —($C_1$-$C_4$ carboxy)$R_7$ and —($C_2$-$C_4$ alkynyl)$R_7$;

$R_7$ is selected from the group consisting of optionally substituted $C_3$-$C_8$ cycloalkyl, optionally substituted $C_3$-$C_8$ heterocyclic, optionally substituted $C_7$-$C_{12}$ bicyclic, optionally substituted $C_5$-$C_8$ cycloalkenyl and optionally substituted aryl; and $R_4$ is

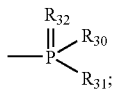

wherein $R_{32}$ is selected from the group consisting of O and S;

and $R_{30}$ and $R_{31}$ are independently selected from the group consisting of

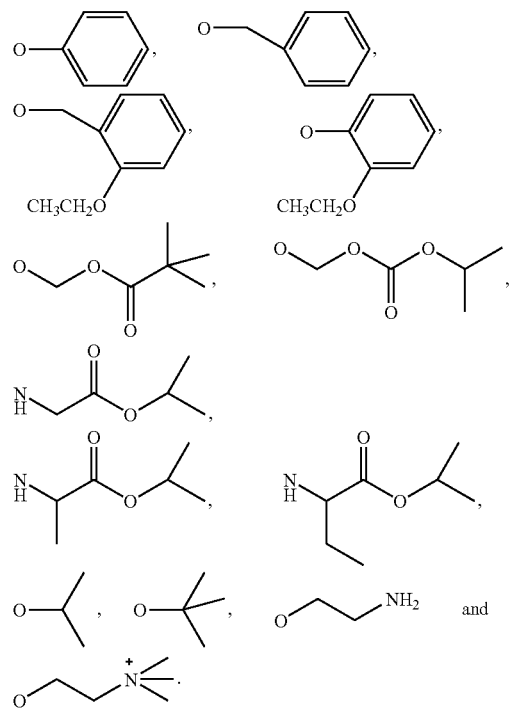

In one embodiment n is 1, $R_{13}$ is H and $R_{12}$ is $SR_6$, $SOR_6$, $NHR_6$ or $OR_6$.

In accordance with one embodiment LPA receptor antagonists are provided, wherein the antagonists have the general structure

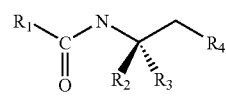

wherein $R_1$ is selected from the group consisting of $C_8$-$C_{22}$ alkyl, $C_8$-$C_{22}$ alkenyl, substituted $C_8$-$C_{22}$ alkyl and substituted $C_8$-$C_{22}$ alkenyl;

$R_2$ and $R_3$ are independently selected from the group consisting of H, and

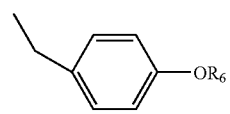

wherein $R_6$ is selected from the group consisting of $C_3$-$C_{16}$ alkyl, $C_3$-$C_{16}$ alkenyl, —($C_1$-$C_4$ alkenyl)$R_7$, —($C_2$-$C_4$ alkynyl)$R_7$ and —($C_2$-$C_4$ alkyl)$R_7$;

$R_7$ is

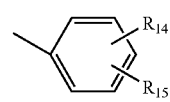

wherein $R_{14}$ and $R_{15}$ are independently selected from the group consisting of H, $C_1$-$C_{12}$ alkyl, $C_2$-$C_6$ alkenyl, $C_2$-$C_6$ alkynyl, halo; and $R_4$ is

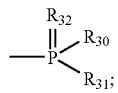

wherein $R_{32}$ is selected from the group consisting of O and S;

and $R_{30}$ and $R_{31}$ are independently selected from the group consisting of

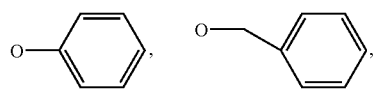

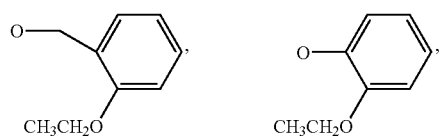

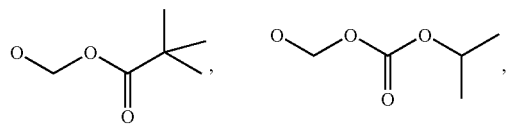

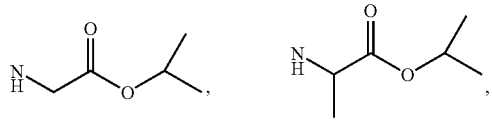

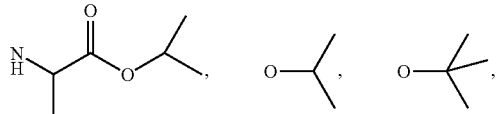

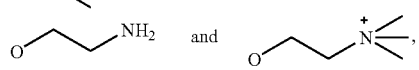

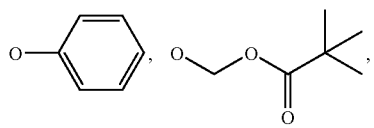

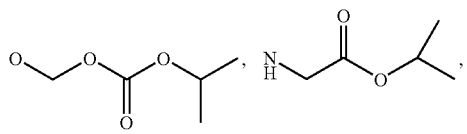

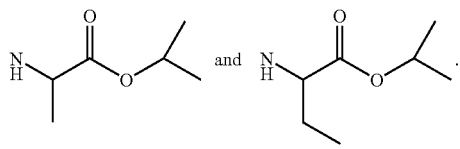

In one embodiment $R_1$ is a 15:0, 17:0, 17:1, 19:4 or 21:6 hydrocarbon and $R_4$ is

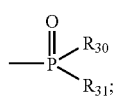

wherein $R_{30}$ and $R_{31}$ are independently selected from the group consisting of

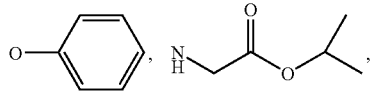

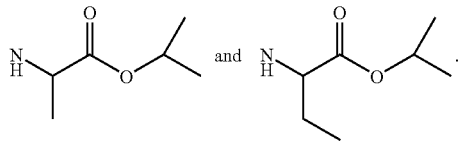

In accordance with one embodiment the LPA receptor antagonist has the general structure:

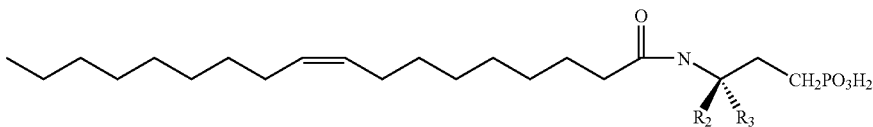

with the proviso that $R_2$ and $R_3$ are not both H. In one embodiment, $R_1$ is $C_{13}$-$C_{17}$ alkyl or $C_{17}$-$C_{21}$ alkenyl and $R_4$ is

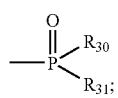

wherein $R_{30}$ and $R_{31}$ are independently selected from the group consisting of wherein $R_2$ and $R_3$ are independently selected from the group consisting of H, benzyl, methylene furan, methylene-2-naphthalene, methylene phenyl-4-O-benzyl, methylene phenyl-4-benzyl, methylene phenyl-4-chloro, methylene phenyl-4-trans-styrene, methylene phenyl-4-cis-styrene, methylene phenyl-4-O-2,6-dichlorobenzyl and methylene phenyl-4-phenyl. In one embodiment $R_2$ is H and the compound is prepared as a phospho-ester derivatives thereof.

Additional compounds that serve as antagonists of LPA receptor function include compounds of the general formula:

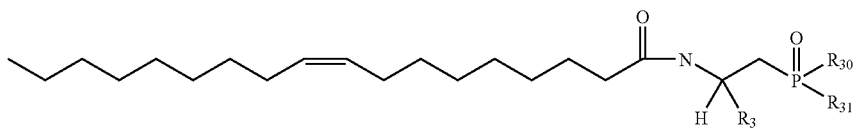
wherein $R_{30}$ and $R_{31}$ are independently selected from the group consisting of $C_1$-$C_2$ alkoxy,
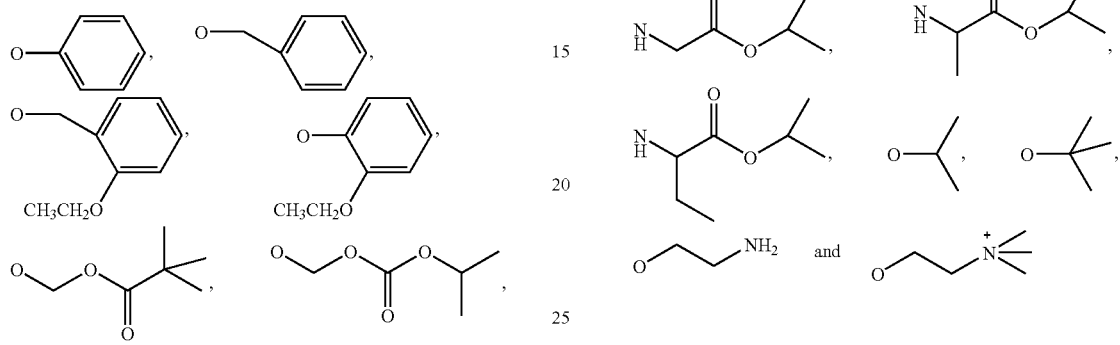
and $R_3$ is selected from the group:
| | Compound name and Stereochemistry | |
|---|---|---|
| | (R) | (S) |
| 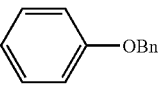 | VPC12204 | VPC12249 |
| 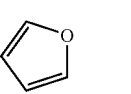 | VPC12250 | VPC12229 |
| 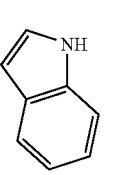 | VPC12193 | VPC12227 |
| 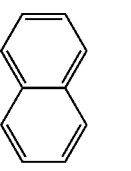 | VPC12235 | VPC12228 |
| 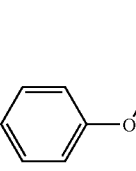 | VPC12284 | |
| 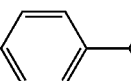 | VPC13061 | VPC13082 |

| -continued |
| Compound name and Stereochemistry |

| | (R) | (S) |
|---|---|---|
| 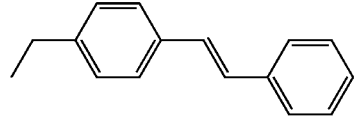 | VPC13063 | VPC13086 |
| 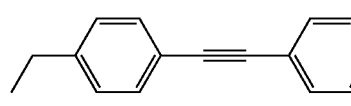 | VPC13066 | |
| 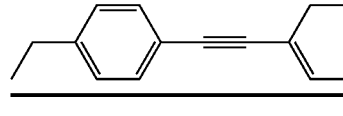 | VPC13069 | VPC13089 |

One example of an LPA antagonist in accordance with the present invention is VPC12249. That compound, having the backbone structure of Formula II, wherein $R_1$ is a 17:1 hydrocarbon, $R_2$ is H, $R_4$ is $OPO_3^{-2}$ (or a phosphos-ester or pharmaceutically acceptable salt thereof) and $R_3$ contains the benzyl-4-oxybenzyl functionality in the S-configuration, which confers antagonistic activity at LPA1 and LPA3 receptors. VPC12249, to our knowledge, is the first specific LPA1/LPA3 receptor antagonist. This compound possesses high affinity for the LPA1 (ca. KI 130 nM) and LPA3 (ca. KI=425 nM) receptors. In addition compound VPC31162 (structure of Formula II, wherein $R_1$ is a 17:1 hydrocarbon, $R_2$ is H, $R_4$ is $OPO_3^{-2}$ (or a phosphos-ester or pharmaceutically acceptable salt thereof) and $R_3$ is benzyl-4-oxybenzyl-4-pentane) has antagonist activity at the LPA2 receptor, but is an agonist at LPA1 and LPA3.

In accordance with one embodiment of the present invention the LPA analogs that exhibit LPA receptor antagonist activity can be used to treat ischemia reperfusion type injury. Interference with the supply of oxygenated blood to tissues is defined as ischemia. The effects of ischemia are known to be progressive, such that over time cellular vitality continues to deteriorate and tissues become necrotic. Total persistent ischemia, with limited oxygen perfusion of tissues, results in cell death and eventually in coagulation-induced necrosis despite reperfusion with arterial blood. A substantial body of evidence indicates that a significant proportion of the injury associated with ischemia is a consequence of the events associated with reperfusion of ischemic tissues, hence the term reperfusion injury.

To place reperfusion injury into a clinical perspective, there are three different degrees of cell injury, depending on the duration of ischemia: (1) With short periods of ischemia, reperfusion (and resupply of oxygen) completely restores the structural and functional integrity of the cell. Whatever degree of injury the cells have incurred can be completely reversed upon reoxygenation. (2) With longer periods of ischemia, reperfusion is not associated with the restoration of cell structure and function, but rather with deterioration and death of cells. The response to reoxygenation in this case is rapid and intense inflammation. (3) Lethal cell injury may develop during prolonged periods of ischemia, where reperfusion is not a factor. The reversibility of cell injury as a consequence of ischemia is determined not only by the type and duration of the injury, but also by the cell target. Neurons exhibit very high sensitivity to ischemia, whereas myocardial, pulmonary, hepatic and renal tissues are intermediate in sensitivity. Fibroblasts, epidermis and skeletal muscle have the lowest susceptibility to ischemic injury, requiring several hours without blood supply to develop irreversible damage.

In accordance with the present invention a compound having the general structure:

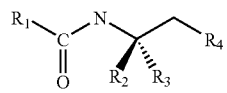

wherein $R_1$ is selected from the group consisting of $C_8$-$C_{22}$ alkyl, $C_8$-$C_{22}$ alkenyl, substituted $C_8$-$C_{22}$ alkyl and substituted $C_8$-$C_{22}$ alkenyl;

$R_2$ and $R_3$ are independently selected from the group consisting of H, and

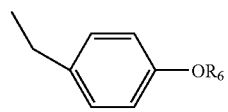

wherein $R_6$ is selected from the group consisting of $C_3$-$C_{16}$ alkyl, $C_3$-$C_{16}$ alkenyl, —($C_1$-$C_4$ alkenyl)$R_7$, —($C_2$-$C_4$ alkynyl)$R_7$ and —($C_2$-$C_4$ alkyl)$R_7$;

$R_7$ is

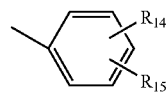

wherein $R_{14}$ and $R_{15}$ are independently selected from the group consisting of H, $C_1$-$C_{12}$ alkyl, $C_2$-$C_6$ alkenyl, $C_2$-$C_6$ alkynyl, halo; and $R_4$ is

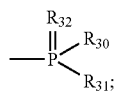

wherein $R_{32}$ is selected from the group consisting of O and S;

and $R_{30}$ and $R_{31}$ are independently selected from the group consisting of

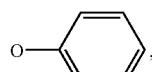 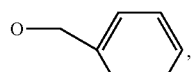

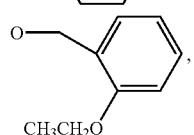 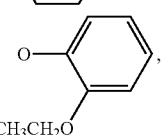

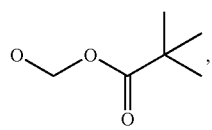 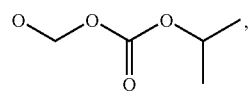

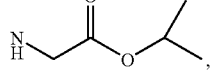 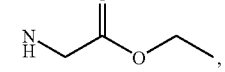

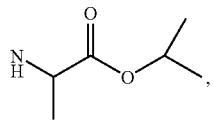 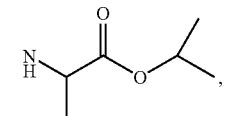

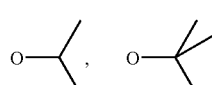 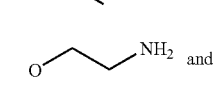

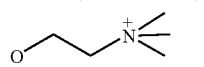

with the proviso that $R_2$ and $R_3$ are not both H is administered to reduce of prevent reperfusion injury. In one embodiment, $R_1$ is $C_{13}$-$C_{17}$ alkyl or $C_{17}$-$C_{21}$ alkenyl and $R_4$ is

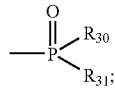

wherein $R_{30}$ and $R_{31}$ are independently selected from the group consisting of

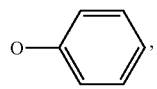 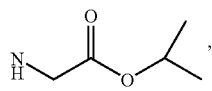

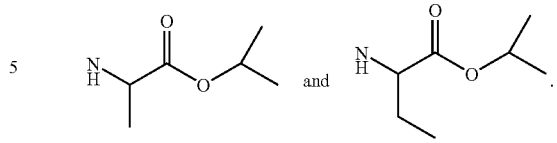

In one embodiment $R_1$ is a 15:0, 17:0, 17:1, 19:4 or 21:6 hydrocarbon and $R_4$ is

wherein $R_{30}$ and $R_{31}$ are independently selected from the group consisting of

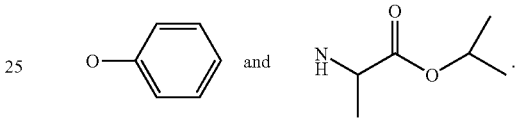

In one embodiment the compound is VPC12249.

The LPA receptor antagonist of the present invention can be formulated with pharmaceutically acceptable carriers, diluents, and solubilizing agents for administration to patient in need of such therapy. The compounds are preferably administered intravenously, but any standard route of administration is acceptable including oral delivery. In particular, if the LPA receptor antagonist is administered prior to tissue injury, such as to a patient prior to surgery, the LPA receptor antagonist can be administered orally.

In one embodiment a therapeutically effective amount of the LPA receptor antagonist is administered intravenously in a physiologically acceptable carrier as early as possible, and most preferably within four hours of a reperfusion injury. Subsequent doses of the LPA receptor antagonist, can be administered intravenously or orally.

EXAMPLE 1

Synthesis of 2-substituted, Ethanolamide-based LPA Analogs

Chemicals for syntheses were purchased from Aldrich Chemical Company, Inc., Sigma Chemical Company, Inc., Advanced ChemTech Chemical Company, Inc. and/or NovaBiochem Chemical Company, Inc., and were used without further purification. The general approach used to synthesize the LPA analogs of the present invention is shown in Scheme 1. Briefly the seven steps are as follows:

General Procedure A: Installation of Chiral Auxillary

To a solution of carbobenzyloxy-protected amino acid in diethyl ether at −78° C. is added triethylamine followed by pivaloyl chloride. The resulting thick white precipitate is stirred for 1 hr at 0° C. and then re-cooled to −78° C. In a separate flask, a solution of [4S]-4-benzyl-2-oxaxolidinone in tetrahydrofuran (THF) is prepared. On cooling this solution to −78° C., n-butyllithium is added via a syringe over 5 minutes. The resulting solution is cannulated to the flask containing the mixed anhydride. The mixture is stirred for 15 min at −78° C. and 30 min at 0° C. before quenching by addition of aqueous ammonium chloride. The resulting solution is concentrated and diluted with methylene chloride, extracted (3×) with sodium bicarbonate and brine and dried (Na$_2$SO$_4$). The imide product is isolated by flash chromatography.

General Procedure B: Alpha-Carbon Alkylation

To a solution of imide in dichloromethane at 0° C. is added titanium tetrachloride. After stirring for 5 minutes, diisopropylethylamine is added. The solution is stirred for 3 hours at 0° C., and then the alkylbromide is added. The resulting solution is stirred for an additional 2 hours before cannulated to a vigorously stirring mixture of saturated aqueous sodium bicarbonate. The layers are separated and extracted (three times) with dichloromethane, dried (Na$_2$SO$_4$) and concentrated. The α,α-substituted product is isolated by flash chromatography.

General Procedure C: Chiral Auxiliary Removal

To a solution of α,α-substituted amino acid in THF at 0° C. is added methanol and lithium borohydride. The solution is stirred for 1 hour and quenched by the addition of 1.0M sodium potassium tartrate and stirring for 10 min at 0° C. The layers are separated and extracted (3×) with dichloromethane, dried (Na$_2$SO$_4$) and concentrated. The alcohol product is isolated by flash chromatography.

General Procedure D: Phosphorylation

To a solution of alcohol in 1:1 THF/CH$_2$Cl$_2$ in an aluminum foil covered round bottom flask is added tetrazole. After stirring for 15 minutes, di-t-butyldiisoproylphosphoramidite is added. The solution is stirred for 6 hours and quenched with sodium metabisulfite at 0° C., and extracted with ethylacetate. The organic layers are combined, dried (Na$_2$SO$_4$) and concentrated. The product is purified by flash chromatography.

General Procedure E: N-Cbz Deprotection

To a solution of Cbz-protected phosphate in ethanol is added 10% Pd/C. The resulting solution is placed under H$_2$ atmosphere. After 2 hours, the solution is filtered and concentrated to provide the product.

General Procedure F: Addition of Fatty Acid Moiety

To a solution of amine in dichloromethane is added N,N-diisopropylethylamine. After stirring for 10 minutes, oleoyl chloride is added via a syringe over 20 minutes. The resulting solution is quenched by adding saturated aqueous ammonium chloride after 1 hour. The aqueous layer is extracted (3×) with ethyl acetate and the combined organic layers are dried (Na$_2$SO$_4$) and concentrated. The product is purified by flash chromatography.

General Procedure G: Phosphate Deprotection

To a solution of protected phosphate in dichloromethane is added trifluoroacetic acid. After 2 hours, the solvent is removed via rotary evaporation and ether is added and removed. This process is repeated until the all trifluoroacetic acid is removed, providing the phosphate deprotected product.

Additional synthetic details are provided in the following:

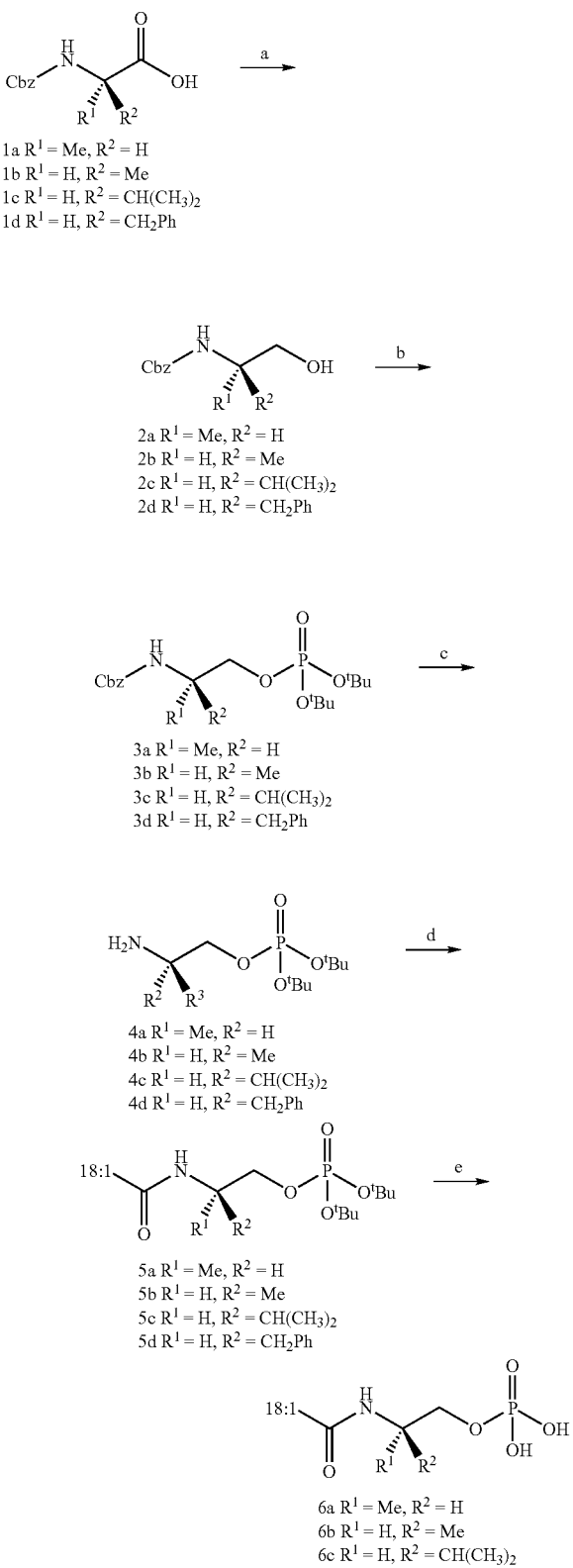

Scheme 1

1a R$^1$ = Me, R$^2$ = H
1b R$^1$ = H, R$^2$ = Me
1c R$^1$ = H, R$^2$ = CH(CH$_3$)$_2$
1d R$^1$ = H, R$^2$ = CH$_2$Ph

2a R$^1$ = Me, R$^2$ = H
2b R$^1$ = H, R$^2$ = Me
2c R$^1$ = H, R$^2$ = CH(CH$_3$)$_2$
2d R$^1$ = H, R$^2$ = CH$_2$Ph

3a R$^1$ = Me, R$^2$ = H
3b R$^1$ = H, R$^2$ = Me
3c R$^1$ = H, R$^2$ = CH(CH$_3$)$_2$
3d R$^1$ = H, R$^2$ = CH$_2$Ph

4a R$^1$ = Me, R$^2$ = H
4b R$^1$ = H, R$^2$ = Me
4c R$^1$ = H, R$^2$ = CH(CH$_3$)$_2$
4d R$^1$ = H, R$^2$ = CH$_2$Ph

5a R$^1$ = Me, R$^2$ = H
5b R$^1$ = H, R$^2$ = Me
5c R$^1$ = H, R$^2$ = CH(CH$_3$)$_2$
5d R$^1$ = H, R$^2$ = CH$_2$Ph

6a R$^1$ = Me, R$^2$ = H
6b R$^1$ = H, R$^2$ = Me
6c R$^1$ = H, R$^2$ = CH(CH$_3$)$_2$
6d R$^1$ = H, R$^2$ = CH$_2$Ph

Reagents: (a) i. DIEA, isobutylchloroformate, ii. NaBH$_4$, H$_2$O; (b) 1H-Tetrazole, N,N-di-t-butyl diisopropylphosphoramidite; (c) 10% Pd/C, H$_2$; (d) Oleoyl chloride, DIEA or pyridine; (E) 1:1 TFA/CH$_2$Cl$_2$ Scheme 2

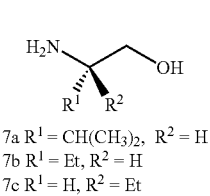

7a R¹ = CH(CH₃)₂, R² = H
7b R¹ = Et, R² = H
7c R¹ = H, R² = Et a ↓

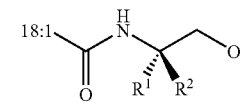

8a R¹ = CH(CH₃)₂, R² = H
8b R¹ = Et, R² = H
8c R¹ = H, R² = Et b ↓

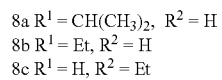

9a R¹ = CH(CH₃)₂, R² = H
9b R¹ = Et, R² = H
9c R¹ = H, R² = Et

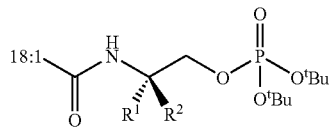

10a R¹ = CH(CH₃)₂, R² = H
10b R¹ = Et, R² = H
10c R¹ = H, R² = Et

Reagents: (a) Oleoyl chloride, DIEA or pyridine; (b) 1H-Tetrazole, N,N-di-t-butyl diisopropylphosphoramidite; (c) 1:1 TFA/CH₂Cl₂

Scheme 3

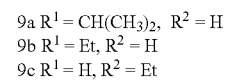

11a R¹ = CH₂Ph, R² = H
11b R¹ = R² = Me a ↓

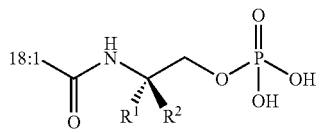

12a R¹ = CH₂Ph, R² = H
12b R¹ = R² = Me b ↓

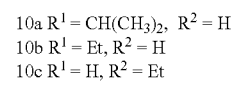

13a R¹ = CH₂Ph, R² = H
13b R¹ = R² = Me d ↓

-continued

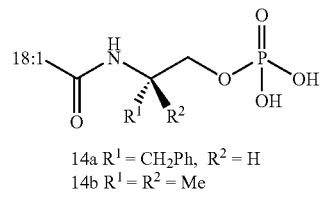

14a R¹ = CH₂Ph, R² = H
14b R¹ = R² = Me

Reagents: (a) i. DIEA, isobutylchloroformate, ii. NaBH₄, H₂O; (b) i. 1:1 TFA/CH₂Cl₂; ii. Oleoyl chloride, DIEA or pyridine; (c) 1H-Tetrazole, N,N-di-t-butyl diisopropylphosphoramidite; (d) 10% Pd/C, H₂; (e) 1:1 TFA/CH₂Cl₂

Scheme 4

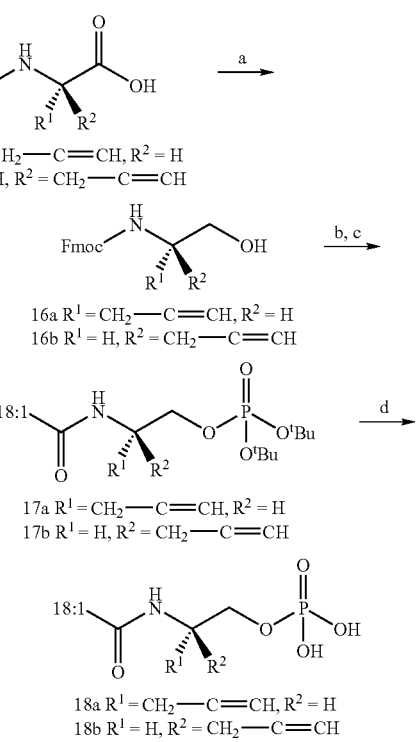

15a R¹ = CH₂—C≡CH, R² = H
15b R¹ = H, R² = CH₂—C≡CH

16a R¹ = CH₂—C≡CH, R² = H
16b R¹ = H, R² = CH₂—C≡CH

17a R¹ = CH₂—C≡CH, R² = H
17b R¹ = H, R² = CH₂—C≡CH

18a R¹ = CH₂—C≡CH, R² = H
18b R¹ = H, R² = CH₂—C≡CH

Reagents: (a) i. DIEA, isobutylchloroformate, ii. NaBH₄, H₂O; (b) 1H-Tetrazole, N,N-di-t-butyl diisopropylphosphoramidite; (b) i. 1:1 DIEA/CH₂Cl₂; ii. Oleoyl chloride; (d) 1:1 TFA/CH₂Cl₂

Scheme 5

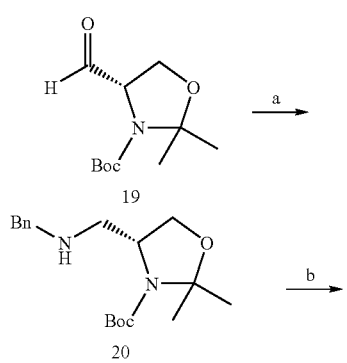

19

20

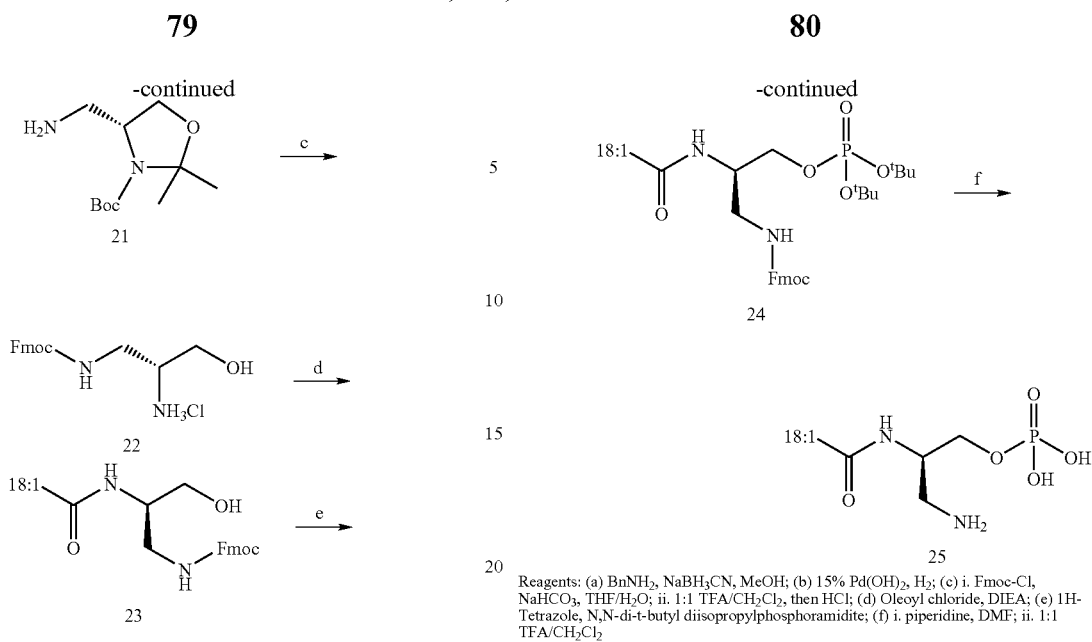
Reagents: (a) BnNH₂, NaBH₃CN, MeOH; (b) 15% Pd(OH)₂, H₂; (c) i. Fmoc-Cl, NaHCO₃, THF/H₂O; ii. 1:1 TFA/CH₂Cl₂, then HCl; (d) Oleoyl chloride, DIEA; (e) 1H-Tetrazole, N,N-di-t-butyl diisopropylphosphoramidite; (f) i. piperidine, DMF; ii. 1:1 TFA/CH₂Cl₂
Scheme 6: Synthesis of Tyronsine-based Antagonists
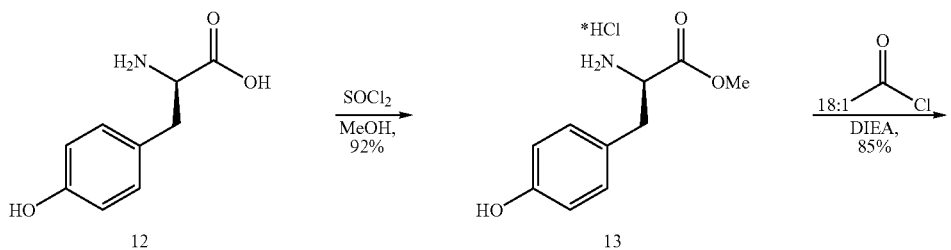
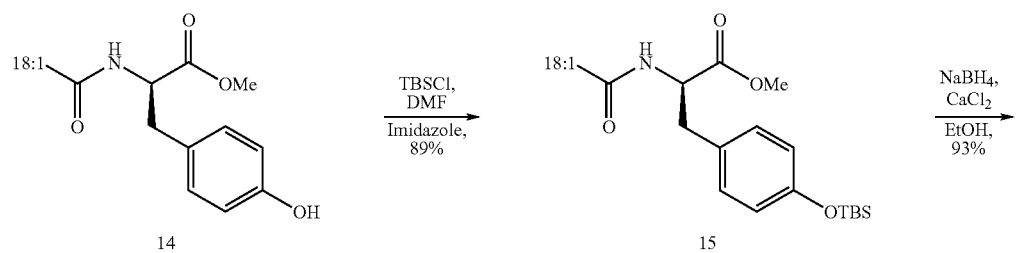
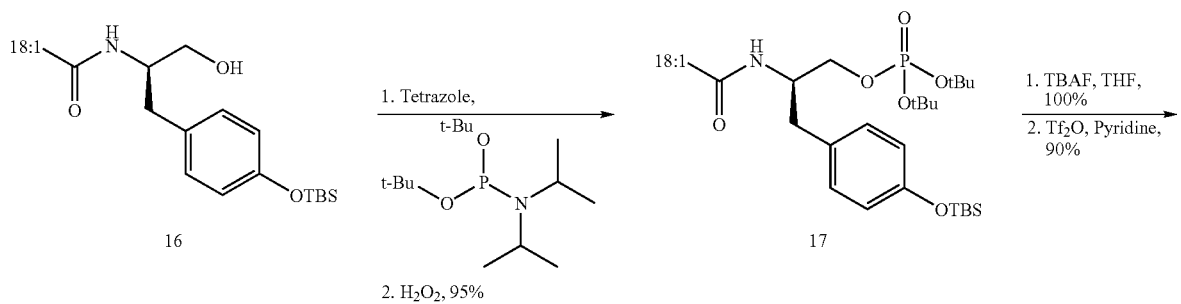

-continued
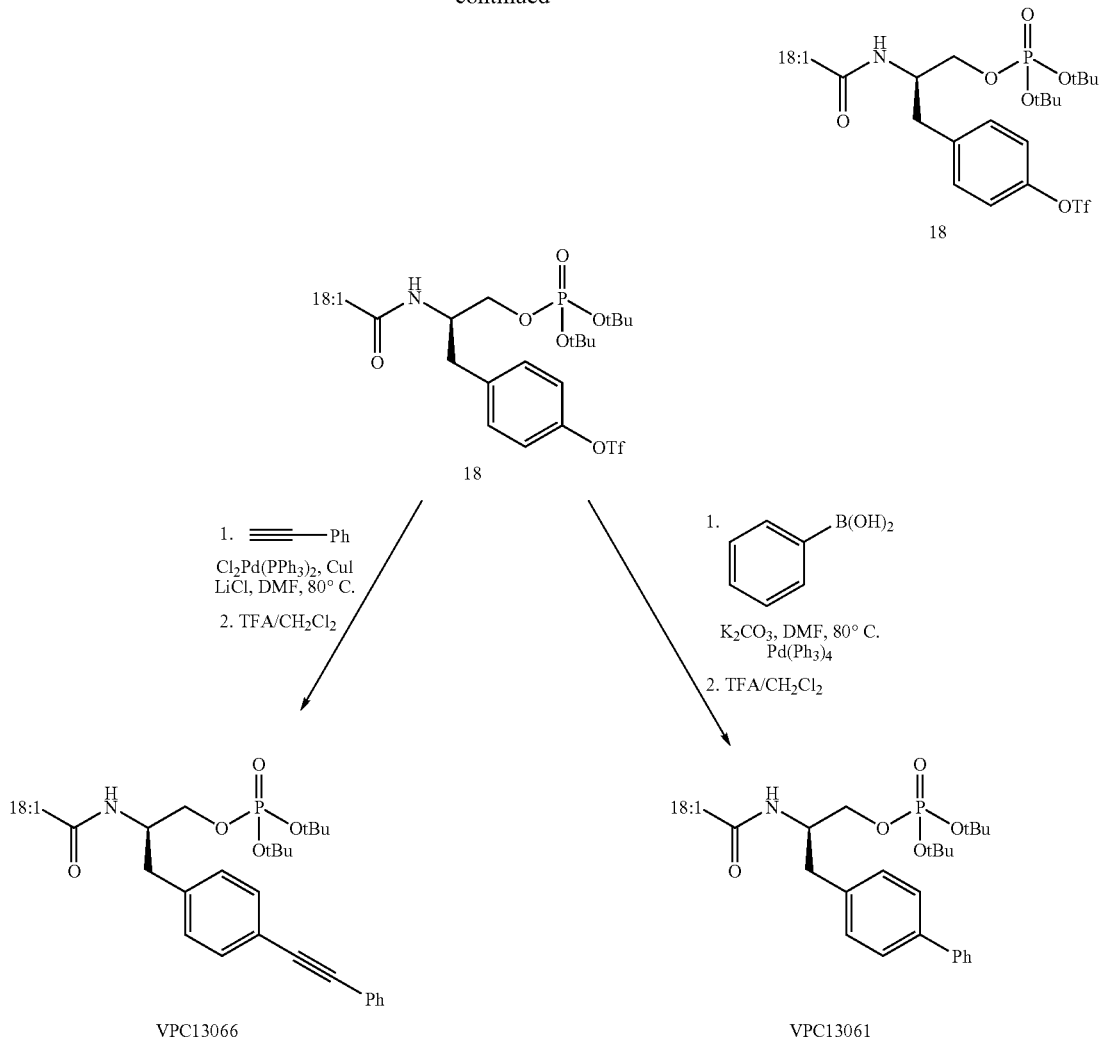
Scheme 7: Synthesis of Amino Analogs
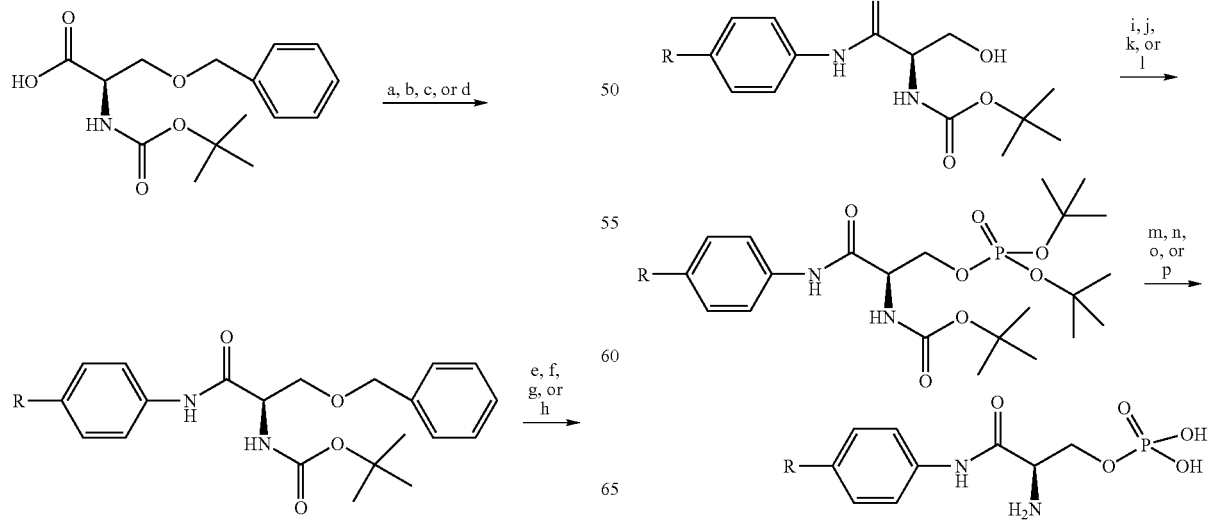

-continued a) PyBOP, DIEA, 4-hexylaniline, 77%
b) PyBOP, DIEA, 4-octylaniline, 73%
c) PyBOP, DIEA, 4-decylaniline, 65%
d) PyBOP, DIEA, 4-dodecylaniline, 71%
e) Di$^t$Bu-di$^i$Pr-phosphoramidite, tetrazole, $H_2O_2$, 85%
f) Di$^t$Bu-di$^i$Pr-phosphoramidite, tetrazole, $H_2O_2$, 60%
g) Di$^t$Bu-di$^i$Pr-phosphoramidite, tetrazole, $H_2O_2$, 70%
h) Di$^t$Bu-di$^i$Pr-phosphoramidite, tetrazole, $H_2O_2$, 9%
i) $H_2$, Pd/C, 84%
j) $H_2$, Pd/C, 96%
k) $H_2$, Pd/C, 87%
l) $H_2$, Pd/C, 90%
m) TFA, ??%
n) TFA, 58%
o) TFA, 75%
p) TFA, ??%
VPC22157: R = $(CH_2)_5CH_3$ (a, e, i, m)
VPC22173: R = $(CH_2)_7CH_3$ (b, f, l, n)
VPC22199: R = $(CH_2)_9CH_3$ (c, g, k, o)
VPC22211: R = $(CH_2)_{11}CH_3$ (d, h, l, p)

EXAMPLE 2

Activity of 2-Substituted LPA Analogs at Edg/LPA Receptors

Materials and Methods

Transient Expression in HEK293T Cells

The appropriate receptor plasmid DNA (encoding mouse LPA1, human LPA2 or human LPA3) was mixed with equal amounts of expression plasmids (pcDNA3) encoding a mutated (C351F) rat Gi2a, cow β1, and γ2 proteins and these DNAs were used to transfect monolayers of HEK293T cells (where 'T' indicates expression of the SV-40 virus large T antigen) using the calcium phosphate precipitate method. After about 60 hours, cells were harvested, membranes were prepared, aliquoted and stored at −70° C. until use.

GTP[35 γS] Binding:

The GTP[35 γS] assay was performed as described by us previously. Membranes containing 5 ug of protein were incubated in 0.1 ml GTP-binding buffer (in mM: HEPES 50, NaCl 100, MgCl2 10, pH7.5) containing 5 mg saponin, 10 mM GDP, 0.1 nM GTP[35 γS] (1200 Ci/mmol), and indicated lipid(s) for 30 minutes at 30° C. Samples were analyzed for membrane-bound radionuclide using a Brandel Cell Harvester (Gaithersburg, Md.). The C351F mutation renders the Gi2α protein resistant to inactivation by pertussis toxin or the alkylating agent N-ethylmaleimide; however in practice background binding was sufficiently low to obviate these maneuvers.

Measurement of cAMP Accumulation:

Assays for cAMP accumulation were conducted on populations of $5 \times 10^5$ cells stimulated with 10 mM forskolin in the presence of the phosphodiesterase inhibitor isomethylbutylxanthine (IBMX) for 15 minutes at 30° C. cAMP was measured by automated radioimmunoassay.

Measurement of Intracellular Calcium:

A FLIPR™ (Molecular Devices, Inc.) was used to measure intracellular calcium in A431 and HEK293T cells. A431 cells were seeded (~50,000 cells/well) in 96-well clear bottom black microplates (Corning Costar Corp., Cambridge, Mass.) and left overnight in $CO_2$ incubator at 37° C. HEK293T cells were treated likewise, but seeded onto poly D-lysine coated microplates (Becton Dickinson, Franklin Lakes, N.J.). A431 cells were dye-loaded with 4 μM Fluo-3 AM ester (Molecular Probes Inc., Eugene, Oreg.) in a loading buffer (1×HBSS buffer, pH 7.4, containing 20 mM HEPES, 0.1% BSA, and 2.5 mM probenecid) for 1 hour at 37° C. Cells were then washed four times with the loading buffer and exposed in the FLIPR™ to sets of compounds. HEK293T cells were loaded with 2 μM Fluo-4 AM ester (Molecular Probes Inc., Eugene, Oreg.) in the same loading buffer without probenecid for 30 minutes and washed four times before being exposed to compounds in the FLIPR™. In all cases, each concentration of each compound was tested in at least quintuplicate.

Determination of KI:

KI for VPC12249 in experiments were determined by plotting the log of Dose Ratio-1 at each concentration of inhibitor against the log concentration of inhibitor. The X-intercept of the linear transformation is equal to the inverse log of the KI.

Stable Expression in RH7777 Cells:

Rat hepatoma RH7777 cell monolayers were transfected with the mLPA1 plasmid DNA using the calcium phosphate precipitate method and clonal populations expressing the neomycin phosphotransferase gene were selected by addition of geneticin (G418) to the culture media. The RH7777 cells were grown in monolayers at 37° C. in a 5% CO02/95% air atmosphere in growth media consisting of: 90% MEM, 10% fetal bovine serum, 2 mM glutamine and 1 mM sodium pyruvate.

Cardiovascular Measurements:

All procedures were performed on Male Wistar rats in accordance with National Institutes of Health and University of Virginia animal care and usage guidelines. Anesthesia was induced by 5% halothane (in 100% $O_2$). Rats were intubated and artificially ventilated with 1.5-1.8% halothane in 100% $O_2$ for surgical procedures. A femoral artery was cannulated to record mean arterial pressure (MAP) and heart rate (HR), and a femoral vein was cannulated to administer anesthetic agents. A femoral vein was cannulated for administration of lipids. The left splanchnic nerve was isolated via a retroperitoneal approach, and the segment distal to the suprarenal ganglion was placed on two Teflon-coated silver wires that had been bared at the tip (250 mm bare diameter; A-M Systems, Everett, Wash.). The nerve and wires were embedded in a dental impression material (polyvinysiloxane; Darby Dental Supply, Westbury, N.Y.), and the wound was closed around the exiting recording wires. On completion of surgery, the halothane anesthesia was terminated and was replaced by a α-chloralose (30 mg/kg solution in 3% sodium borate; 70 mg/kg initial bolus followed by hourly supplements of 20 mg/kg iv; Fisher Scientific, Pittsburgh, Pa.). Rats were allowed to stabilize for 45 min before tests began. End-tidal CO2 was monitored by infrared spectroscopy and was maintained between 3.5 and 4.0%. Body temperature (measured rectally) was maintained at 37° C.

All physiological variables were monitored on a chart recorder (model RS 3600, Gould, Valley View, Ohio) and simultaneously stored on a videocassette recorder via a digitizer interface (model 3000A, frequency range: DC-22 kHz; Vetter Digital, Rebersburg, Va.) for off-line computer analysis. Data was analyzed with Spike 2 (Cambridge Electronics). The MAP was calculated from the pulse pressure measured by a transducer (Statham P10 EZ, Gould) connected to the brachial arterial catheter. The HR was determined by triggering from the pulse pressure (Biotach, Gould). Splancnic nerve activity (SNA) was filtered (10 Hz-3 kHz band pass with a 60-Hz notch filter), full-wave rectified, and averaged in 1-s bins. The femoral venous catheter (dead space 100 mL) was loaded with each lipid and was flushed with 200 mL of saline to expel the drug.

Materials: Chemicals for syntheses were purchased from Aldrich Chemical Company, Inc., Sigma Chemical Company, Inc., Advanced ChemTech Chemical Company, Inc. and/or NovaBiochem Chemical Company, Inc., and were used without further purification. GTP[γ 35 S] was purchased from Amerhsam, Fura-3 and Fura-4 AM were purchased from Molecular Probes Inc., A431 and RH7777 cells were purchased from the American Type Culture Collection (Manassas, Va.) and tissue culture media and serum was from GibcoBRL/Life Technologies (Gaithersburg, Md.). HEK293T cells were a gift from Dr. Judy White's laboratory (Dept. Cell Biology, University of Virginia) while G protein β and γ DNAs were a gift from Dr. Doug Bayliss (Dept. Pharmacology, University of Virginia). LPAs (1-oleoyl and 1-palmitoyl) and dioctyl glyceryl pyrophosphate were purchased from Avanti Polar Lipids (Alabaster, Ala.).

Results:

Using N-oleoyl ethanolamide phosphoric acid (NAEPA) as a lead structure, a series of 2-substituted LPA analogs was synthesized. The details of the synthesis and analysis of the full set of compounds in this series is described in Example 2. Each compound was characterized by $^1$H NMR, $^{13}$C NMR, and mass spectrometry.

The differential coupling of LPA1 versus LPA2 and LPA3, the lack of a reliable radioligand binding assay, and the near ubiquity of endogenous LPA responses prohibited the use of most common receptor assay techniques (i.e. measurements of adenylyl cyclase activity, calcium mobilization, radioligand binding) to assess each compound's activity. Therefore, we adapted a GTP[γ 35 S] binding assay to measure the relative efficacies and potencies of each compound compared to LPA. This assay isolates each recombinant LPA receptor and allows analysis of all three receptors using the same system. Note that membranes from HEK293T cells transfected with only G protein DNAs (i.e., no receptor DNA) were devoid of LPA-stimulated GTP binding despite expressing endogenous LPA receptors.

Many NAEPA compounds with various 2-substituents were synthesized and examined. Since the 2 position is a prochiral site, both enantiomers of the eight compounds were synthesized. Three patterns were revealed when the agonist compounds were tested in this series at the three LPA receptors in the broken cell assay. First, each LPA receptor showed a marked (one log order or more) selectivity for one enantiomer. Second, those compounds with substitutions at the R2 position of Formula I were invariably the more potent agonists. Third, agonist potency decreases as the bulk of the substituent increases. The 2-substituted NAEPA compounds containing either hydrophilic (methylene hydroxy, carbomethyl, methylene amino) or hydrophobic moieties (methyl, ethyl, isopropyl, benzyl) exhibited agonist activity in the GTP[γ 35 S] binding assay (see Table 1). The smaller groups conferred greater potency, with the methyl (VPC12086), methylene hydroxy (VPC31143) and methylene amino (VPC12178) compounds being more potent than 1-oleoyl LPA at LPA1 (Table 1). Also, as the 2-substituent becomes bulkier, the efficacy was noticeably reduced at this receptor. In contrast, bulkier hydrophobic side chains, although less potent, were fully efficacious at the LPA2 receptor (Table 1).

TABLE 1

Agonist activities of 2-substituted N-oleoyl EPA compounds

| Lipid | Functional Group | A1 LP EC50 (nM) | Emax | A2 LP EC50 (nM) | Emax | A3 LP EC50 (nM) | Emax |
|---|---|---|---|---|---|---|---|
| LPA |  | 11.7 | 100 | 6.8 | 100 | 262.5 | 100 |
| 31143 | Methylene Hydroxy | 7.9 | 161.4 | 116.5 | 104.6 | 321.8 | 106.6 |
| 31144 | Methylene Hydroxy | >5000 | 91.1 | 2645 | 77.3 | 4349 | N/A |
| 31139 | Carbo Methyl | 18.5 | 66.2 | 29.2 | 91.3 | 1484 | 84.4 |
| 31180 | Carbo Methyl | 1215 | 50.6 | 3461 | 60.2 | >5000 | 3.8 |
| 12178 | Methylene Amino | 4.9 | 98.7 | 50.3 | 103.2 | 683.7 | 102.9 |
| 12048 | Methylene Amino | >5000 | 9.4 | >5000 | 36.4 | >5000 | 3.8 |
| 12086 | Methyl | 3.4 | 107.6 | 18.3 | 95.2 | 112.6 | 93.4 |
| 12101 | " | 2900 | 48.1 | >5000 | 6.9 | >5000 | 9.7 |
| 12109 | Ethyl | 35.8 | 66.8 | 161.9 | 92.6 | 1083 | 83.5 |
| 12115 | " | 1580 | 62.3 | 4280 | 85.6 | 4980 | 89.3 |
| 12098 | Isopropyl | 73.8 | 51 | 799.3 | 85.8 | 3815 | 45.3 |
| 40105 | " | >5000 | 14.8 | >5000 | 27.6 | >5000 | 27.7 |
| 12084 | Benzyl | 38.4 | 23.7 | 268.3 | 97 | 351.4 | 78.7 |
| 12255 | " | >5000 | N/A | >5000 | N/A | >5000 | N/A |

As was observed with the LPA1 receptor, the small methyl and methylene amino groups conferred the highest potency at the LPA2 receptor but none of these compounds proved more potent than 1-oleoyl LPA at this site. The LPA3 receptor exhibited much the same profile as the LPA2 receptor as far as efficacies and potencies of compounds relative to LPA are concerned. However, the LPA3 receptor characteristically exhibited higher (1-2 log order) EC50 values for all compounds, including LPA. Presumably, the LPA3 receptor has an intrinsically lower affinity for LPA and LPA analogs. Like the hydrophilic compounds, each LPA receptor showed strong stereoselectivity for a hydrophobic substituent in the R2 position of Formula I.

Although saturated ligands were repeatedly found that are active at LPA3, mono-unsaturated compounds were also consistently found that are more potent at this receptor. For example, preliminary results with an 18:1 (oleoyl) analog of SDB-213 suggest that the mono-unsaturated compound is significantly more potent (equipotent to LPA) than the saturated compound at LPA3 in this assay. LPA1 and LPA2 do not exhibit this selectivity for mono-unsaturated vs. saturated acyl groups.

To investigate an LPA response in a physiologic context, mean arterial blood pressure (MAP), heart rate, and postganglionic sympathetic tone was monitored in anesthetized adult rats as a function of LPA or LPA analog administration. LPA had been shown previously to increase blood pressure transiently in this model. Intravenous injection of three enantiomeric pairs of compounds resulted in a transient increase in MAP with the same pattern of stereoselectivity as observed with the in vitro assays. Concomitant with this rise in MAP was a decrease in heart rate and sympathetic output indicative of baroreceptor reflex response.

The compounds that were only slightly efficacious at LPA1, e.g. the benzyl-containing VPC12084, were assayed for their ability to antagonize LPA induced GTP[γ 35 S] binding. Although this compound did block LPA activity in the GTP[γ 35 S] binding assay, the benzyl compound (VPC12084) was revealed to posses appreciable agonist activity in assays with greater levels of amplification (e.g., whole cell assays of calcium mobilization or inhibition of cAMP accumulation). In the course of exploring variations of the benzyl substituent, a benzyl-4-oxybenzyl substituent in the same relative configuration (R2: VPC12204) was found to have a reduced, but still measurable, agonist activity in whole cell assays. However, its enantiomer [i.e., VPC12249, the compound with the benzyl-4-oxybenzyl substituent in the S (the R3 substituent of Formula I) configuration] was completely devoid of agonist activity in the whole cell assays and in the GTP[γ 35 S] binding assay. concentration, this compound is a surmountable antagonist at the LPA1 and LPA3, but not the LPA2, receptors (FIG. 6). The KI values for VPC12249 determined by Schild regression are 137 and 428 nM at the LPA1 and LPA3 receptors, respectively, in this assay. The same activity was determined with human LPA1 using a recombinant baculovirus-infected insect Sf9 cell membrane preparation.

The antagonist activity measured in the broken cell assays was confirmed in whole cell experiments wherein LPA-induced rises in free intracellular calcium in HEK293T cells were blocked. This cell type expresses the LPA1 and LPA3, but not LPA2 receptor genes, as determined by RT-PCR. Increasing concentrations of VPC12249 resulted in parallel, rightward shifts in the LPA concentration response curves (KI 132 nM). The extent of rightward shift observed in the same experimental protocol with A431 cells, which express the LPA2 as well as the LPA1 and LPA3 genes RT-PCR not shown), was much smaller (KI 1970 nM) as predicted from the lack of antagonist activity of VPC12249 at the calcium-mobilizing LPA2 receptor in the GTP binding assay. The blocking action of VPC12249 was not a general post-receptor event as shown by the lack of antagonism of ATP-evoked calcium transients. Inhibition of forskolin-induced increases in cAMP levels in RH7777 cells stably expressing LPA1 was also inhibited by VPC12249.

EXAMPLE 3

Synthesis of rac-N-oleoyl-1-hydroxy-propylamide phosphonic acid (NOHPP)

Two batches of NOHPP have been synthesized as a racemic mixture. After observing LPA mimetic activity with the first batch (named JAR1842), the material was re-synthesized, and this batch was named VPC12031. Both batches showed the same profile on thin layer chromatography (TLC) ($R_f$ 0.31, chloroform/acetone/methanol/glacial acetic acid/water, 50/15/13/12/4) whereon they migrated as a single, discrete spot. Further, the NMR spectrum of VPC12031 was as expected and the formula weight measured by mass spectrometry (419.5 daltons) agrees with that of the structure. Thus confirming the identity and high degree of purity of the NOHPP sample.

To assay NOHPP and other compounds at individual LPA receptors, the adapted GTPγS binding assay of Example 3 was used. Briefly, individual, recombinant LPA receptors were express along with heterotrimeric G proteins in HEK293T cells. For the LPA receptor LPA1, which naturally couples to Gi/o proteins, membranes from rat hepatoma cells (RH7777) were also used that have been transfected only with LPA1 DNA. Membranes prepared from these cells are used to measure GTPγ[$^{35}$S] binding as a function of test compound concentration. The resulting dose-response curves provide relative potency ($EC_{50}$) and efficacy ($E_{max}$) for the test compounds. The assay is robust and free of background from the LPA receptors endogenous to HEK293T cells. In FIGS. 2A-C we show the relative activities of LPA and NOHPP at the three known (i.e. cloned) LPA receptors (LPA1, LPA2 and LPA3). NOHPP is distinctly less potent and far less efficacious than LPA at LPA3, but as efficacious as, but somewhat less potent than, LPA at LPA1 and LPA2.

NOHPP was also tested for activity at the three cloned LPPs. Although the phosphonate head group eliminates the possibility of NOHPP acting as a substrate, it is possible that the compound could be a competitive inhibitor. For the initial assay, 0.1, 1.0 and 10.0 mM NOHPP was tested in competition with 50 nM [$^{32}$P]LPA and assayed for the appearance of water soluble radionuclide. As can be seen in FIG. 3, NOHPP inhibited LPP3 and, to a lesser extent, LPP1. NOHPP was inactive in this assay at LPP2.

The activity of the alpha keto NOHPP analog (VPC12060) at the three LPPs has also been tested. The structure of the alpha keto NOHPP analog is as follows:

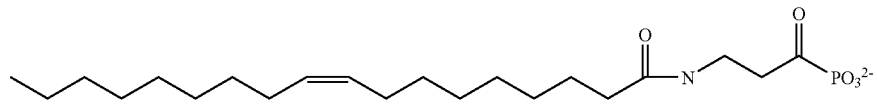

FIG. 4 presents data concerning the inhibition of the three phosphatases (PAP2a, PAP2b and PAP2c (aka LPP1, LPP3, LPP2, respectively) by the alpha hydroxy phosphonate analog of LPA(VPC12031) and the alpha keto phosphonate analog of LPA (wls060). Both compounds are markedly better at the PAP2b (LPP3) than PAP2a (LPP1) which in turn is better than PAP2c (LPP2). Based on the results of the activity of NOHPP, it is anticipated that analogs of NOHPP will also be active.

EXAMPLE 4

Synthesis of NOHPP
[(9Z)-N-(3-hydroxypropyl)octadec-9-enamide]

To a solution of 1-aminopropanol (4.04 ml, 52.8 mmol) and pyridine (4.27 ml, 52.8 mmol) in methylene chloride was slowly added oleoyl chloride (5 ml, 15.1 mmol). After 2 hours, the mixture was diluted with chloroform and washed with ammonium chloride (3×), brine (3×) and dried over sodium sulfate. Column chromatography (15% acetone/chloroform to 50% acetone/chloroform) provided the product as white solid.

(9Z)-N-(3-oxopropyl)octadec-9-enamide (22)

To a suspension of pyridinium chlorochromate (0.477 g, 2.21 mmol) and sodium acetate (36 mg, 0.44 mmol) in 10 ml of dichloromethane was cannulated as solution of 1 in 8 ml of dichloromethane. The mixture was stirred for 10 hours, quenched with ether, then filtered through celite and concentrated to an oil. Chromatography in 15% acetone/chloroform provided the product in 47% yield (0.495 g).

(9Z)-N-{3-[bis(tert-butoxy)carbonyl]-3-hydroxypropyl}octadec-9-enamide (23)

To a suspension of sodium hydride in 8 ml of THF at 0° C. was cannula as a solution aldehyde 3 in 6 ml THF. The mixture was allowed equilibrate to room temperature over an hour. The reaction was quenched with water and acidified with 10% HCl followed by extraction with chloroform (3×). The combined organic extracts were washed with brine (3×) and dried over sodium sulfate. Chromatography in 15% acetone/chloroform provided the product as off-white solid (130 mg, 36%).

(9Z)-N-(rac-3-hydroxy-3-phosphonopropyl)octadec-9-enamide (24)

To a solution of 23 in 1 ml of dichloromethane was added 0.3 ml trifluoroacetic acid. The mixture was stirred for 4 hours (monitored by TLC). Concentration and repeated washings with ether provided the product in 100% yield.

EXAMPLE 5

Synthesis of wls-b8L

3-(diethoxycarbonyl)propanenitrile

In a 50 ml of dry ethanol was added sodium (1.38 g, 60 mmol). After complete dissolution of sodium, diethyl phosphite (7.75 ml, 60 mmol) dissolved in 20 ml toluene was added slowly. After stirring for 1 hour at room temperature, acrylonitrile (3.95 ml, 57 mmol) dissolved in 20 ml toluene was added dropwise over 1 hour. The mixture was allowed to stir overnight. Dilution with water, extraction with $CH_2Cl_2$ (3×) and drying with sodium sulfate provided a crude yellow oil, which was concentrated and distilled under vacuum (134° C., 1.5 mmHg) to provide the product as clear liquid (6.11 g, 53%).

(3-aminopropyl)diethoxyphosphino-1-one

To a suspension of 3-(diethoxycarbonyl)propanenitrile (2.78 g, 14.5 mmol) and cobalt(ll) chloride (0.378 g, 2.91 mmol) in methanol at −30° C. was added sodium borohydride (5.49 g, 145 mmol) in small portions. The mixture was allowed to equilibrate to room temperature and stirred overnight. Concentrated HCl was added until the black mixture turned blue, which was extracted twice with dichloromethane. The pH of the aqueous phase was adjusted to 9 by addition of concentrated ammonium hydroxide, and the solution was evaporated to dryness to generate pink/blue solid. Concentrated ammonium hydroxide (100 ml) and dichloromethane (200 ml) was added and stirring was continued for 1 hour. Extraction with $CH_2Cl_2$ (2×), filtration, drying over sodium sulfate, and concentration provided the product as yellow liquid (2.0 g, 70%).

(9Z)-N-[3-(diethoxycarbonyl)propyl]octadec-9-enamide

To a solution of (3-aminopropyl)diethoxyphosphino-1-one (0.736 g, 3.77 mmol) and pyridine (0.61 ml, 7.54 mmol) at 0° C. was slowly added oleoylchloride (1.25 ml, 3.77 mmol) over 20 minutes. The reaction mixture was allowed to warm to room temperature, followed by stirring for another 2 hours. Dilution with ethyl acetate and extraction with saturated aqueous ammonium chloride (3×) and brine (3×), drying over sodium sulfate, and flash chromatography using 15% acetone/chloroform provided the product as off-white solid (0.572 g, 33%).

(9Z)-N-(3-phosphonopropyl)octadec-9-enamide

To a solution of (9Z)-N-[3-(diethoxycarbonyl)propyl]octadec-9-enamide (0.219 g, 0.48 mmol) in acetonitrile was added trimethylsilylbromide (0.189 ml, 1.43 mmol). The reaction mixture was refluxed for 2 hours and the solvent was evaporated under reduced pressure. Addition of ether and removal in vacuo, a process repeated several times, provided the product as brown solid (0.192 g, 100%).

EXAMPLE 6

Analysis of wls-b8L Activity:

To assay wls-b8L at individual LPA receptors, the GTPγS binding assay described in Example 2 was utilized. Briefly, individual recombinant LPA receptors were expressed along with heterotrimeric G proteins in HEK293T cells. Membranes prepared from these cells are used to measure GTPγ ($^{35}$S] binding as a function of test compound concentration. The resulting dose-response curves provide relative potency ($EC_{50}$) and efficacy ($E_{max}$) for the test compounds. wls-b8L was found to be more potent and efficacious at LPA1 than at either LPA2 or LPA3. Also evident is the lack of receptor-type selectivity by the other phosphonate compounds.

wls-b8L and the other phosphonates were also tested also for activity in three whole cell assays. For the LPA receptor LPA1, which naturally couples to Gi/o proteins, rat hepatoma cells (RH7777) were used that have been transfected only with mouse LPA1 DNA. In these cell cultures, drug dependent inhibition of cAMP accumulation was measured. wls-b8L, was determined to be fully efficacious in this assay at a concentration of 1 μM. At this concentration wls-b8L is inactive at mobilizing calcium through endogenous receptors LPA receptors expressed by MDA MB-231 cells. Finally, the activity of wls-b8L in activating a chloride conductance in *Xenopus laevis* ooctyes was measured. These cells are normally activated by LPA through an endogenous receptor. However, wls-b8L does not evoke this response. However, when injected with human LPA3 or LPA2 mRNAs a very modest response to wls-b8L is detected, but only when a concentration of 10 μM is applied to the oocyte surface.

EXAMPLE 7

Analysis of VPC12249 Effects in a Renal Ischemia-reperfusion Model

To examine the effect of the compound VPC12249 on renal injury following ischemia-reperfusion (IR) the following experiment was conducted. C57BL6 mice (20 gm, 8 wks of age) were used for all studies. The surgical protocol of renal IR has been previously described (Okusa et al., 1999. Am J. Physiol. (Renal Physiol.) 277: F404-412; Okusa, et al., 2000 Am. J. Physiol. (Renal Physiol.) 279; F809-F818, and Okusa et al., 2001 Kidney Int. 59:2114-2125). For the injury protocol, bilateral flank incisions were made under anesthesia with a regimen that consists of ketamine (100 mg/kg, ip.), xylazine (10 mg/kg, ip.) and acepromazine (1 mg/kg, im.). Renal pedicles were exposed and cross-clamped for 27-32 min. Kidneys were examined for immediate reperfusion following clamp removal. Wounds were closed and mice were returned to cages. Mice were injected with VPC12249 (0.01, 0.1 and 1.0 mg/kg/2 hrs) or vehicle. The mice were sacrificed and the kidneys harvested at 1, 4, 8, 24, 48 hrs, 5 and 7 days. Treatment with VPC12249 or vehicle was initiated 2 hrs prior to ischemia, at the time of reperfusion and every 2 hrs for 4 additional doses. Mice were sacrificed following 24 hrs of reperfusion and plasma was obtained for BUN and creatinine. Plasma creatinine was 1.49±0.26 (n=1), 1.06±0.25 (n=4), 0.45±±0.13 (n=4) and 0.31±0.4 (n=4), for vehicle, VPC12249 0.01, 0.1 and 1.0 mg/kg/2 hrs, respectively.

VPC12249 administered at 0.1 (P<0.05) and 1.0 mg/kg/2 hrs (P<0.1) were significantly different compared to vehicle. H and E sections revealed a marked degree of tissue preservation following VPC12249 at 1 mg/kg/2 hr.

EXAMPLE 8

Synthetic Schemes for Preparing Phospho-esters Deriviatives

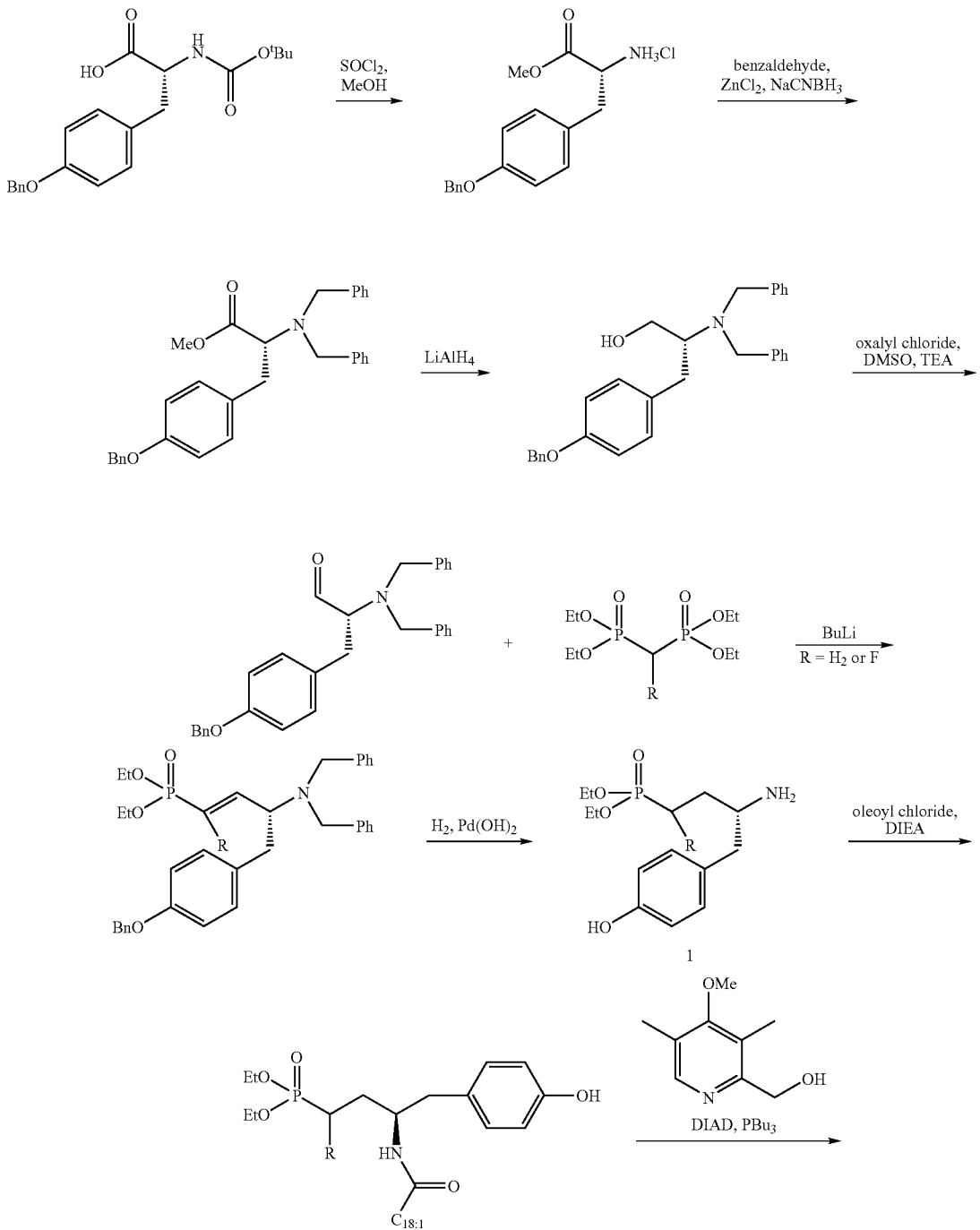

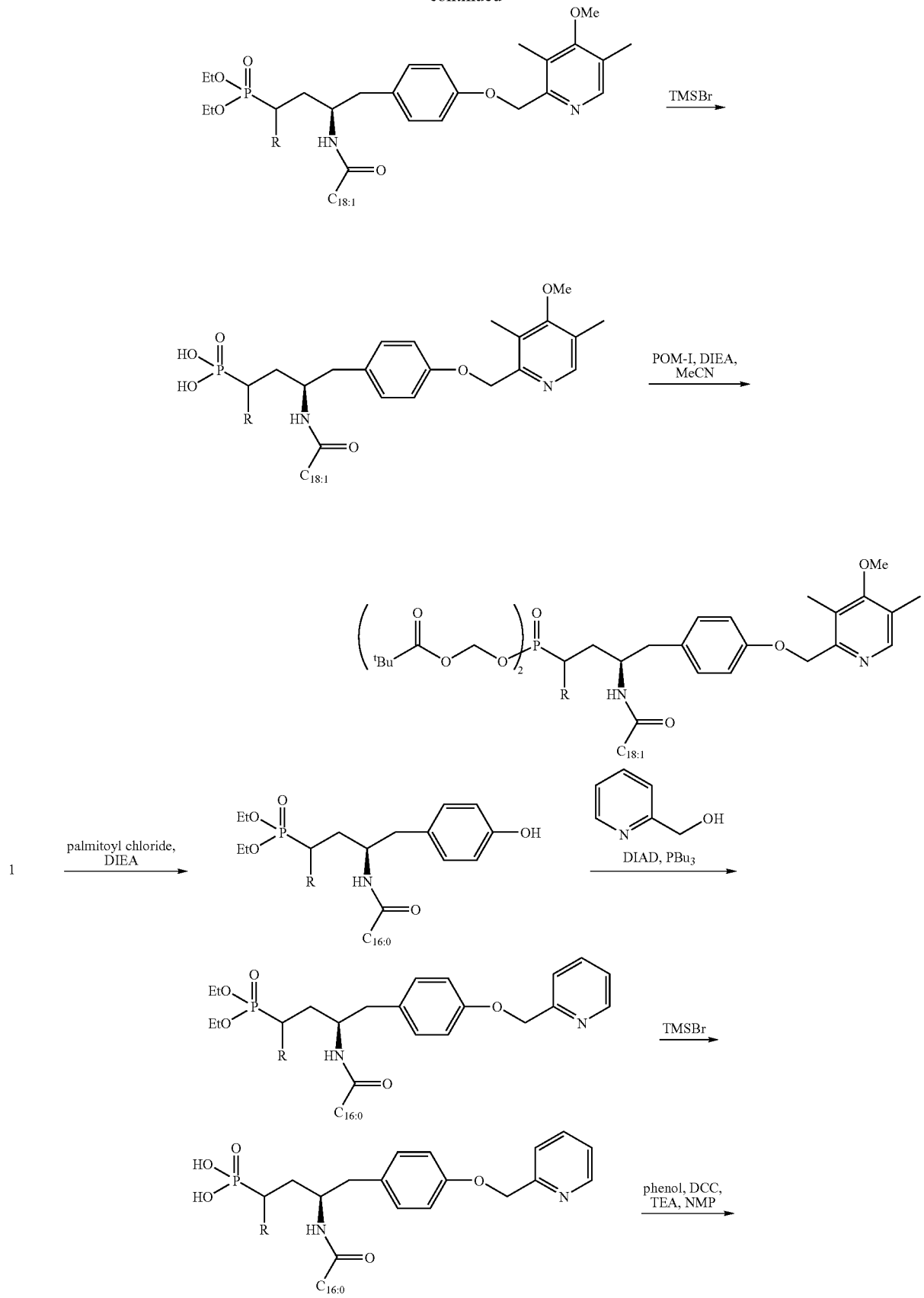

-continued

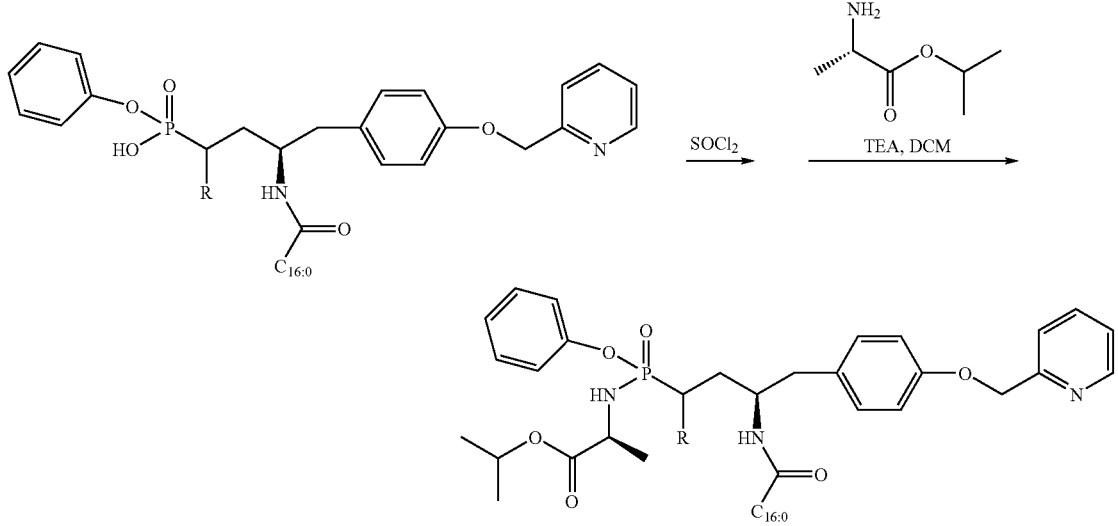

EXAMPLE 9

NAEPA Derivatives Containing a Benzyl-4-Oxybenzyl Substituent

A series of 2-substituted N-acyl ethanolamine phosphoric acid (NAEPA) derivatives were synthesized and evaluated at LPA receptors. From this series of NAEPA derivatives emerged a dual LPA1/LPA3 antagonist containing a bulky benzyl-4-oxybenzyl substitution at the 2-position in the linker region:

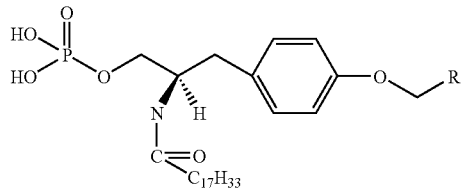

VPC12249
R = phenyl
26a = 2-Pyridyl (26)

Scheme 9. Synthesis of compounds 29a-e.

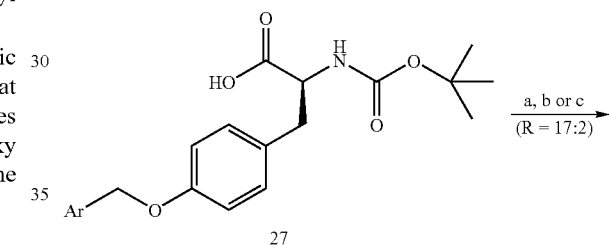

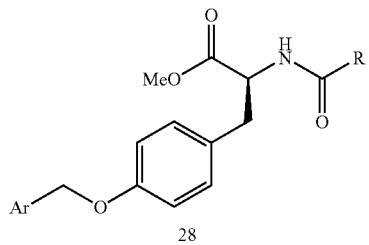

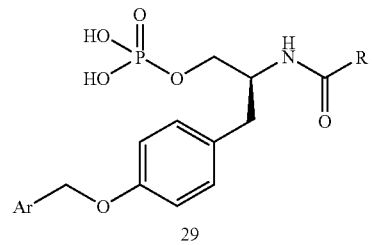

To more thoroughly elucidate the structural parameters that contribute to potency and selectivity in LPA antagonism, a series of VPC12249 (26) analogues were prepared and analyzed. Syntheses of all the compounds listed in Tables 2-4 are described in Schemes 9-11. As outlined in Scheme 9, N-acyl tyrosine methyl esters 28a-c,e were prepared by esterification and subsequent N-acylation of protected tyrosine 27. Methyl ester reduction and phosphinylation of the resulting alcohol followed by in situ oxidation and subsequent trifluoroacetic acid (TFA) deprotection afforded phosphates 29a-c,e. In the case of 29d, catalytic hydrogenolysis of 28c afforded the phenol, which was O-alkylated to the 3-methoxybenzyl aryl ether using Mitsunobu conditions.

Reagents and conditions: (a) $SOCl_2$, MeOH, 18 h, 100%; (b) acyl halide, DIEA, $CH_2Cl_2$, 4 h, 74-85%; (c) linoleic acid, PyBOP, DIEA, 18 h, 70%; (d) $NaBH_4$, $CaCl_2$, EtOH—THF (2:1), 18 h, 95%; (e) di-tert-butyldiisopropyl phosphoramidite, tetrazole, 4 h; then 30% $H_2O_2$, 4 h, 75-80%; (f) TFA—$CH_2Cl_2$ (1:2), 1 h, 95-100%.

Scheme 10. Synthesis of compounds 35a-u.
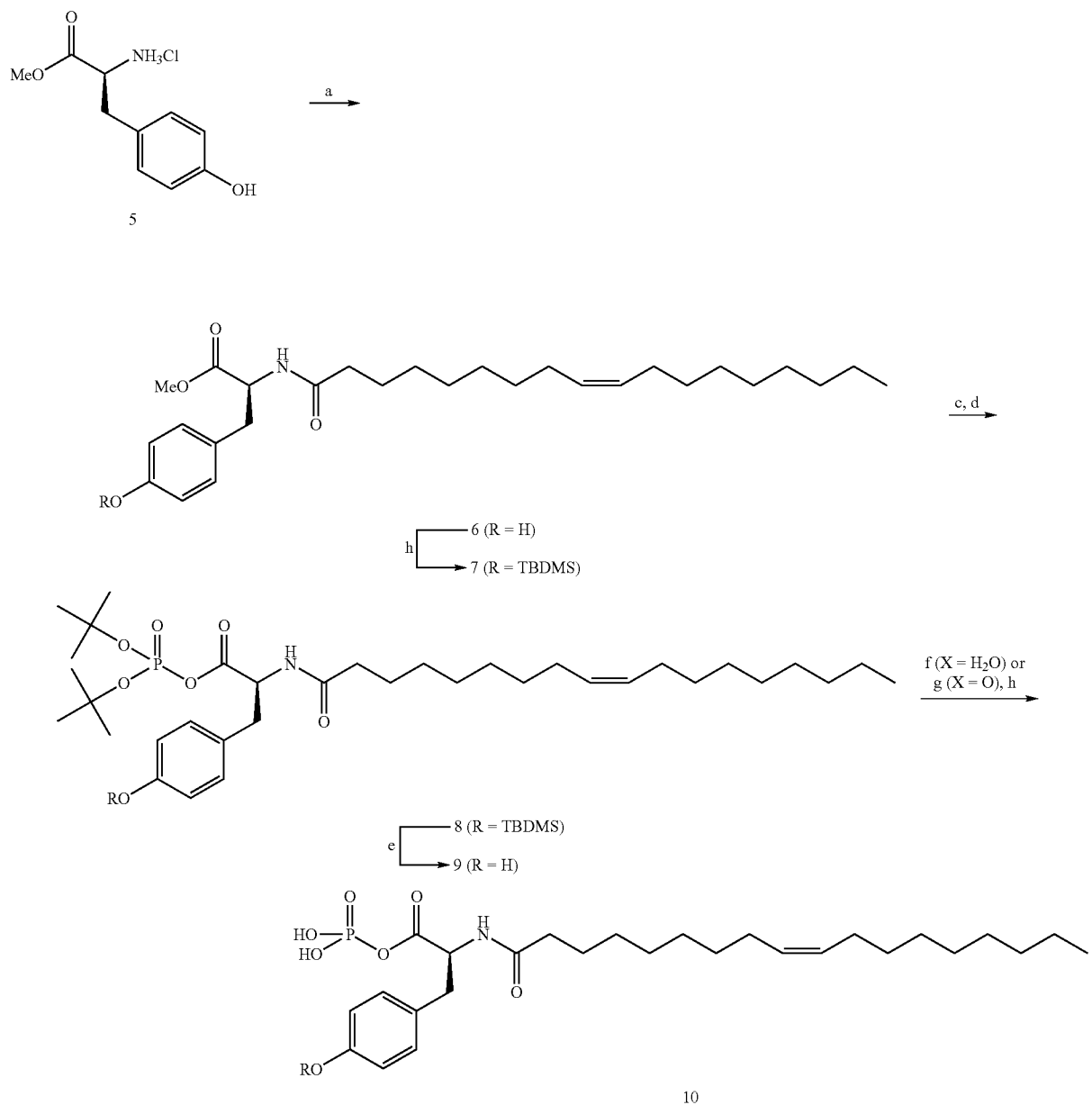
Reagents and conditions: (a) oleoyl chloride, DIEA, CH$_2$Cl$_2$, 4 h, 85%; (b) TBDMSCl, DIEA, DMF, 4 h, 96%; (c) NaBH$_4$, CaCl$_2$, EtOH—THF (2:1), 18 h, 95%; (d) di-tert-butyldiisopropyl phosphoramidite, tetrazole, 4 h; then 30% H$_2$O$_2$, 4 h, 83%; (e) TBAF·3H$_2$O, THF, 1 h, 95%; (f) ROH, PPh$_3$, DIAD, CH$_2$Cl$_2$, 18 h, 73-88%; (g) RCOOH, DIEA, PyBOP, 18 h, 50-70%; (h) TFA—CH$_2$Cl$_2$ (1:2), 1 h, 95-100%.
Scheme 11. Synthesis of compounds 39a-b.
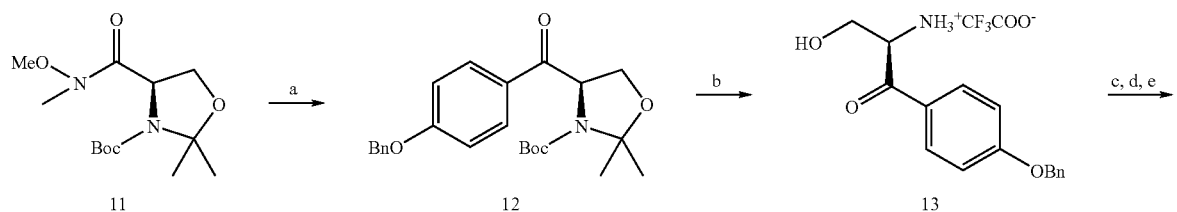

-continued

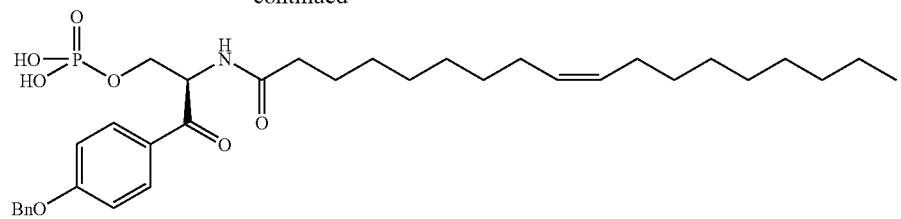

14

Reagents and conditions: (a) 4-benzyloxyphenyl iodide, Mg⁰, Et₂O, 25° C.; (b) TFA—CH₂Cl₂ (1:2), 1 h, then Et₂O precipitation, 26% over two steps; (c) oleoyl chloride, DIEA, CH₂Cl₂, 4 h, 77%; (d) di-tert-butyldiisopropyl phosphoramidite, tetrazole, 4 h, 30% H₂O₂, 4 h, 75%; (e) TFA—CH₂Cl₂ (1:2), 1 h, 100%.

As outlined in Scheme 10, the amide 32 was obtained by selective acylation of tyrosine methyl ester followed by protection of the phenol as the silyl ether. Methyl ester reduction and phosphorylation followed by desilylation with tetrabutylammonium fluoride (TBAF) afforded the phosphotriester 34. Compound 34 was a common intermediate used to generate a series of ethers/esters by the Mitsunobu reaction or standard PyBOP chemistry, respectively. TFA deprotection afforded phosphates 35a-u. In the case of glucuronide 35u, catalytic hydrogenolysis using Pearlmann's catalyst deprotected the tetra-O-benzyl-D-glucopyranose moiety prior to TFA deprotection of the phosphate ester. Compound 35u is therefore the only compound in this series, which contains a saturated acyl chain.

TABLE 4

Comparison of ketone derivatives 14a-b with tyrosine-based lead compound 1

| Compounds | S/R | LPA$_1$ IC$_{50}$ (nM) | LPA$_1$ K$_i$ (nM) | LPA$_3$ IC$_{50}$ (nM) |
|---|---|---|---|---|
| 26 | S | 5210 | 137 | 6450 |
| 39a | S | >10,000 | N/D | >10,000 |
| 39b | R | 2490 | N/D | >10,000 |

The synthesis of ketone derivatives 39a-b is outlined in Scheme 11. Serine was converted in three steps into Weinreb's hydroxamate 36, whose condensation with the Grignard reagent 4-benzyloxyphenyl magnesium iodide proceeded to give the expected ketone 37 in modest yield. TFA deprotection afforded the ammonium salt 38, which underwent selective acylation followed by phosphorylation. TFA deprotection provided ketones 39a-b.

All compounds were characterized by $^1$H and $^{13}$C NMR, mass spectroscopy and, in certain cases, elemental analysis. A GTP[γ35S] binding assay was adapted to assess in vitro activity. The compounds presented in Tables 2-4 were assayed for their ability to antagonize LPA-evoked GTP[c35S] binding. However, the differential affinity of LPA1 versus LPA3 for 1-oleoyl-LPA prohibited a uniform analysis at each receptor. Specifically, the relatively low affinity of the LPA3 receptor for 1-oleoyl-LPA impeded the determination of accurate Ki values for each antagonist. The detergent-like properties of the ligands prohibit the use of concentrations greater than 30 IM, which are required to achieve a statistically significant rightward shift in the sigmoidal curve requisite to the Ki determination. Consequently, the relative potencies, in the form of IC$_{50}$ values, are shown for the LPA3 receptor in Tables 2-4. The Ki values as determined by Schild regression are shown for the LPA1 receptor. That is, compounds that produced rightward, parallel shifts in the concentration-response curves as a function of antagonist concentration were considered surmountable antagonists for which a reliable Ki value could be calculated for the LPA1 receptor. LPA1 IC$_{50}$ values are also listed for comparison with LPA3 data. The compounds presented here were devoid of any significant activity at the LPA2 receptor.

Optimization of the N-acyl moiety (Table 2), the outermost benzyl substituent and stereochemistry of 1 (Table 3) led to the development of an SAR as described below. In addition, two ketone derivatives of 1 (Table 4) were evaluated.

Phospholipid chain length plays a role in LPA receptor antagonist binding (Table 2). N-Oleoyl lead compound 26 displays potent LPA1/LPA3 dual antagonism. At LPA1, active compounds generally contained relatively long chain length and unsaturation (26 and 29e) in the N-acyl region. Palmitoyl derivatives 29c-d showed no activity at LPA1 while the unsaturated derivative 29e displayed potency comparable to lead compound 26. At LPA3, palmitoyl derivatives 29c-d were comparable in activity to 26 while shorter chain lengths and increased unsaturation led to a marked reduction in inhibitory activity. Thus compound 29e, which contains a linoleoylamide shows selectivity for LPA1 while palmitoyl derivatives 29c-d were active only at LPA3.

As described in Table 3, the outermost benzyl substituent of LPA antagonists can be modified with various ether/ester linkages to improve the potency and selectivity of lead compound 26. LPA receptors also clearly exhibit stereochemical recognition as has been previously reported. The N-oleoyl lipid chain is held constant among derivatives 35a-u as this feature has been shown to afford dual LPA1/LPA3 antagonism and good potency (Table 2). When the benzyl moiety of 26 is replaced with small alkyl substituents as in compounds 35a, inhibitory activity is generally diminished. Relatively bulkier alkyl ethers 35f-i, display varying degrees of antagonism at LPA3 but are inactive at LPA1. Electron-rich aromatic systems in place of the outermost benzyl moiety confer activity to LPA antagonists. This is exemplified by derivatives 35j-m, which show good to excellent potency, particularly at LPA3. Sterically demanding electron-rich aromatic substituents, in general, retain the potency of 1 at LPA3 but exhibit diminished activity at LPA1. This trend is particularly evident in compounds 35m and 35r. However, 4-npentylbenzoyl derivative 35o was inactive at both receptors, a result which implies some limitation to the steric tolerance of the LPA3 antagonist binding pocket. Polar groups such as 4-aminobenzoyl (35p) and glucuronide 35u were also devoid of activity. 2-pyridyl derivatives 35s-t were significantly more potent than lead compound 26 at LPA1 and LPA3 receptors. R enantiomer 35t improves on the antagonist activity of 26 by approximately one log order at each receptor (FIGS. 2 and 3). Indeed, all of the R derivatives in Table 3 are more potent than their S counterparts at LPA receptors.

Thus, in comparison to 26, electron-rich aromatic systems in place of the outermost benzyl moiety improve antagonist activity at both receptors (10 k). LPA3 is more tolerant of sterically bulky substituents, which provides a strategy to realize LPA3-selective antagonists with modest potency such as 10g and 10m. Finally, N-heterocycle derivative 35t is a high affinity dual antagonist, with a Ki value of 18 nM at the LPA1 receptor and $IC_{50}$ of 175 nM at LPA3.

Two ketone derivatives of 26, oxidized at the innermost benzylic carbon atom, were evaluated at LPA receptors (Table 4). In this series (39a-b), a stereochemical preference for the R enantiomer is apparent at the LPA1 receptor. Installation of the carbonyl in derivatives 39a-b completely diminishes activity at the LPA3 receptor while 39b retains potency comparable to 26 at LPA1. Thus, 39b represents an LPA1-selective blocker of modest potency.

EXAMPLE 9

2-Pyridyl Containing LPA Receptor Antagonists

The following series of high-affinity $LPA_1/LPA_3$ receptor antagonists, containing a 2-pyridyl moiety, were synthesized to investigate the structure-activity relationship (SAR) of LPA receptor antagonists. Synthesis of all the compounds listed in Tables 5 & 6 are described in Example 8 and in Scheme 13 below. The synthetic route to prepare the phenol 34 is described in detail in Example 8. In brief, a one-pot procedure accomplished selective acylation of tyrosine methyl ester followed by Osilylation to provide 32 in acceptable yield. The phenol 34 was efficiently generated in three steps from 32. This intermediate was O-alkylated by subjecting a series of benzylic alcohols to standard Mitsunobu conditions. To produce compounds 57a-l, compound 34 is first reacted with ROH, PBu$_3$, DIAD, CH$_2$Cl$_2$, 18 h, 73-88%; and then TfA:CH$_2$Cl$_2$ (1:2), 1 h, 80-90% after crystallization from MeOH/Et$_2$O. The benzylic alcohols were either prepared in a straightforward manner from commercially available methyl esters or carboxylic acids (57n-p) or the synthetic methods have been described elsewhere [(57e-f (Haudrechy et al., Tetrahedron 2000, 56,3181-3187), 57g-m (Kuhler et al., J. Med. Chem., 1995, 38, 4906-4916)]. In most cases, the aryl ether Mitsunobu products were inseparable from the by-product tri-n-butyl phosphine-oxide by standard silica gel flash chromatography. This mixture was therefore subjected to trifluoracetic acid (TFA) deprotection of the phosphotriester and the pure phosphoric acids were obtained by recrystallization from methanol/diethyl ether.

α-methylene phosphonates 63a-e were realized from the N,N-dibenzylamino aldehyde 58, which was easily prepared from tyrosine following the procedure reported by Reetz et al., J. Chem. Soc., Chem. Commun. 1982, 1270-1271. Next, treatment of tetraethyl methylenediphosphonate with n-butyllithium at −78° C. generated the lithiated carbanion which condensed with 58 to afford the vinylphosphonate 59 in good yield. Catalytic dual-hydrogenation/hydrogenolysis using Pearlmann's catalyst provided the amino-phenol 60 which was converted to the phosphonodiester 62 using the abovementioned procedures. Finally, transesterification of each ester 62 using bromotrimethylsilane (TMSBr) and subsequent desilylation with aqueous methanol provided the pure a-methylene phosphonates 63a-e after crystallization. The detailed synthesis of the diastereomeric α-hydroxy phosphonate 63f will be reported in a manuscript which is in preparation.

All compounds were characterized by $^1$H and $^{13}$C NMR, mass spectroscopy and, in most cases, C, H, N analyses. A membrane-based GTP[γ$^{35}$S] binding assay was adapted to assess in vitro activity at the $LPA_1$ and $LPA_3$ receptors. Antagonist potency data for 2-pyridyl aryl analogues of 26a (57a-p) are presented in Table 1. It is evident that the 2-pyridyl regioisomer in the R configuration exhibits superior dual antagonism (26a as compared with 57a-d). The net dipole moment of the aromatic system may play a role in LPA receptor antagonist binding as compounds 57e, g and i exhibit varying inhibitory potencies at each receptor. Alternatively, Lewis-basicity of the N-heterocycle moiety could potentially account for this phenomenon. Electron-rich compounds 57g-h, 26a are more potent at the $LPA_3$ receptor than the unsubstituted lead compound 26a (FIG. 2).

The aforementioned derivatives neither gain nor lose activity at $LPA_1$. The 4-methoxy-3,5-dimethylpyridine system of 57l-m has been reported to possess approximately one log order greater basicity than pyridine. Contrarily, methoxyquinoline derivative 57o is less potent than the unsubstituted 57n at the LPA$_3$ receptor and more potent at LPA$_1$. The quinoline series 57n-p exhibits a marked dual reduction in potency compared to 26a and therefore may be too sterically demanding for either antagonist binding pocket. Sterics, in the form of pyridyl ring substitutions, presumably acting in concert with correspondingly enhanced basicity, generally improve antagonist activity at the LPA$_3$ receptor (26a as compared with 57g-i, l). Compound 57g is particularly potent and LPA$_3$-selective. Notably, trifluoroethoxy derivative 57i is equipotent to 26a at the LPA$_1$ receptor and ~three-fold more potent at LPA$_3$. Indeed, this compound is the most potent LPA$_1$/LPA$_3$ dual antagonist reported to date. Thus, we have shown that by altering the sterics and electronics of the outermost aromatic system, highly potent and somewhat LPA$_3$-selective antagonists may be realized.

TABLE 5

Inhibitory evaluation of aryl ether derivatives 7a-n as compared with lead compound 1.

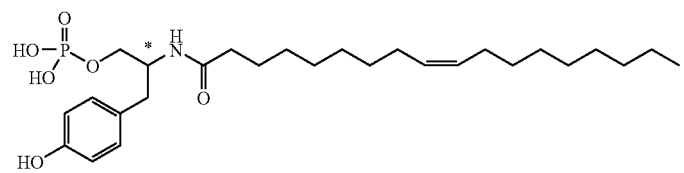

| Compds | R | S/R | LPA$_1$ IC$_{50}$, nM | LPA$_1$ K$_i$, nM | LPA$_3$ IC$_{50}$, nM |
|---|---|---|---|---|---|
| 1[11] 26a | 2-pyridylmethyl | R | 109 | 18 | 175 |
| 14[11] | 2-pyridylmethyl | S | 604 | 156 | 940 |
| 57a | 3-pyridylmethyl | R | 992 | N/D | 1688 |
| 57b | 3-pyridylmethyl | S | 4500 | N/D | 6236 |
| 57c | 4-pyridylmethyl | R | 735 | N/D | 2075 |
| 57d | 4-pyridylmethyl | S | >10000 | N/D | 6960 |
| 57e | 6-OMe-2-pyridylmethyl | R | 2840 | N/D | 455 |
| 57f | 6-OMe-2-pyridylmethyl | S | >10000 | N/D | 1093 |
| 57g | 4-OMe-2-pyridylmethyl | R | 6250 | N/D | 102 |
| 57h | 4-OEt-2-pyridylmethyl | R | 143 | 26 | 39 |

TABLE 5-continued

Inhibitory evaluation of aryl ether derivatives 7a-n as compared with lead compound 1.

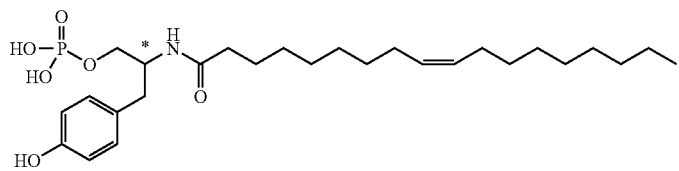

| Compds | R | S/R | LPA$_1$ IC$_{50}$, nM | LPA$_1$ K$_i$, nM | LPA$_3$ IC$_{50}$, nM |
|---|---|---|---|---|---|
| 57i | 2-ethyl-4-(OCH$_2$CF$_3$)pyridine | R | 84 | 19 | 48 |
| 57j | 2-ethyl-4-(O-propyl)pyridine | R | 141 | 64 | N/D |
| 57k | 2-ethyl-4-(OCH$_2$CH$_2$OMe)pyridine | R | 114 | 35 | N/D |
| 57l | 2-ethyl-3,5-dimethyl-4-OMe-pyridine | R | 62 | 28 | 39 |
| 57m | 2-ethyl-3,5-dimethyl-4-OMe-pyridine | S | 3690 | N/D | 561 |
| 57n | 2-ethylquinoline | R | 1430 | N/D | 533 |
| 57o | 2-ethyl-4-OMe-quinoline | R | 962 | N/D | 1156 |
| 57p | 2-ethyl-4-OMe-quinoline | S | >10000 | N/D | 2600 |

TABLE 6

Inhibitory evaluation of polar head group derivatives 13a-f as compared with lead compound 1

| Compds | X | Ar | R | S/R | LPA$_1$ IC$_{50}$, nM | LPA$_1$ K$_i$, nM | LPA$_3$ IC$_{50}$, nM |
|---|---|---|---|---|---|---|---|
| 26a | —O— | 2-CH$_2$-pyridyl | Oleoyl, 17:1[b] | R | 109 | 18 | 175 |
| 63a | —CH$_2$— | 2-CH$_2$-pyridyl | Oleoyl, 17:1[b] | R | >10000 | N/D | >10000 |
| 63b | —CH$_2$— | 2-CH$_2$-pyridyl | Oleoyl, 17:1[b] | S | >10000 | N/D | >10000 |
| 63c | —CH$_2$— | 2-CH$_2$-pyridyl | n-C$_{15}$H$_{31}$ | S | >10000 | N/D | 1050 |
| 63d | —CH$_2$— | 3-Me,4-OMe,5-Me,2-Et-pyridyl-CH$_2$ | Oleoyl, 17:1[b] | R | >10000 | N/D | 150 |
| 63e | —CH$_2$— | 3-Me,4-OMe,5-Me,2-Et-pyridyl-CH$_2$ | Oleoyl, 17:1[b] | S | >10000 | N/D | 4000 |
| 63f | —CH(OH)—[a] | benzyl | Oleoyl, 17:1[b] | S | 4230 | N/D | 232 |

[a] To the best of our knowledge, the additional stereocenter (a to P) is racemic. 13f is therefore evaluated as the unseparated mixture of diastereomers.
[b] 18 carbon chain; cis double bond between C-9 and C-10 from the carbonyl.

Antagonist potency data for phosphonate derivatives 63a-f are presented in Table 2. α-methylene phosphonate compounds 63a-e do not retain the inhibitory activity of their phosphate analogues at the LPA$_1$ receptor (Table 2). Hence, by applying this strategy for selectivity to compound 57l, a truly subtypeselective LPA$_3$ receptor antagonist was developed (63d). 63d shows improved potency over lead compound 26a at the LPA$_3$ receptor FIG. 3) and is the first non-hydrolyzable and presumably phosphataseresistant LPA antagonist reported to-date. 63d displays no antagonism at the LPA$_1$ receptor (FIG. 4). Only 63f, an α-hydroxy phosphonate derivative of an early lead antagonist, retained modest inhibitory activity at the LPA$_1$ receptor. The divergent properties of phosphonic acid antagonist head group analogues (63a-e) at LPA$_1$ may be due to a discrepancy between the second pK$_a$ value of unsubstituted phosphonic acids versus the relatively more acidic phosphoric acids. Hence, the substitution of an electronegative heteroatom onto the methylene group a to phosphorous (63f) increases acidity and regains LPA$_1$ antagonism. α-substituted phosphonates (i.e. substituted with CH(OH) or F) will therefore provide a useful platform for the realization of metabolically stable $LPA_1/LPA_3$ dual antagonists.

The invention claimed is:

1. A compound of the general structure

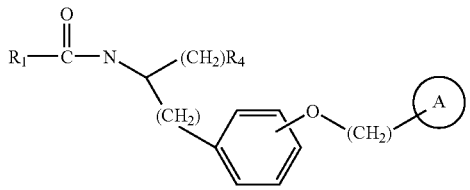

wherein $R_1$ is selected from the group consisting of $C_8$-$C_{22}$ alkyl, $C_8$-$C_{22}$ alkenyl, and —$(CH_2)_m$—Z—$R_{11}$;
wherein m is 0-20;
Z is selected from the group consisting of $C_4$-$C_8$ cycloalkyl, $C_5$-$C_8$ heterocyclic and $C_5$-$C_8$ aryl;
$R_{11}$ is selected from the group consisting of $C_1$-$C_{10}$ alkyl, $C_1$-$C_{20}$ alkoxyl, $C_1$-$C_{20}$ alkylthio, and $C_1$-$C_{20}$ alkylamino;
$R_4$ is selected from the group consisting of hydroxy, and

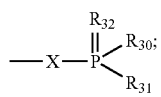

wherein $R_{32}$ is selected from the group consisting of O, NH and S;
X is selected from the group consisting of O, NH, S, $CH_2$, CHOH, CHF, $CF_2$, and

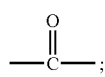

$R_{30}$ and $R_{31}$ are independently selected from the group consisting of $C_1$-$C_2$ alkoxy, hydroxy,

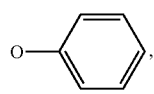 , 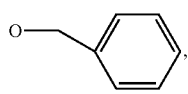 ,

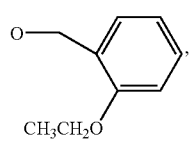 , 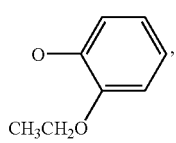 ,

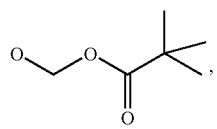 , 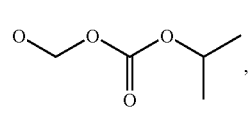 ,

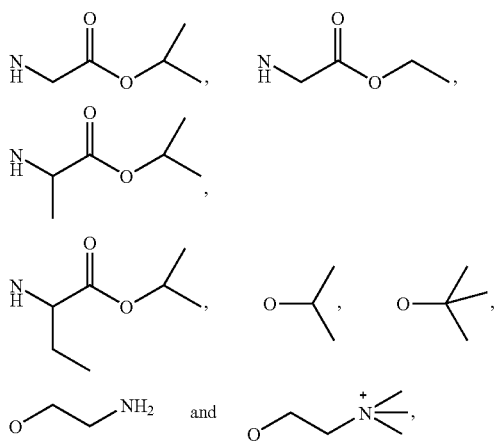

is a heterocyclic substituent selected from the group consisting of

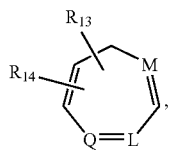 ,

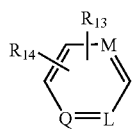 and 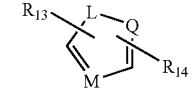

wherein L, M, and Q are selected from the group consisting of N, $NR_{15}$, O, S, $CR_{15}$, $CHR_{15}$ and $CR_{15}R_{16}$;
$R_{13}$, $R_{14}$, $R_{15}$ and $R_{16}$ are independently selected from the group consisting of H, halo, $C_1$-$C_6$ alkyl, $C_1$-$C_6$ haloalkyl and $C_1$-$C_6$ alkoxy; and
pharmaceutically acceptable salts thereof.

2. The compound of claim 1 wherein $R_1$ is selected from the group consisting of $C_8$-$C_{22}$ alkyl, $C_8$-$C_{22}$ alkenyl;
$R_4$ is selected from the group consisting of hydroxy, and

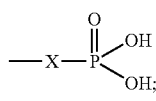

wherein X is selected from the group consisting of CH₂, CHOH, CHF, CF₂, and

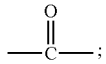

and

is a heterocyclic substituent represented by the formula

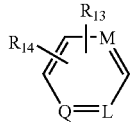

wherein L, M, and Q are selected from the group consisting of N, O, S, $CR_{15}$ and $CHR_{15}$;

$R_{13}$, $R_{14}$ and $R_{15}$ are independently selected from the group consisting of H, halo, $C_1$-$C_6$ alkyl, $C_1$-$C_6$ haloalkyl and $C_1$-$C_6$ alkoxy; and pharmaceutically acceptable salts thereof.

3. The compound of claim 2 wherein the compound is represented by the formula:

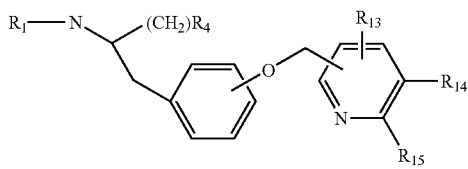

wherein $R_1$ is selected from the group consisting of $C_8$-$C_{22}$ alkyl, $C_8$-$C_{22}$ alkenyl, $C_8$-$C_{22}$ alkanoyl, $C_8$-$C_{22}$ alkenoyl, $R_4$ is selected from the group consisting of hydroxy, and

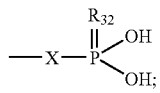

wherein $R_{32}$ is selected from the group consisting of O, NH and S;

X is selected from the group consisting of O, NH, S, CH₂, CHOH, CHF, CF₂, and

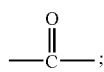

$R_{13}$, $R_{14}$ and $R_{15}$ are independently selected from the group consisting of H, halo, $C_1$-$C_6$ alkyl, $C_1$-$C_6$ haloalkyl and $C_1$-$C_6$ alkoxy; and pharmaceutically acceptable salts thereof.

4. The compound of claim 3 wherein the compound is represented by the formula:

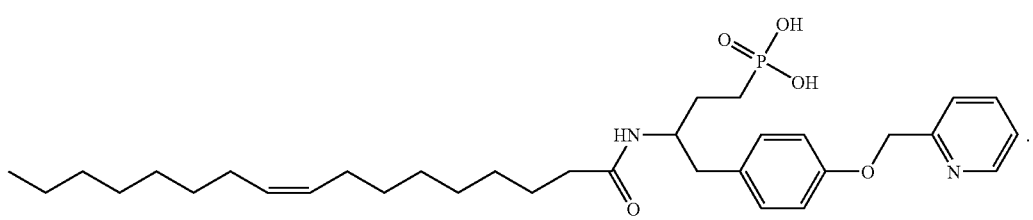

5. The compound of claim 4 wherein the compound is represented by the formula:

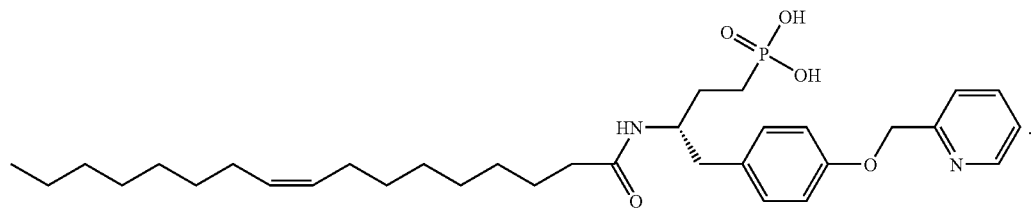

6. The compound of claim 4 wherein the compound is represented by the formula:

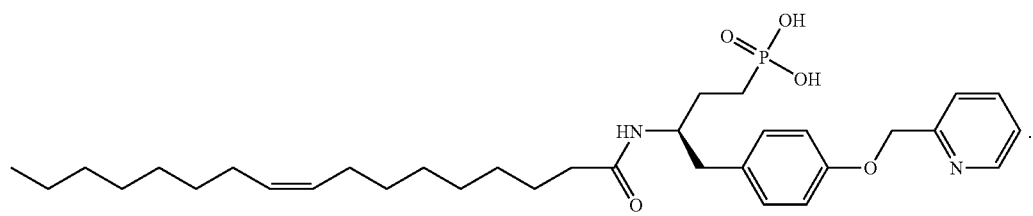

7. The compound of claim 3 wherein the compound is represented by the formula:

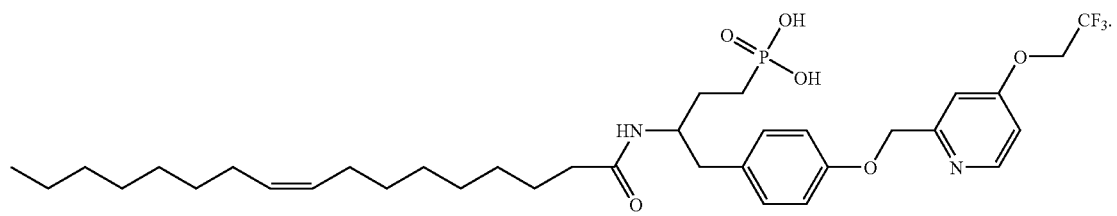

8. A composition comprising the compound of claim 1 and a pharmaceutically acceptable carrier.

9. A method of enhancing wound repair, said method comprising contacting the wound with a composition of claim 8.

10. A method of treating reperfusion type injury, said method comprising administering, to a patient in need thereof, an effective amount of a compound of claim 1.

11. A method of inhibiting lyso-lipid phosphate phosphatase activity, said method comprising the step of administering, to a patient in need thereof, an effective amount of a compound of claim 1.

12. The compound of claim 3 wherein the compound is represented by the formula:

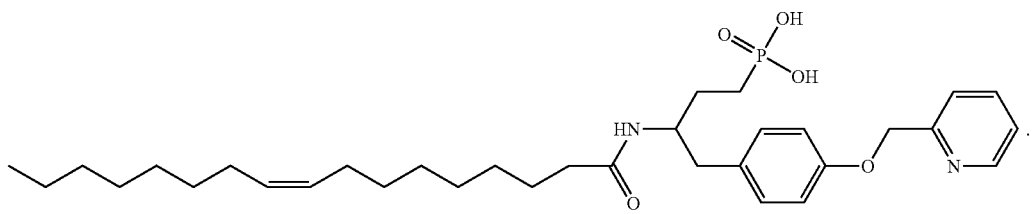

13. The compound of claim 12 wherein the compound is represented by the formula:

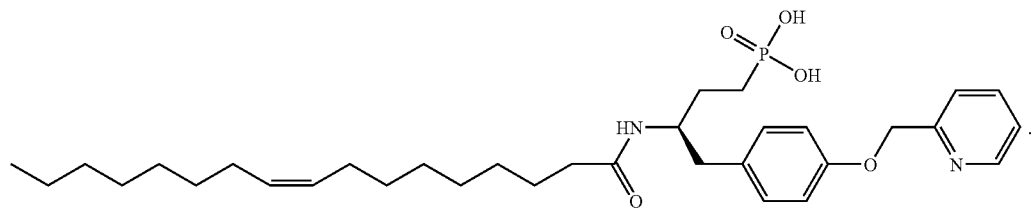

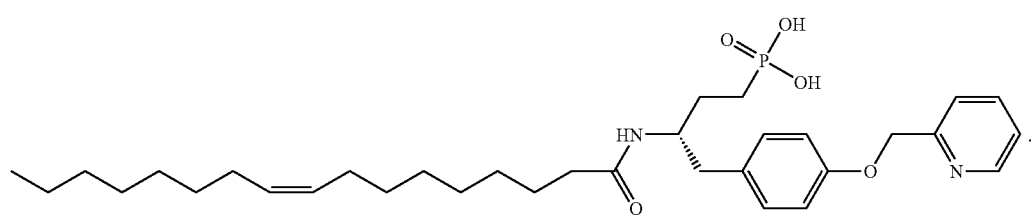

14. The compound of claim 12 wherein the compound is represented by the formula:

15. The compound of claim 3 wherein the compound is represented by the formula:

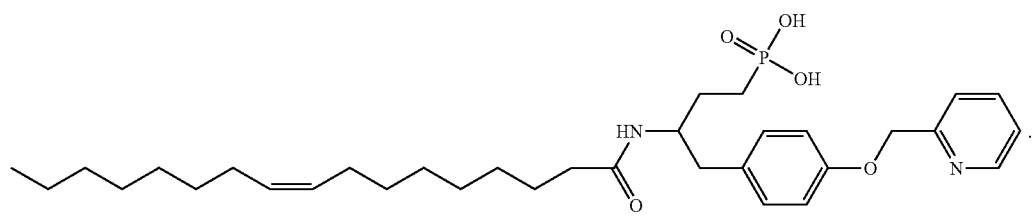

16. The compound of claim 15 wherein the compound is represented by the formula:

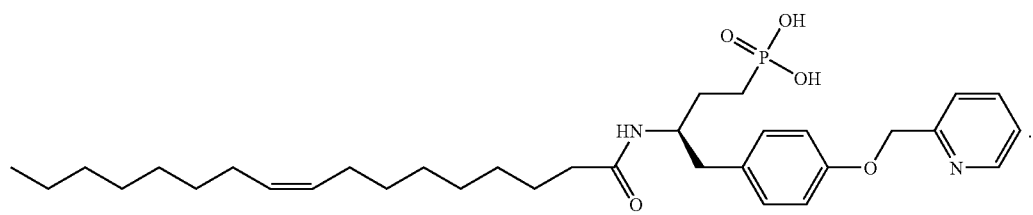

17. The compound of claim 15 wherein the compound is represented by the formula:

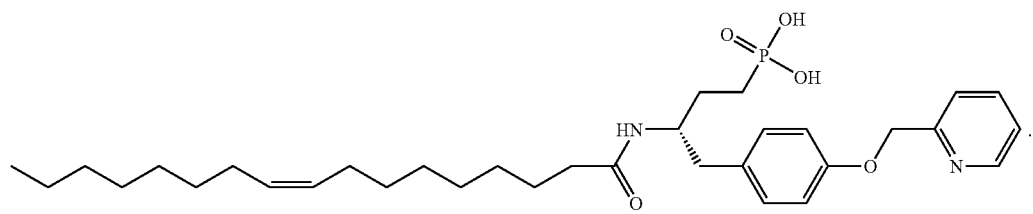

* * * * *